United States Patent
Burke et al.

(10) Patent No.: US 10,597,420 B2
(45) Date of Patent: *Mar. 24, 2020

(54) DERIVATIVES OF AMPHOTERICIN B

(71) Applicant: Sfunga Therapeutics, Inc., Boston, MA (US)

(72) Inventors: Martin D. Burke, Champaign, IL (US); Arun P. Thottumkara, Menlo Park, CA (US); Kevin T. Mellem, Redwood City, CA (US); Zachary K. Sweeney, Redwood City, CA (US); Elena S. Koltun, Foster City, CA (US)

(73) Assignee: Sfunga Therapeutics, Inc., Boston, MA (US)

( * ) Notice: Subject to any disclaimer, the term of this patent is extended or adjusted under 35 U.S.C. 154(b) by 60 days.

This patent is subject to a terminal disclaimer.

(21) Appl. No.: 15/948,122

(22) Filed: Apr. 9, 2018

(65) Prior Publication Data

US 2018/0273572 A1  Sep. 27, 2018

Related U.S. Application Data

(63) Continuation of application No. 15/099,837, filed on Apr. 15, 2016, now Pat. No. 9,957,290.

(60) Provisional application No. 62/147,949, filed on Apr. 15, 2015.

(51) Int. Cl.
 *C07H 17/08* (2006.01)

(52) U.S. Cl.
 CPC .................................. *C07H 17/08* (2013.01)

(58) Field of Classification Search
 None
 See application file for complete search history.

(56) References Cited

U.S. PATENT DOCUMENTS

| 5,066,646 A | 11/1991 | Driver et al. |
| 5,204,330 A | 4/1993 | Driver et al. |
| 9,957,290 B2* | 5/2018 | Burke .................... C07H 17/08 |
| 10,246,478 B2* | 4/2019 | Miyazaki ............... C07H 17/08 |
| 2004/0138437 A1 | 7/2004 | Chang et al. |

FOREIGN PATENT DOCUMENTS

| WO | WO-199317034 A1 | 9/1993 |
| WO | WO-1996032404 A1 | 10/1996 |
| WO | WO-2013186384 A1 | 12/2013 |
| WO | WO-2015/054148 A1 | 4/2015 |
| WO | WO-2015/175875 A1 | 11/2015 |
| WO | WO-2015/190587 A1 | 12/2015 |
| WO | WO-2016/014779 A1 | 1/2016 |
| WO | WO-2016/040779 A1 | 3/2016 |
| WO | WO-2016/061437 A1 | 4/2016 |
| WO | WO-2016/112243 A1 | 7/2016 |
| WO | WO-2016/112260 A1 | 7/2016 |

OTHER PUBLICATIONS

International Search Report and Written Opinion dated Jul. 15, 2016 in International Application No. PCT/US16/27703.
Extended European Search Report received for EP Patent Application No. EP16780813, dated Feb. 11, 2019.

* cited by examiner

*Primary Examiner* — Traviss C McIntosh, III
(74) *Attorney, Agent, or Firm* — Dana M. Gordon; Foley Hoag LLP

(57) ABSTRACT

Disclosed are derivatives of amphotericin B (AmB) characterized by improved therapeutic index compared to AmB. The AmB derivatives include C16 ureas, carbamates, and amides according to Formula (I); C3'-substituted C16 ureas, carbamates, and amides according to Formula (II); C16 acyls according to Formula (III); C2'epi-C16 ureas, carbamates, and amides according to Formula (IV); and C16 oxazolidinone derivatives according to Formula (V). Also disclosed are pharmaceutical compositions comprising the AmB derivatives, and therapeutic methods of using the AmB derivatives.

20 Claims, No Drawings

DERIVATIVES OF AMPHOTERICIN B

RELATED APPLICATIONS

This application is a continuation of U.S. patent application Ser. No. 15/099,837, filed Apr. 15, 2016; which claims the benefit of priority from U.S. Provisional Patent Application No. 62/147,949, filed Apr. 15, 2015.

BACKGROUND OF THE INVENTION

For more than half a century amphotericin B (AmB) has served as the gold standard for treating systemic fungal infections. AmB has a broad spectrum of activity, is fungicidal, and is effective even against fungal strains that are resistant to multiple other agents. Surprisingly, clinically significant microbial resistance has remained exceptionally rare while resistance to next generation antifungals has appeared within just a few years of their clinical introduction. Unfortunately, AmB is also highly toxic. Deray, G, *J Antimicrob Chemother* 49 Suppl 1: 37-41 (2002). Thus, the effective treatment of systemic fungal infections with AmB is all too often precluded, not by a lack of efficacy, but by dose-limiting side effects. Mora-Duarte, J et al., *N Engl J Med* 347: 2020-9 (2002). Some progress has been made using liposome delivery systems, but these treatments are prohibitively expensive and significant toxicities remain. Wong-Beringer, A et al., *Clin Infect Dis* 27: 603-18 (1998). Thus, a need exists for an effective but less toxic form or derivative of AmB.

SUMMARY OF THE INVENTION

An aspect of the invention is a compound represented by Formula (I) or a pharmaceutically acceptable salt thereof:

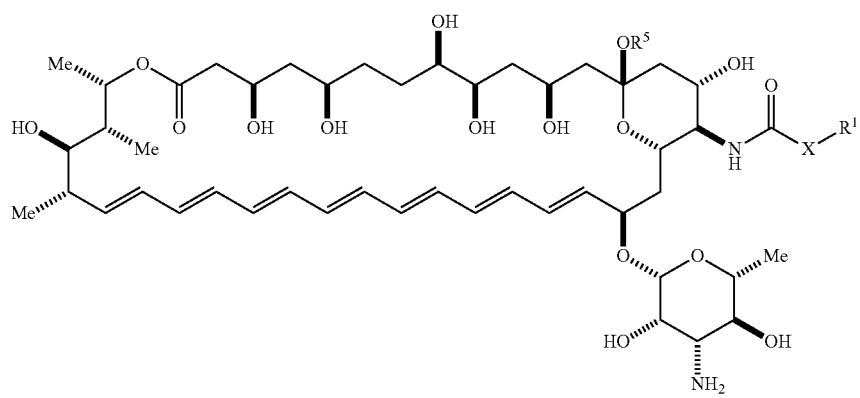

(I)

wherein, independently for each occurrence:

X is —N($R^2$)—, —C($R^3$)($R^3$)—, or —O—;

$R^2$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;

$R^3$ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl;

$R^5$ is selected from the group consisting of hydrogen, alkyl, and haloalkyl;

when X is —N($R^2$)—, $R^1$ is a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or $R^1$ and $R^2$, together with the nitrogen to which they are attached, may form a substituted or unsubstituted 3- to 10-membered heterocyclic ring, wherein said ring is monocyclic, bicyclic, tricyclic, or spirocyclic;

when X is —C($R^3$)($R^3$)—, $R^1$ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, alkyl, aryl, heteroaryl, aralkyl, heteroaralkyl, carboxyl, acyl, acyloxy, amino, amido, azido, aminoalkyl, and alkoxyl; or the two instances of $R^3$, together with the carbon to which they are attached, may form a substituted or unsubstituted 3- to 10-membered aliphatic or heterocyclic ring, wherein said ring is monocyclic, bicyclic, tricyclic, or spirocyclic; and when X is —O—, $R^1$ is a substituted or unsubstituted group selected from the group consisting of alkyl, alkenyl, cycloalkyl, (cycloalkyl)alkyl, heterocyclyl, (heterocyclyl) alkyl, aryl, heteroaryl, aralkyl, heteroaralkyl, acyl, amino, amido, and aminoalkyl;

provided that when $R^5$ is hydrogen, —X$R^1$ is not —N(H)CH$_3$, —N(H)(CH$_2$)$_2$NH$_2$, —N(H)(CH$_2$)$_2$COOH, —N(CH$_3$)$_2$, —N(CH$_2$CH$_3$)$_2$, —N(CH(CH$_3$)$_2$)$_2$,

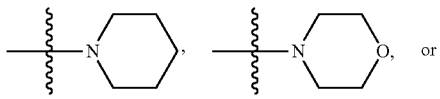

-continued

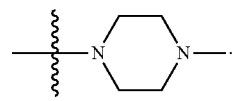

An aspect of the invention is a compound represented by Formula (II) or a pharmaceutically acceptable salt thereof:

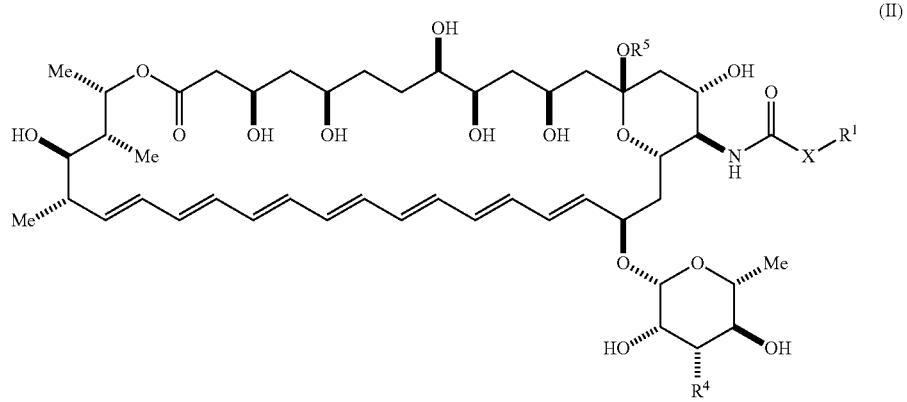

(II)

wherein, independently for each occurrence:

X is —N(R$^2$)—, —C(R$^3$)(R$^3$)—, or —O—;

R$^2$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;

R$^3$ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl;

when X is —N(R$^2$)—, R$^1$ is a substituted or unsubstituted group selected from the group consisting of alkyl, cycloalkyl, (cycloalkyl)alkyl, heterocyclyl, (heterocyclyl) alkyl, aryl, heteroaryl, aralkyl, heteroaralkyl, acyl, amino, amido, aminoalkyl, and alkoxyl; or R$^1$ and R$^2$, together with the nitrogen to which they are attached, may form a substituted or unsubstituted 3- to 10-membered heterocyclic ring, wherein said ring is monocyclic, bicyclic, tricyclic, or spirocyclic;

when X is —C(R$^3$)(R$^3$)—, R$^1$ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl) alkyl, aryl, heteroaryl, aralkyl, heteroaralkyl, carboxyl, acyl, acyloxy, amino, amido, azido, aminoalkyl, and alkoxyl; or the two instances of R$^3$, together with the carbon to which they are attached, may form a substituted or unsubstituted 3- to 10-membered aliphatic or heterocyclic ring, wherein said ring is monocyclic, bicyclic, tricyclic, or spirocyclic;

when X is —O—, R$^1$ is a substituted or unsubstituted group selected from the group consisting of alkyl, alkenyl, cycloalkyl, (cycloalkyl)alkyl, heterocyclyl, (heterocyclyl) alkyl, aryl, heteroaryl, aralkyl, heteroaralkyl, acyl, amino, amido, and aminoalkyl;

R$^4$ is secondary amino, tertiary amino, amido, azido, isonitrile, nitro, urea, isocyanate, carbamate, or guanidinyl; and R$^5$ is selected from the group consisting of hydrogen, alkyl, and haloalkyl.

An aspect of the invention is a compound represented by Formula (III) or a pharmaceutically acceptable salt thereof:

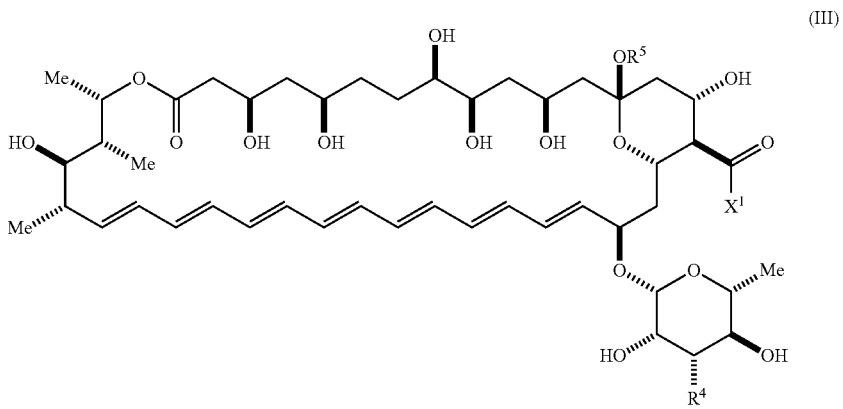

(III)

wherein, independently for each occurrence:

X$^1$ is —N(R$^6$)(R$^7$), —OR$^8$, or —R$^9$;

R$^6$ and R$^7$ are independently hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or, R$^6$ and R$^7$, together with the nitrogen to which they are attached, may form a substituted or unsubstituted 3- to 10-membered heterocyclic ring, wherein said ring is monocyclic, bicyclic, tricyclic, or spirocyclic;

R$^8$ is a substituted or unsubstituted group selected from the group consisting of alkyl, heteroalkyl, cycloalkyl, (cycloalkyl)alkyl, alkenyl, heterocyclyl, aryl, heteroaryl, aralkyl, heteroaralkyl, acyl, amino, amido, and aminoalkyl;

$R^9$ is hydrogen, halogen, hydroxyl, sulfhydryl, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, aminoalkyl, and alkoxyl;

$R^4$ is secondary amino, tertiary amino, amido, azido, isonitrile, nitro, urea, isocyanate, carbamate, or guanidinyl; and $R^5$ is selected from the group consisting of hydrogen, alkyl, and haloalkyl.

An aspect of the invention is a compound represented by Formula (IV) or a pharmaceutically acceptable salt thereof:

$R^5$ is selected from the group consisting of hydrogen, alkyl, and haloalkyl;

when X is —N($R^2$)—, $R^1$ is a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or $R^1$ and $R^2$, together with the nitrogen to which they are attached, may form a substituted or unsubstituted 3- to 10-membered heterocyclic ring, wherein said ring is monocyclic, bicyclic, tricyclic, or spirocyclic;

when X is —C($R^3$)($R^3$)—, $R^1$ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)

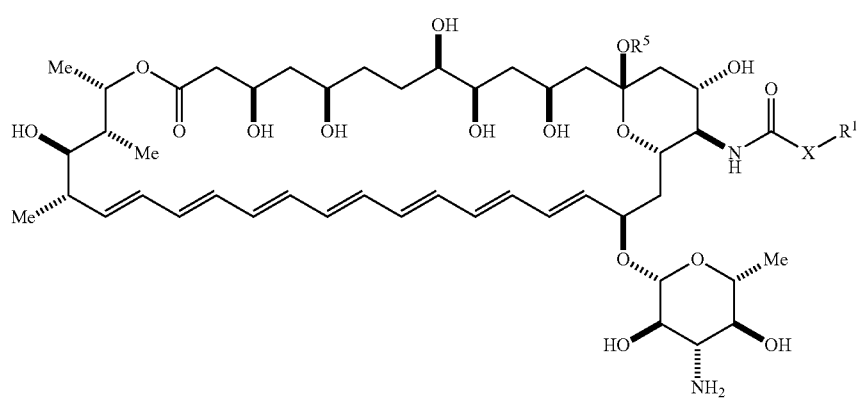

(IV)

wherein, independently for each occurrence:

X is —N($R^2$)—, —C($R^3$)($R^3$)—, or —O—;

$R^2$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;

$R^3$ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl;

alkyl, aryl, heteroaryl, aralkyl, heteroaralkyl, carboxyl, acyl, acyloxy, amino, amido, azido, aminoalkyl, and alkoxyl; or the two instances of $R^3$, together with the carbon to which they are attached, may form a substituted or unsubstituted 3- to 10-membered aliphatic or heterocyclic ring, wherein said ring is monocyclic, bicyclic, tricyclic, or spirocyclic; and when X is —O—, $R^1$ is a substituted or unsubstituted group selected from the group consisting of alkyl, alkenyl, cycloalkyl, (cycloalkyl)alkyl, heterocyclyl, (heterocyclyl)alkyl, aryl, heteroaryl, aralkyl, heteroaralkyl, acyl, amino, amido, and aminoalkyl.

An aspect of the invention is a compound represented by Formula (V) or a pharmaceutically acceptable salt thereof:

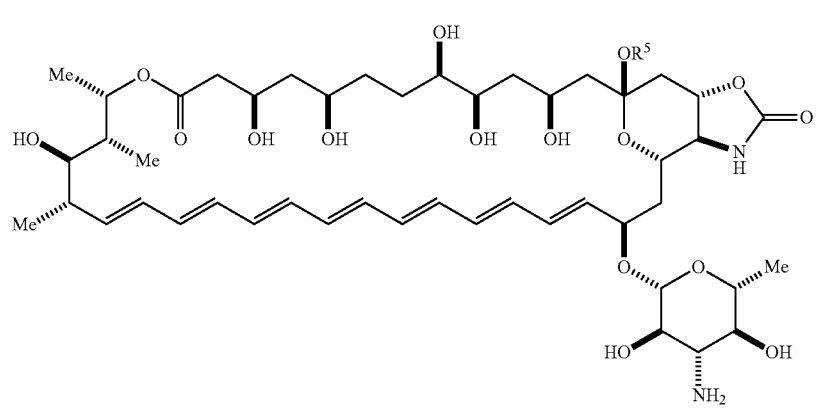

(V)

wherein $R^5$ is selected from the group consisting of hydrogen, alkyl, and haloalkyl.

An aspect of the invention is a pharmaceutical composition, comprising a compound of the invention, or a pharmaceutically acceptable salt thereof, and a pharmaceutically acceptable carrier.

An aspect of the invention is a method of treating a fungal infection, comprising administering to a subject in need thereof a therapeutically effective amount of a compound of the invention, thereby treating the fungal infection.

DETAILED DESCRIPTION OF THE INVENTION

Amphotericin B (AmB) is a polyene macrolide with a mycosamine appendage, the complete compound having the following structure:

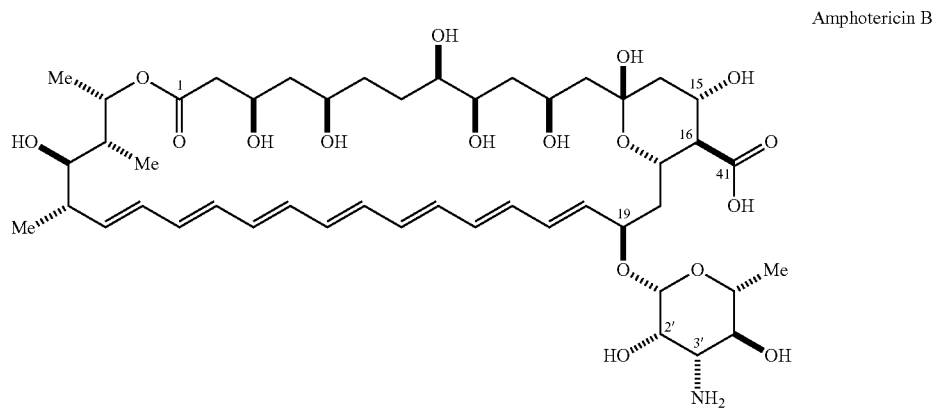

Amphotericin B

AmB is generally obtained from a strain of *Streptomyces nodosus*. It is currently approved for clinical use in the United States for the treatment of progressive, potentially life-threatening fungal infections, including such infections as systemic or deep tissue candidiasis, aspergillosis, cryptococcosis, blastomycosis, coccidioidomycosis, histoplasmosis, and mucormycosis, among others. It is generally formulated for intravenous injection. Amphotericin B is commercially available, for example, as Fungizone® (Squibb), Amphocin® (Pfizer), Abelcet® (Enzon), and Ambisome® (Astellas). Due to its undesirable toxic side effects, dosing is generally limited to a maximum of about 1.0 mg/kg/day and total cumulative doses not to exceed about 3 g in humans.

It has for many decades been widely accepted that AmB kills both yeast and human cells primarily via membrane permeabilization. However, a lack of understanding of the mechanism(s) by which AmB is toxic to yeast and human cells has thus far hindered the rational development of a clinically successful derivative. The longstanding accepted mechanism of action of AmB has been ion channel formation within a cell's membrane, leading to electrochemical gradient disruption and eventually cell death. This model suggests that development of a less toxic derivative requires selective ion channel formation in yeast versus human cells.

Contrary to this longstanding model, it was recently reported that the primary mechanism of action of AmB is not ion channel formation, but simple ergosterol binding. Gray, K C et al., *Proc Natl Acd Sci USA* 109: 2234-9 (2012). Yeast and human cells possess different sterols, ergosterol and cholesterol, respectively. A derivative was recently reported in which removal of the C2' hydroxyl group from the mycosamine sugar produced a derivative, C2'deOAmB, which surprisingly retains ergosterol-binding ability, but shows no binding to cholesterol. Wilcock, B C et al., *J Am Chem Soc* 135: 8488-91 (2013). Consistent with the preferential sterol binding hypothesis, in vitro studies demonstrated that C2'deOAmB is toxic to yeast but not to human cells. See WO 2014/165676 to Burke et al., the entire content of which is incorporated herein by reference.

The present invention relates, at least in part, to the discovery by the inventors of further derivatives of AmB which also are characterized by improved therapeutic index compared to AmB. The various derivatives, i.e., compounds of the invention, can be semi-synthetic or fully synthetic.

Compounds of the invention and pharmaceutical compositions of the invention are useful for inhibiting the growth of a fungus. In one embodiment, an effective amount of a compound of the invention is contacted with a fungus, thereby inhibiting growth of the fungus. In one embodiment, a compound of the invention, or a pharmaceutically acceptable salt thereof, is added to or included in tissue culture medium.

Compounds of the invention and pharmaceutical compositions of the invention are useful for the treatment of fungal infections in a subject. In one embodiment, a therapeutically effective amount of a compound of the invention, or a pharmaceutically acceptable salt thereof, is administered to a subject in need thereof, thereby treating the fungal infection.

A fungus is a eukaryotic organism classified in the kingdom Fungi. Fungi include yeasts, molds, and larger organisms including mushrooms. Yeasts and molds are of clinical relevance as infectious agents.

Yeasts are eukaryotic organisms classified in the kingdom Fungi. Yeasts are typically described as budding forms of fungi. Of particular importance in connection with the invention are species of yeast that can cause infections in mammalian hosts. Such infections most commonly occur in immunocompromised hosts, including hosts with compromised barriers to infection (e.g., burn victims) and hosts with compromised immune systems (e.g., hosts receiving chemotherapy or immune suppressive therapy, and hosts infected with HIV). Pathogenic yeasts include, without limitation, various species of the genus *Candida*, as well as of *Cryptococcus*. Of particular note among pathogenic yeasts of the genus *Candida* are *C. albicans*, *C. tropicalis*,

*C. stellatoidea, C. glabrata, C. krusei, C. parapsilosis, C. guilliermondii, C. viswanathii,* and *C. lusitaniae.* The genus *Cryptococcus* specifically includes *Cryptococcus neoformans.* Yeast can cause infections of mucosal membranes, for example oral, esophageal, and vaginal infections in humans, as well as infections of bone, blood, urogenital tract, and central nervous system. This list is exemplary and is not limiting in any way.

A number of fungi (apart from yeast) can cause infections in mammalian hosts. Such infections most commonly occur in immunocompromised hosts, including hosts with compromised barriers to infection (e.g., burn victims) and hosts with compromised immune systems (e.g., hosts receiving chemotherapy or immune suppressive therapy, and hosts infected with HIV). Pathogenic fungi (apart from yeast) include, without limitation, species of *Aspergillus, Rhizopus, Mucor, Histoplasma, Coccidioides, Blastomyces, Trichophyton, Microsporum,* and *Epidermophyton.* Of particular note among the foregoing are *A. fumigatus, A. flavus, A. niger, H. capsulatum, C. immitis,* and *B. dermatitidis.* Fungi can cause systemic and deep tissue infections in lung, bone, blood, urogenital tract, and central nervous system, to name a few. Some fungi are responsible for infections of the skin and nails.

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The term "acyl", as used herein, refers to —C(=O)R, where R represents an alkyl, aryl, heteroaryl, aralkyl, or heteroaralkyl group as defined herein. Amides (RC(O)NR$_2$) and esters (RC(O)OR') are classes of acyl compounds, as are ketones (RC(O)R) and aldehydes (RC(O)H). Non-limiting examples of acyl groups include formyl, acetyl, propionyl, and benzyl.

The terms "alkenyl" and "alkynyl" are art-recognized and refer to unsaturated aliphatic groups analogous in length and possible substitution to the alkyls described herein, but that contain at least one double or triple bond, respectively.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkyl" is art-recognized, and includes saturated aliphatic groups, including straight-chain alkyl groups, branched-chain alkyl groups, and cycloalkyl (alicyclic) groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer. In certain embodiments, a straight-chain or branched-chain alkyl has about 10 or fewer carbon atoms in its backbone. In certain embodiments, a straight-chain alkyl has 1 to 6 carbon atoms in its backbone. In certain embodiments, a branched-chain alkyl has 3 to 8 carbon atoms in its backbone. Representative examples of linear and branched-chain alkyl groups include, but are not limited to, methyl, ethyl, n-propyl, iso-propyl, n-butyl, sec-butyl, iso-butyl, tert-butyl, n-pentyl, isopentyl, neopentyl, and n-hexyl. Cycloalkyls have from about 3 to about 10 carbon atoms in their ring structure. In certain embodiments, cycloalkyls have 3, 4, 5, 6, or 7 carbons in the ring structure. Representative examples of cycloalkyl groups include, but are not limited to, cyclopropyl, cyclobutyl, cyclopentyl, cyclohexyl, and cycloheptyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy", as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylthio", as used herein, means an alkyl group, as defined herein, appended to the parent molecular moiety through a sulfur atom. Representative examples of alkylthio include, but are not limited, methylthio, ethylthio, tert-butylthio, and hexylthio. The terms "arylthio", "alkenylthio", and "arylalkylthio," for example, are likewise defined in a corresponding fashion.

The term "amido", as used herein, refers to a moiety that may be represented by the general formula:

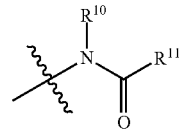

wherein $R^{10}$ and $R^{11}$ each independently represent hydrogen or a substituted or unsubstituted group selected from alkyl, cycloalkyl, cycloalkylalkyl, heterocyclyl, alkenyl, cycloalkenyl, aminoalkyl, aryl, heteroaryl, aralkyl, and heteroaralkyl. Nonlimiting examples of amido include those for which $R^{10}$ is hydrogen, and $R^{11}$ is selected from methyl, ethyl, propyl, isopropyl, propenyl, cyclohexyl, benzyl,

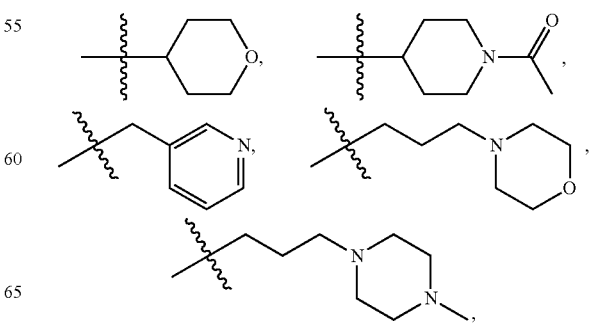

-continued

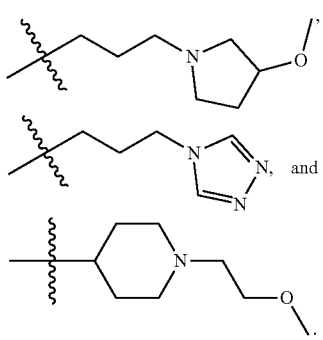

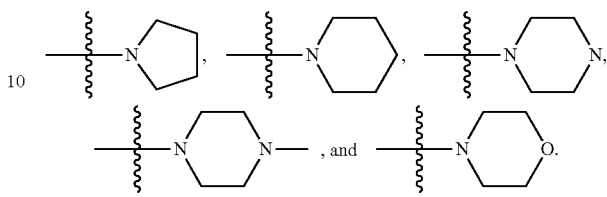

Additional nonlimiting examples of amido include those for which $R^{10}$ is hydrogen, and $R^{11}$ is selected from —CH$_2$NH$_2$, —CH$_2$N(CH$_3$)$_2$, and —CH(NH$_2$)(CH$_2$)$_n$NH$_2$, where n is an integer 1-6. Yet additional nonlimiting examples of amido include those for which $R^{10}$ is hydrogen, and $R^{11}$ is selected from

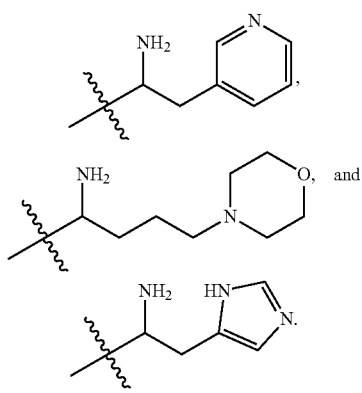

The terms "amino" and "amine" are art-recognized and refer to both unsubstituted and substituted amines, e.g., a moiety that may be represented by the general formulas:

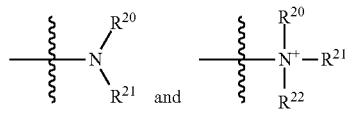

wherein $R^{20}$, $R^{21}$, and $R^{22}$ each independently represent a hydrogen, an alkyl, an alkenyl, —(CH$_2$)$_m$—$R^{61}$; or $R^{20}$ and $R^{21}$, taken together with the N atom to which they are attached, complete a heterocycle having from 4 to 10 atoms in the ring structure, wherein said ring is monocyclic, bicyclic, tricyclic, or spirocyclic; $R^{61}$ represents an aryl, a cycloalkyl, a cycloalkenyl, a heterocycle or a polycycle; and m is zero or an integer in the range of 1 to 8. In other embodiments, $R^{20}$ and $R^{21}$ (and optionally $R^{22}$) each independently represent a hydrogen, an alkyl, an alkenyl, or —(CH$_2$)$_m$—$R^{61}$. Thus, the term "alkylamine" includes an amine group, as defined above, having a substituted or unsubstituted alkyl attached thereto, i.e., at least one of $R^{20}$ and $R^{21}$ is an alkyl group. Nonlimiting examples of amino groups include —NH$_2$, —N(H)CH$_3$, —N(H)CH$_2$CH$_3$, —N(H)CH$_2$CH$_2$CH$_3$, —N(H)CH$_2$CH$_2$CH$_2$CH$_3$, —N(CH$_3$)$_2$, —N(CH(CH$_3$)$_2$)$_2$, —N(CH$_3$)CH$_2$CH$_3$, —N(CH$_3$)CH$_2$CH$_2$CH$_3$, —N(CH$_3$)CH$_2$CH$_2$CH$_2$CH$_3$, —N(CH$_2$CH$_3$)$_2$, —N(CH$_2$CH$_3$)CH$_2$CH$_2$CH$_3$, —N(CH$_2$CH$_3$)CH$_2$CH$_2$CH$_2$CH$_3$, —N(CH$_2$CH$_3$)$_2$, —N(CH$_2$CH$_2$CH$_3$)CH$_2$CH$_2$CH$_2$CH$_3$, —N(CH$_2$CH$_2$CH$_2$CH$_3$)$_2$, In certain embodiments, amino is —NH$_2$. In certain embodiments, amino is —N(H)CH$_3$.

The term "aminoalkyl" as used herein, means an amino group, as defined herein, appended to the parent molecular moiety through an alkyl group, also as defined herein.

The term "aromatic" refers to a planar monocyclic or polycyclic structure characterized by a cyclically conjugated molecular moiety containing 4n+2 electrons, wherein n is the absolute value of an integer. Aromatic groups comprising only carbon atoms in their ring structure are termed "aryl" groups. Aromatic groups comprising one or more heteroatoms in their ring structure are termed "heteroaryl" or "heteroaromatic" groups. Aromatic groups containing fused, or joined, rings also are referred to as polycyclic aromatic groups. For example, bicyclic aromatic groups containing heteroatoms in a hydrocarbon ring structure are referred to as bicyclic heteroaryl groups.

Examples of 5-, 6-, and 7-membered single-ring aromatic groups that may include from zero to four heteroatoms include, for example, benzene, pyrrole, furan, thiophene, imidazole, oxazole, thiazole, triazole, pyrazole, pyridine, pyrazine, pyridazine, pyrimidine, and the like.

Non-limiting examples of polycyclic aromatic and heteroaromatic groups include quinoline, isoquinoline, carbazole, naphthalene, anthracene, and pyrene.

The aryl groups of the invention can be optionally substituted with 1, 2, 3, 4 or 5 substituents independently selected from the group consisting of alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The term "arylcarbonyloxy", as used herein, means an arylcarbonyl group, as defined herein, appended to the parent molecular moiety through an oxygen atom. Representative examples of arylcarbonyloxy include, but are not limited to, phenylcarbonyloxy.

The term "arylene" is art-recognized, and, as used herein, pertains to a bidentate moiety obtained by removing two hydrogen atoms of an aryl ring, as defined above.

The term "arylalkyl" or "aralkyl", as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "azido", as used herein, refers to —N₃.

The term "carbamate", as used herein, refers to a moiety that may be represented by the general formula:

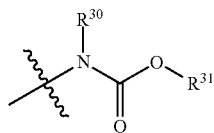

wherein $R^{30}$ and $R^{31}$ each independently represent hydrogen or a substituted or unsubstituted group selected from alkyl, cycloalkyl, cycloalkylalkyl, heterocyclyl, alkenyl, cycloalkenyl, aryl, heteroaryl, aralkyl, and heteroaralkyl. Nonlimiting examples of carbamate include those for which $R^{30}$ is hydrogen, and $R^{31}$ is selected from methyl, ethyl, propyl, isopropyl, propenyl, cyclohexyl, benzyl,

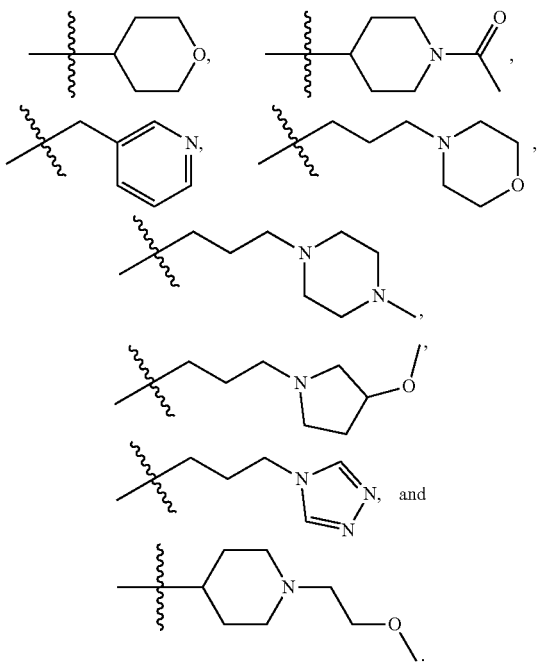

The term "carbonyl", as used herein, means a —C(=O)— group.

The term "carboxyl", as used herein, means a —CO₂H group.

The term "cyano", as used herein, means a —CN group.

The term "cycloalkylalkyl" as used herein, refers to a cycloalkyl group, as defined herein, appended to the parent molecular moiety through an alkyl group, also as defined herein.

The term "guanidinyl", as used herein, refers to a moiety that may be represented by the general formula:

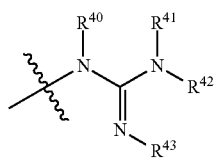

wherein $R^{40}$, $R^{41}$, $R^{42}$, and $R^{43}$ each independently represent hydrogen or a substituted or unsubstituted group selected from alkyl, cycloalkyl, cycloalkylalkyl, heterocyclyl, alkenyl, cycloalkenyl, aryl, heteroaryl, aralkyl, and heteroaralkyl. In one embodiment, $R^{40}$, $R^{41}$, $R^{42}$, and $R^{43}$ each represent hydrogen.

The term "halo" or "halogen" means —F, —Cl, —Br, or —I.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaralkyl", as used herein, means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "heteroaryl", as used herein, includes aromatic ring systems, including, but not limited to, monocyclic, bicyclic, and tricyclic rings, and have 3 to 12 atoms including at least one heteroatom, such as nitrogen, oxygen, or sulfur. For purposes of exemplification, which should not be construed as limiting the scope of this invention, the following are examples of heteroaryl: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups may be substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroatom" is art-recognized and refers to an atom of any element other than carbon or hydrogen. Illustrative heteroatoms include boron, nitrogen, oxygen, phosphorus, sulfur, and selenium.

The term "heterocyclyl", as used herein, refers to nonaromatic ring systems, including, but not limited to, monocyclic, bicyclic, tricyclic and spirocyclic rings, which can be completely saturated or which can contain one or more units of unsaturation (for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups may be substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "hydroxyl", as used herein, means an —OH group.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "nitro", as used herein, means a —NO$_2$ group.

The term "silyl", as used herein, includes hydrocarbyl derivatives of the silyl (H$_3$Si—) group (i.e., (hydrocarbyl)$_3$Si—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy", as used herein, means a silyl group, as defined herein, is appended to the parent molecule through an oxygen atom.

The term "sulfhydryl", as used herein, means a —SH group.

The term "sulfonyl" is art-recognized and refers to —SO$_2^-$.

The term "urea", as used herein, means a moiety that may be represented by the general formula:

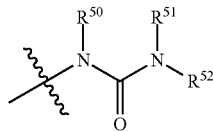

wherein R$^{50}$, R$^{51}$, and R$^{52}$, each independently represent hydrogen, an alkyl, an alkenyl, —(CH$_2$)$_m$—R$^{61}$; or R$^{51}$ and R$^{52}$, taken together with the N atom to which they are attached, complete a heterocycle having from 4 to 10 atoms in the ring structure, wherein said ring is monocyclic, bicyclic, tricyclic, or spirocyclic; R$^{61}$ represents an aryl, a cycloalkyl, a cycloalkenyl, a heterocycle or a polycycle; and m is zero or an integer in the range of 1 to 8. Nonlimiting examples of urea include those for which R$^{50}$ is hydrogen, and R$^{51}$ and R$^{52}$ are selected in accordance with Table 1 herein.

The definition of each expression, e.g., alkyl, m, n, and the like, when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the invention may exist in particular geometric or stereoisomeric forms. In addition, polymers of the invention may also be optically active. The invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkenyl, alkynyl, aryl, aralkyl, heterocyclyl, (heterocyclyl)alkyl, (cycloalkyl)alkyl, alkoxy, aryloxy, alkoxycarbonyl, alkoxysulfonyl, aryloxycarbonyl, aryloxysulfonyl, alkylcarbonyl, arylcarbonyl, alkylcarbonyloxy, arylcarbonyloxy, alkylsulfonyl, arylsulfonyl, alkylsulfonyloxy, arylsulfonyloxy, alkylthio, arylthio, amido, amino, carboxy, cyano, formyl, halo, haloalkoxy, haloalkyl, hydroxyl, hydroxyalkyl, mercapto, nitro, phosphinyl, acyl, acyloxy, silyl and silyloxy. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention.

For purposes of this invention, the chemical elements are identified in accordance with the Periodic Table of the Elements, CAS version, Handbook of Chemistry and Physics, 67th Ed., 1986-87, inside cover.

Compounds of the Invention

The invention provides a number of derivatives of AmB, including derivatives characterized by (i) certain modifications at C16; (ii) the combination of certain modifications at C16, and certain N modifications at C3'; (iii) the combination of other modifications at C16, and certain N modifications at C3'; (iv) the combination of certain modifications at C16, and C2' epimerization; and (v) certain oxazolidinone derivatives.

For example, the invention provides a number of derivatives of AmB, including derivatives characterized by (i) certain urea, amide, and carbamate modifications at C16; (ii) the combination of certain urea, amide, and carbamate modifications at C16, and certain N modifications at C3'; (iii) the combination of certain ester, amide, aldehyde, and ketone modifications at C16, and certain N modifications at C3'; (iv) the combination of certain urea, amide, and carbamate modifications at C16, and C2' epimerization; and (v) certain oxazolidinone derivatives.

An aspect of the invention is a compound represented by Formula (I) or a pharmaceutically acceptable salt thereof:

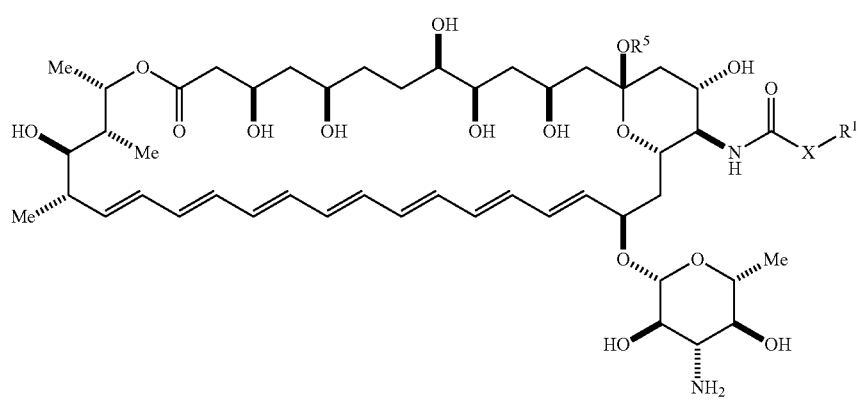

(I)

wherein, independently for each occurrence:

X is —N(R$^2$)—, —C(R$^3$)(R$^3$)—, or —O—;

R$^2$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;

R$^3$ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl;

R$^5$ is selected from the group consisting of hydrogen, alkyl, and haloalkyl;

when X is —N(R$^2$)—, R$^1$ is a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or R$^1$ and R$^2$, together with the nitrogen to which they are attached, may form a substituted or unsubstituted 3- to 10-membered heterocyclic ring, wherein said ring is monocyclic, bicyclic, tricyclic, or spirocyclic;

when X is —C(R$^3$)(R$^3$)—, R$^1$ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl; or the two instances of R$^3$, together with the carbon to which they are attached, may form a substituted or unsubstituted 3- to 10-membered aliphatic or heterocyclic ring, wherein said ring is monocyclic, bicyclic, tricyclic, or spirocyclic; and when X is —O—, R$^1$ is a substituted or unsubstituted group selected from the group consisting of alkyl, alkenyl, cycloalkyl, (cycloalkyl)alkyl, heterocyclyl, (heterocyclyl)alkyl, aryl, heteroaryl, aralkyl, heteroaralkyl, acyl, amino, amido, and aminoalkyl;

provided that when R$^5$ is hydrogen, —XR$^1$ is not —N(H)CH$_3$, —N(H)(CH$_2$)$_2$NH$_2$, —N(H)(CH$_2$)$_2$COOH, —N(CH$_3$)$_2$, —N(CH$_2$CH$_3$)$_2$, —N(CH(CH$_3$)$_2$)$_2$,

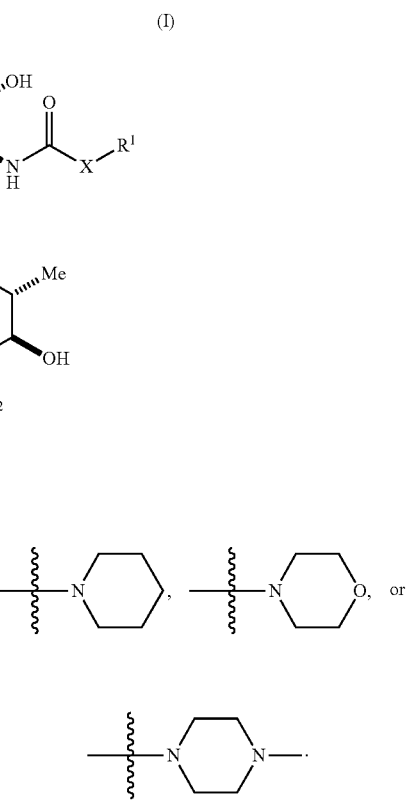

In certain embodiments, R$^2$ is hydrogen.

In certain embodiments, X is —N(R$^2$)—.

In certain embodiments, X is —N(R$^2$)—, wherein R$^2$ is hydrogen.

In certain embodiments, X is —C(R$^3$)(R$^3$)—.

In certain embodiments, X is —O—.

In certain embodiments, —XR$^1$ is selected from the group consisting of

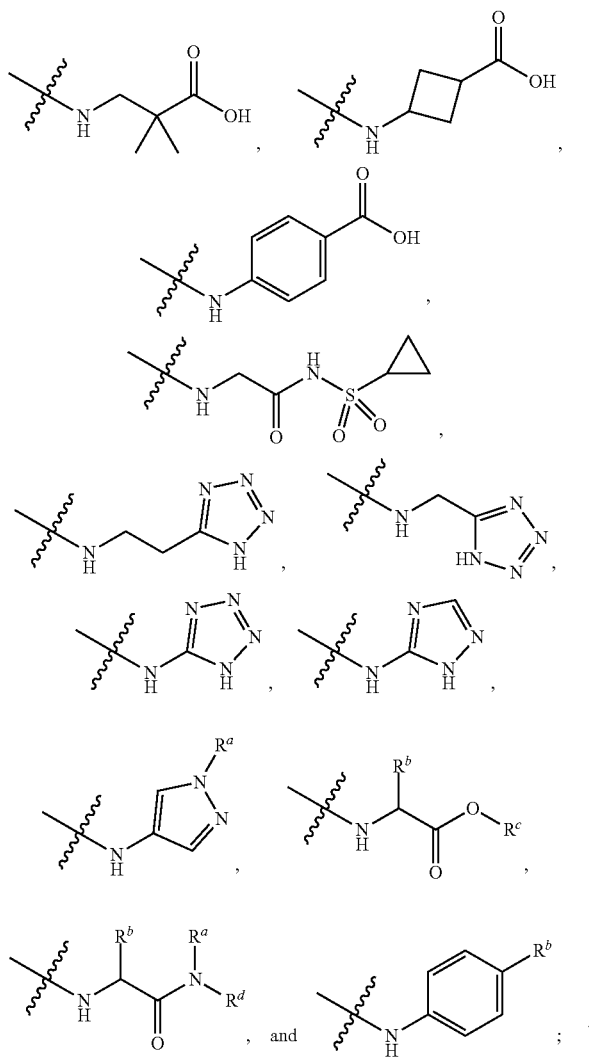

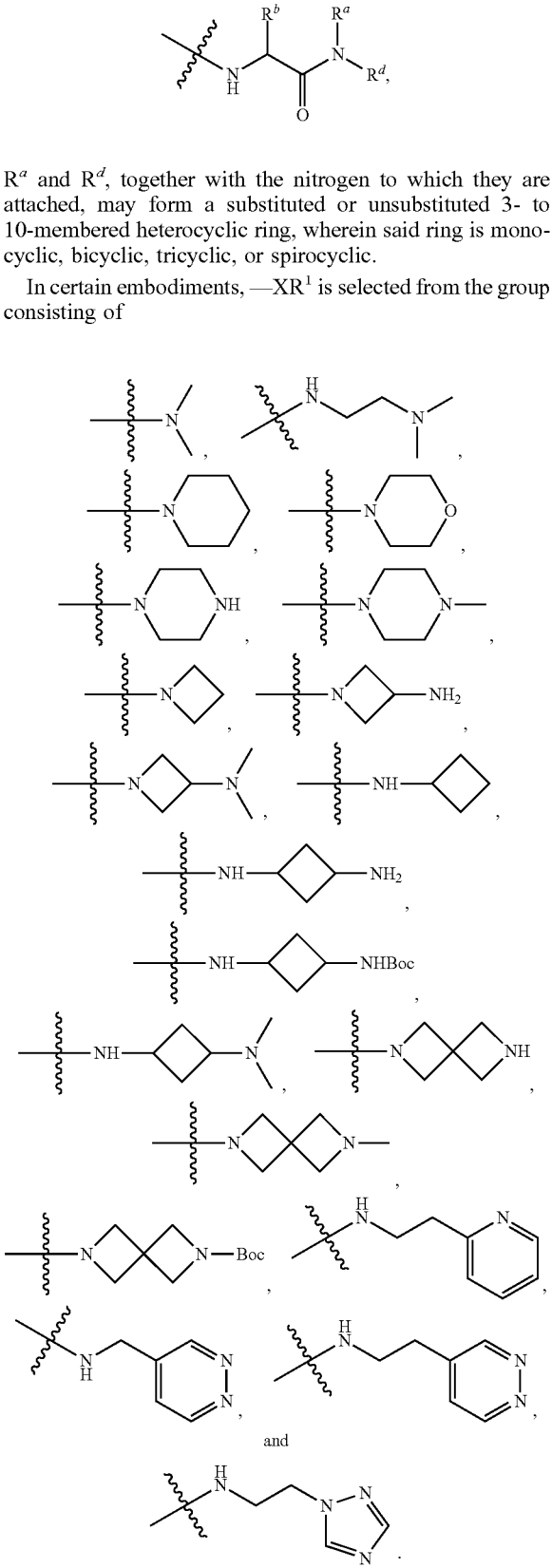

$R^a$ and $R^d$, together with the nitrogen to which they are attached, may form a substituted or unsubstituted 3- to 10-membered heterocyclic ring, wherein said ring is monocyclic, bicyclic, tricyclic, or spirocyclic.

In certain embodiments, —$XR^1$ is selected from the group consisting of wherein, independently for each occurrence:

$R^a$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;

$R^b$ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl;

$R^c$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, and aminoalkyl; and $R^d$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or, when —$XR^1$ is In certain embodiments, —$XR^1$ is selected from the group consisting of

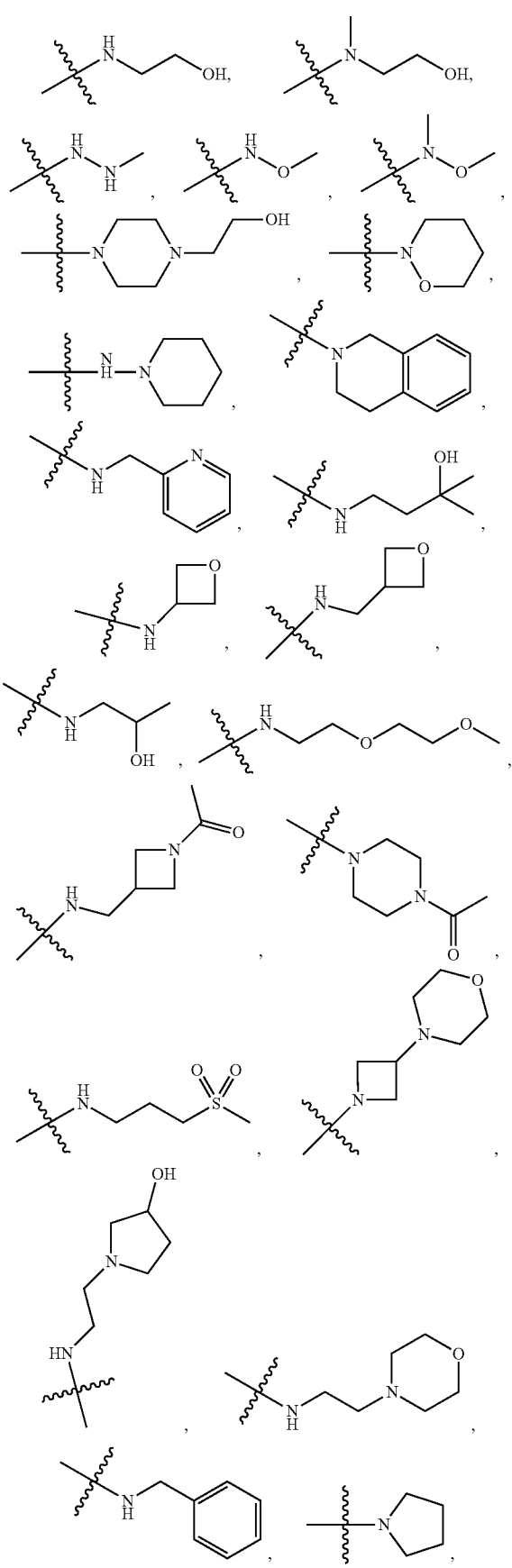
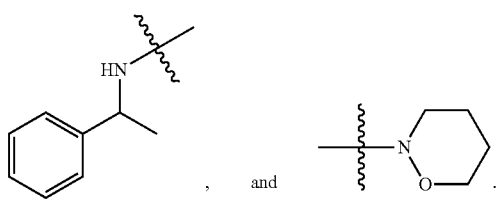
In certain embodiments, —XR[1] is selected from the group consisting of
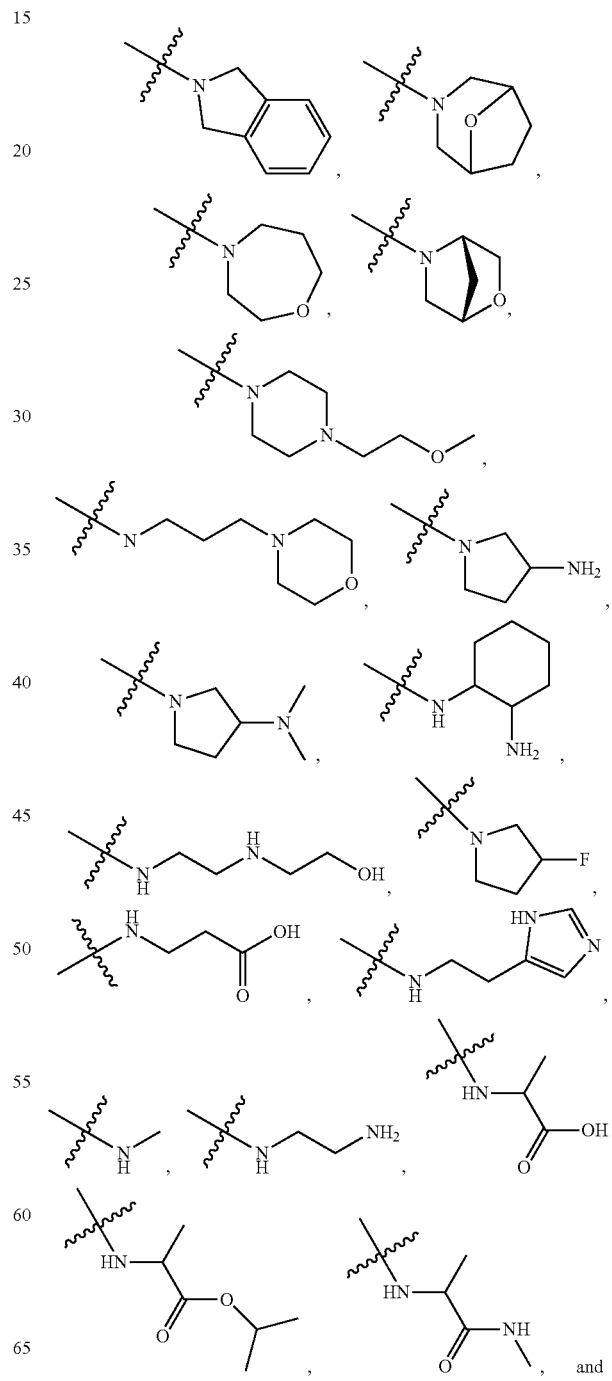

-continued

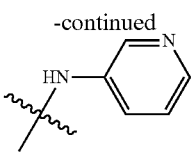

In certain embodiments, —XR¹ is selected from the group consisting of methyl, ethyl, propyl, isopropyl, propenyl,

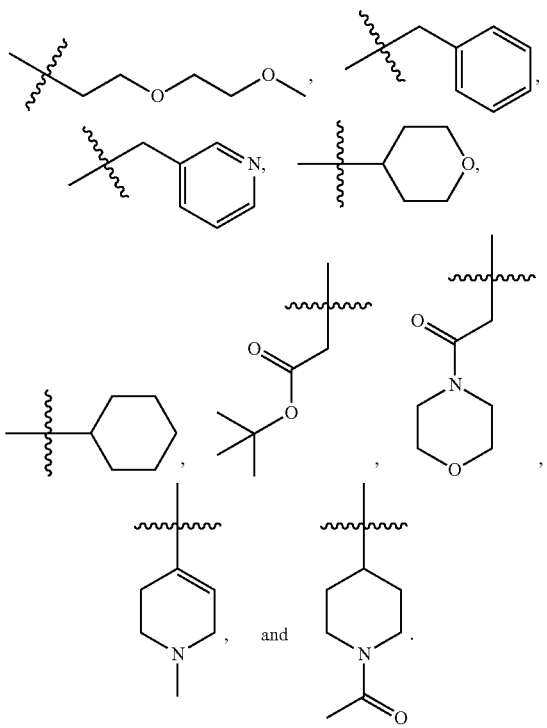

In certain embodiments, X is —O—; and R¹ is selected from the group consisting of methyl, ethyl, propyl, isopropyl, propenyl,

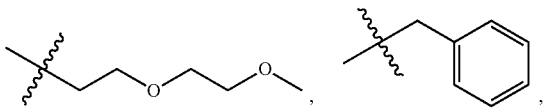

-continued

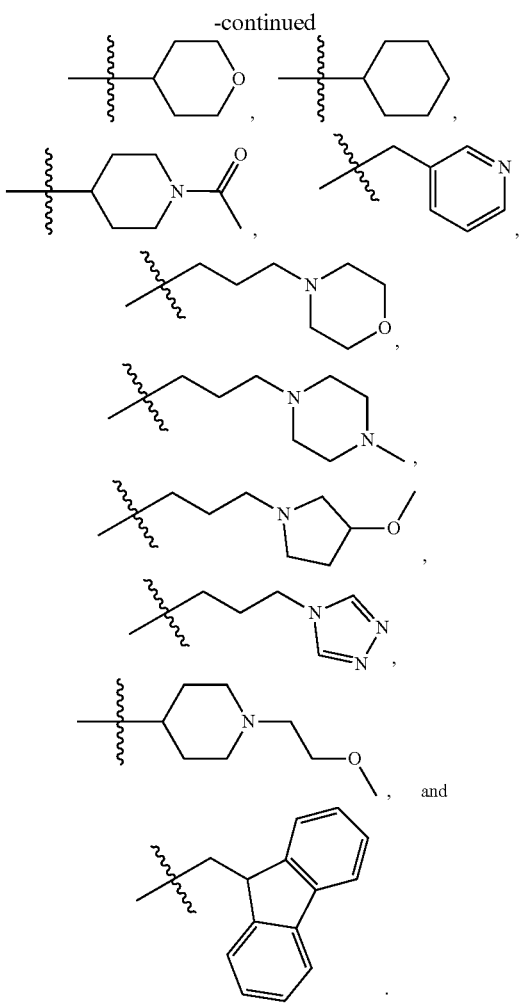

In certain embodiments, $R^5$ is hydrogen.
In certain embodiments, $R^5$ is alkyl.
In certain embodiments, $R^5$ is haloalkyl.
In certain embodiments of the compound of Formula (I), the —N(H)—C(O)—XR¹ moiety is replaced with —N(alkyl)-C(O)—XR¹.

An aspect of the invention is a compound represented by Formula (II) or a pharmaceutically acceptable salt thereof:

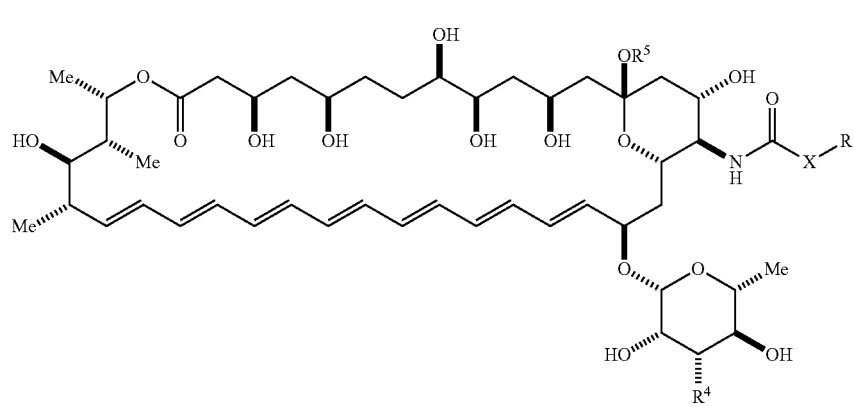

(II)

wherein, independently for each occurrence:

X is —N(R$^2$)—, —C(R$^3$)(R$^3$)—, or —O—;

R$^2$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;

R$^3$ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl;

when X is —N(R$^2$)—, R$^1$ is a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or R$^1$ and R$^2$, together with the nitrogen to which they are attached, may form a substituted or unsubstituted 3- to 10-membered heterocyclic ring, wherein said ring is monocyclic, bicyclic, tricyclic, or spirocyclic;

when X is —C(R$^3$)(R$^3$)—, R$^1$ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl; or the two instances of R$^3$, together with the carbon to which they are attached, may form a substituted or unsubstituted 3- to 10-membered aliphatic or heterocyclic ring, wherein said ring is monocyclic, bicyclic, tricyclic, or spirocyclic;

when X is —O—, R$^1$ is a substituted or unsubstituted group selected from the group consisting of alkyl, alkenyl, cycloalkyl, (cycloalkyl)alkyl, heterocyclyl, (heterocyclyl)alkyl, aryl, heteroaryl, aralkyl, heteroaralkyl, acyl, amino, amido, and aminoalkyl;

R$^4$ is secondary amino, tertiary amino, amido, azido, isonitrile, nitro, urea, isocyanate, carbamate, or guanidinyl; and R$^5$ is selected from the group consisting of hydrogen, alkyl, and haloalkyl.

In certain embodiments, R$^2$ is hydrogen.

In certain embodiments, X is —N(R$^2$)—.

In certain embodiments, X is —N(R$^2$)—, wherein R$^2$ is hydrogen.

In certain embodiments, X is —C(R$^3$)(R$^3$)—.

In certain embodiments, X is —O—.

In certain embodiments, —XR$^1$ is selected from the group consisting of —NHCH$_3$,

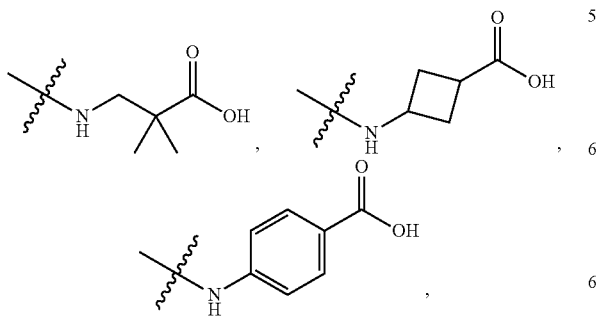

,

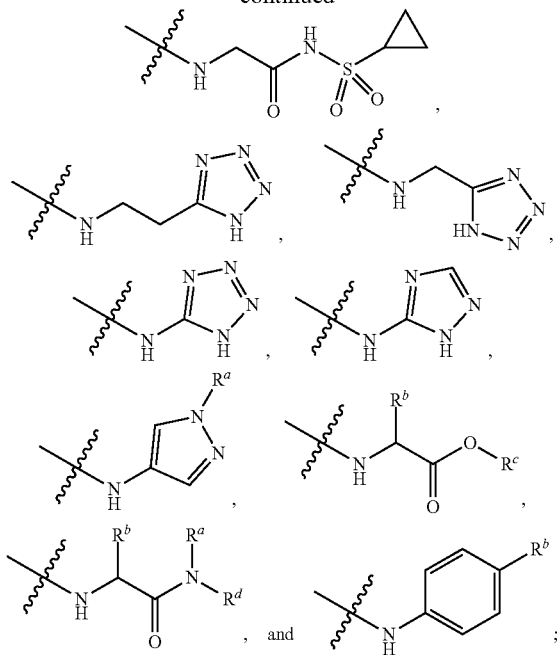

, and wherein, independently for each occurrence:

R$^a$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;

R$^b$ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl;

R$^c$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, and aminoalkyl; and R$^d$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or, when —XR$^1$ is

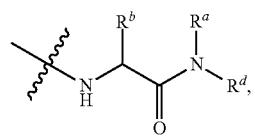

R$^a$ and R$^d$, together with the nitrogen to which they are attached, may form a substituted or unsubstituted 3- to 10-membered heterocyclic ring, wherein said ring is monocyclic, bicyclic, tricyclic, or spirocyclic.

In certain embodiments, —XR$^1$ is selected from the group consisting of

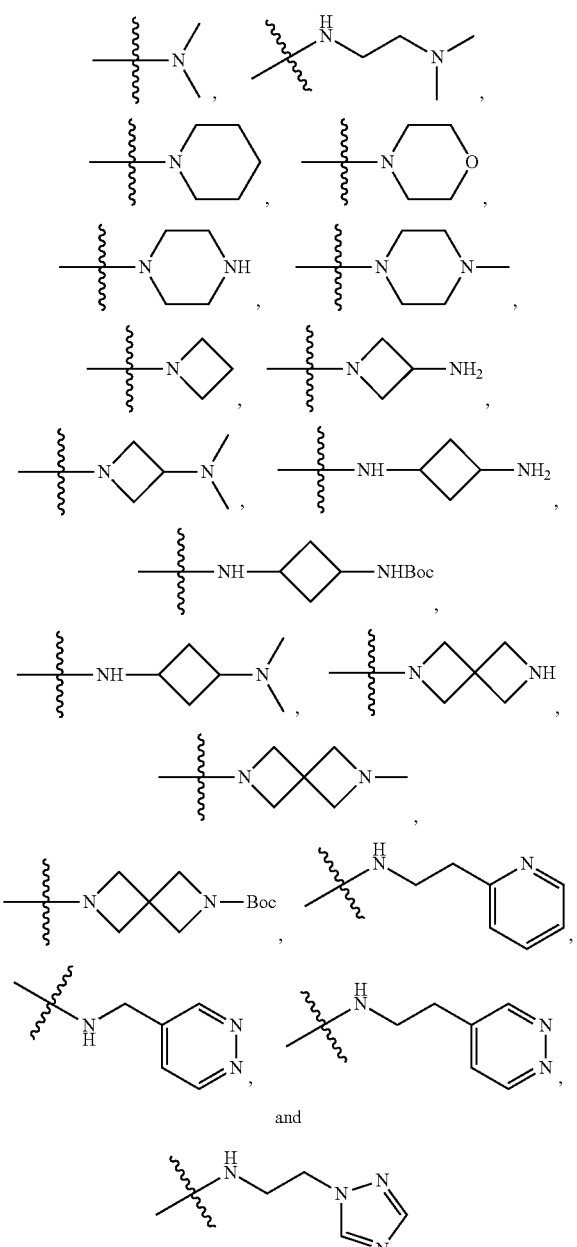
In certain embodiments, —XR[1] is selected from the group consisting of
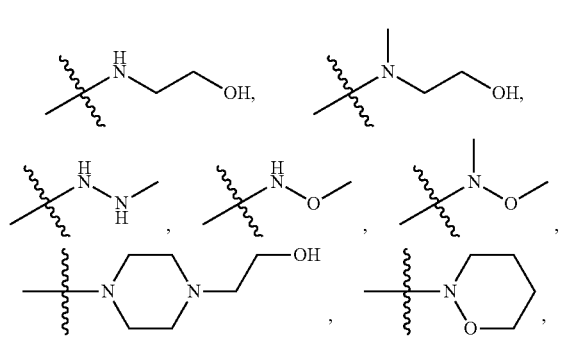
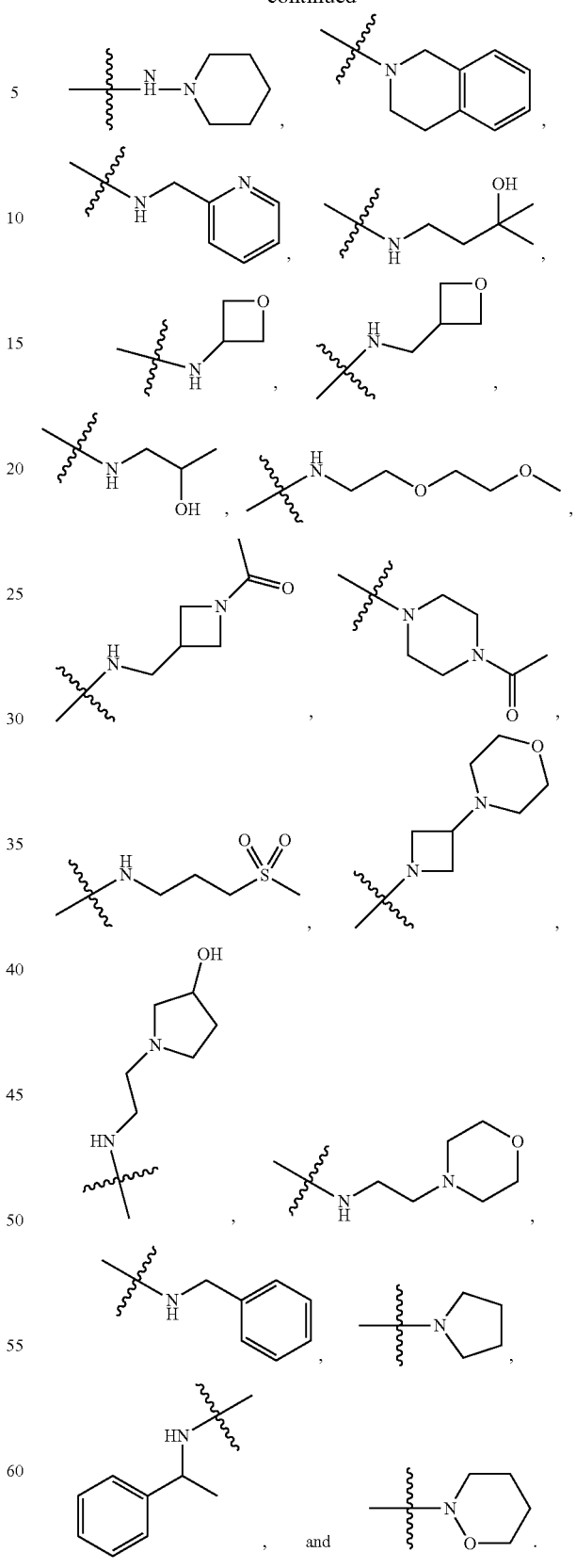
In certain embodiments, —XR[1] is selected from the group consisting of

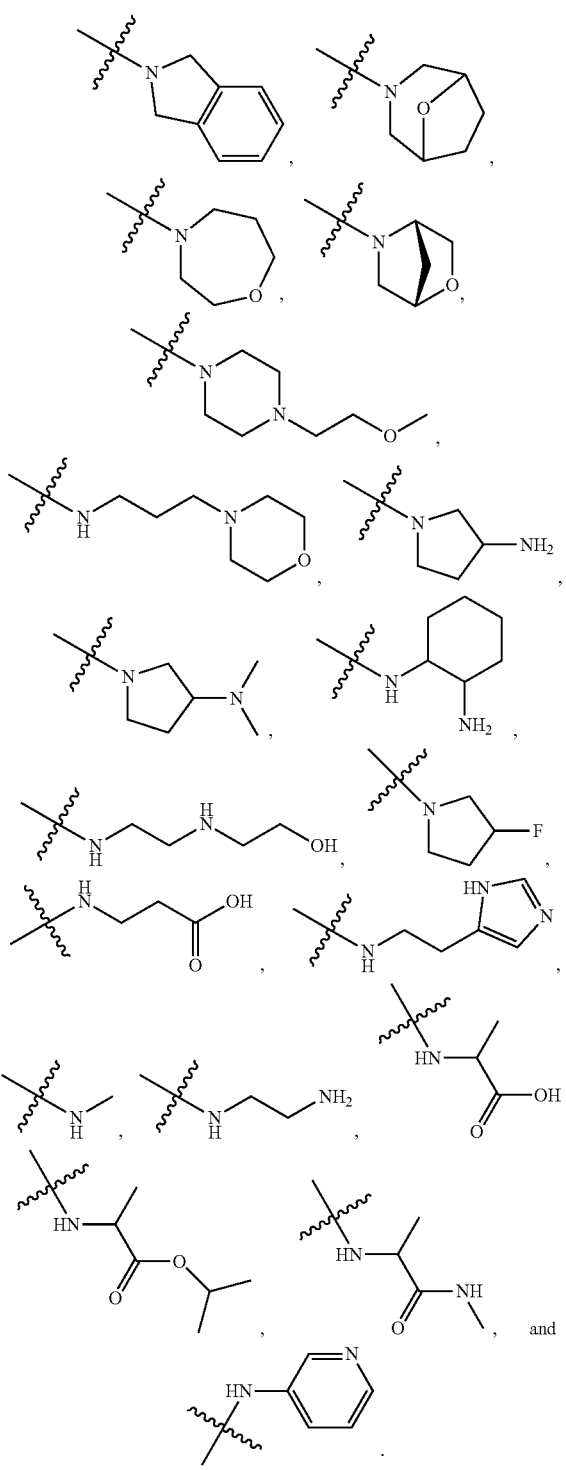
In certain embodiments, —XR[1] is selected from the group consisting of methyl, ethyl, propyl, isopropyl, propenyl,
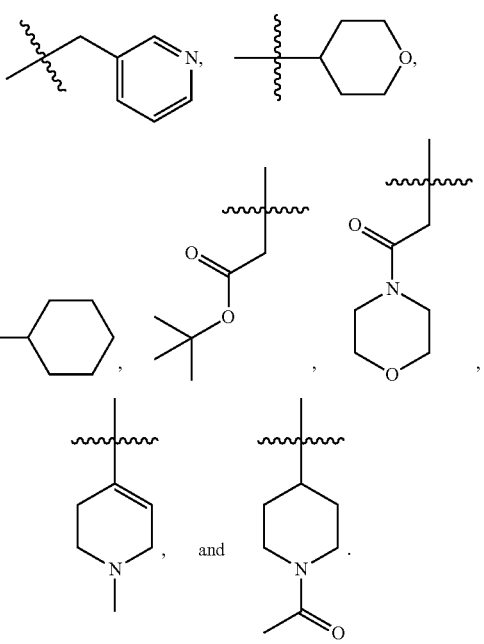
In certain embodiments, X is —O—; and R[1] is selected from the group consisting of methyl, ethyl, propyl, isopropyl, propenyl,
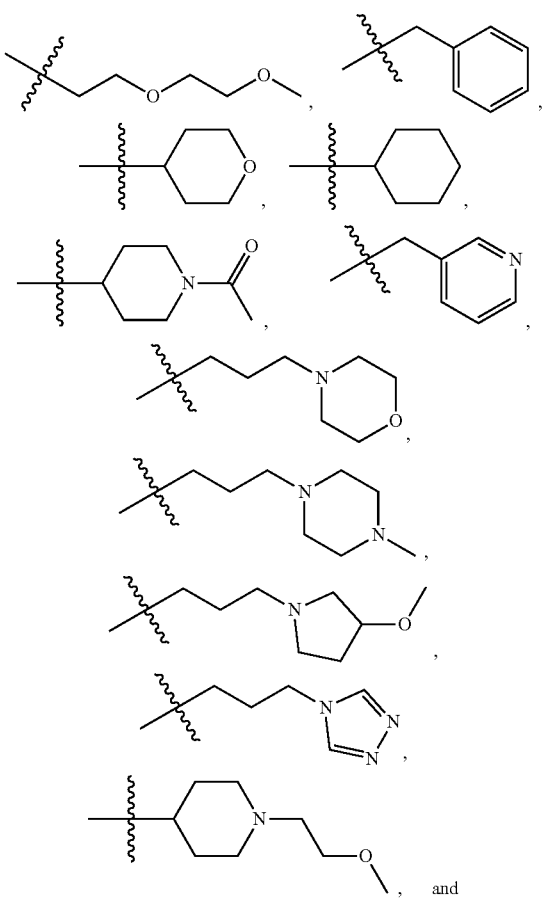
and

31

-continued

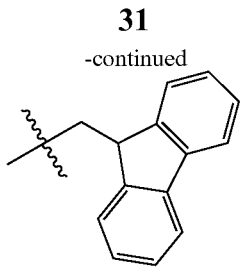

In certain embodiments, R⁴ is secondary amino.
In certain embodiments, R⁴ is tertiary amino.
In certain embodiments, R⁴ is amido.
In certain embodiments, R⁴ is azido.
In certain embodiments, R⁴ is isonitrile.
In certain embodiments, R⁴ is nitro.
In certain embodiments, R⁴ is urea.
In certain embodiments, R⁴ is isocyanate.
In certain embodiments, R⁴ is carbamate.
In certain embodiments, R⁴ is guanidinyl.
In certain embodiments, R⁴ is selected from the group consisting of

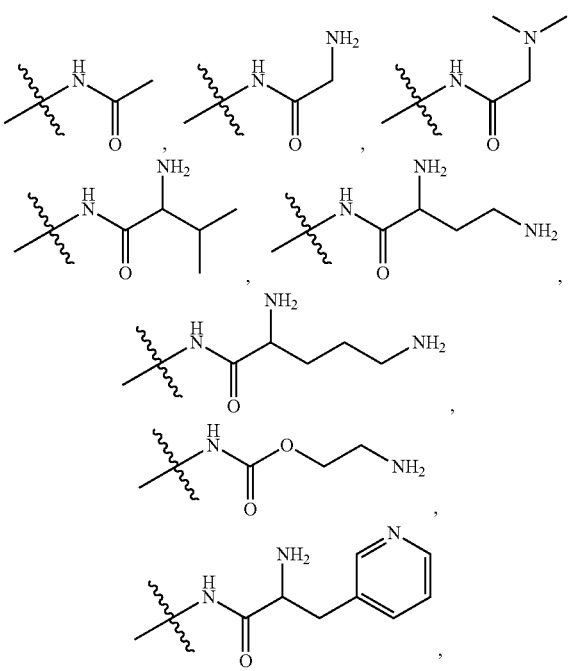

32

-continued

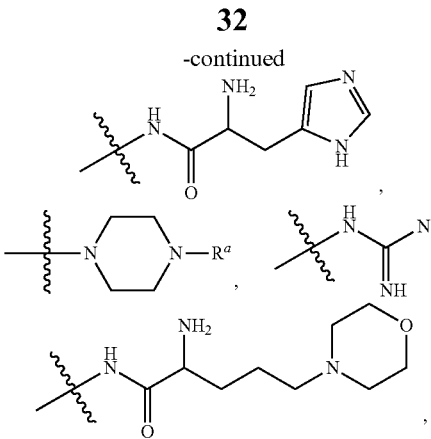

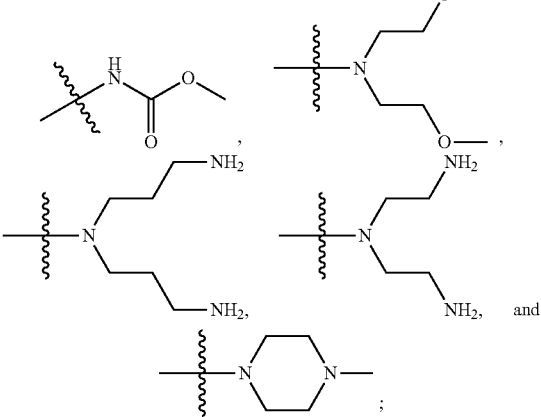

wherein $R^a$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl.

In certain embodiments, $R^5$ is hydrogen.
In certain embodiments, $R^5$ is alkyl.
In certain embodiments, $R^5$ is haloalkyl.
In certain embodiments of the compound of Formula (II), the —N(H)—C(O)—XR¹ moiety is replaced with —N(alkyl)-C(O)—XR¹.

An aspect of the invention is a compound represented by Formula (III) or a pharmaceutically acceptable salt thereof:

(III)

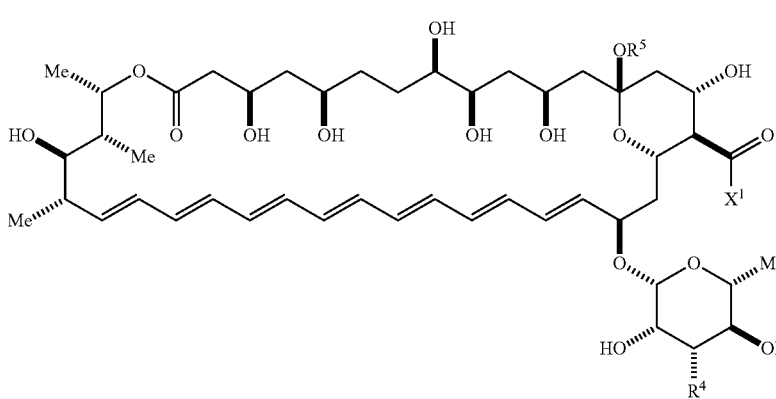

wherein, independently for each occurrence:

$X^1$ is —N($R^6$)($R^7$), —O$R^8$, or —$R^9$;

$R^6$ and $R^7$ are independently hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or, $R^6$ and $R^7$, together with the nitrogen to which they are attached, may form a substituted or unsubstituted 3- to 10-membered heterocyclic ring, wherein said ring is monocyclic, bicyclic, tricyclic, or spirocyclic;

$R^8$ is a substituted or unsubstituted group selected from the group consisting of alkyl, heteroalkyl, cycloalkyl, (cycloalkyl)alkyl, alkenyl, heterocyclyl, aryl, heteroaryl, aralkyl, heteroaralkyl, acyl, amino, amido, and aminoalkyl;

$R^9$ is hydrogen, halogen, hydroxyl, sulfhydryl, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, aminoalkyl, and alkoxyl;

$R^4$ is secondary amino, tertiary amino, amido, azido, isonitrile, nitro, urea, isocyanate, carbamate, or guanidinyl; and $R^5$ is selected from the group consisting of hydrogen, alkyl, and haloalkyl.

In certain embodiments, $R^4$ is secondary amino.
In certain embodiments, $R^4$ is tertiary amino.
In certain embodiments, $R^4$ is amido.
In certain embodiments, $R^4$ is azido.
In certain embodiments, $R^4$ is isonitrile.
In certain embodiments, $R^4$ is nitro.
In certain embodiments, $R^4$ is urea.
In certain embodiments, $R^4$ is isocyanate.
In certain embodiments, $R^4$ is carbamate.
In certain embodiments, $R^4$ is guanidinyl.
In certain embodiments, $R^4$ is selected from the group consisting of

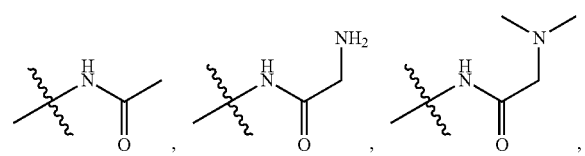

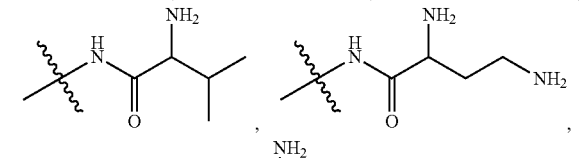

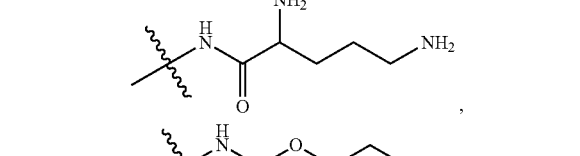

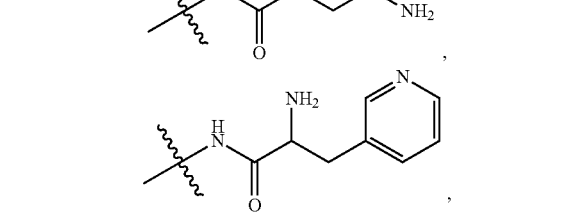

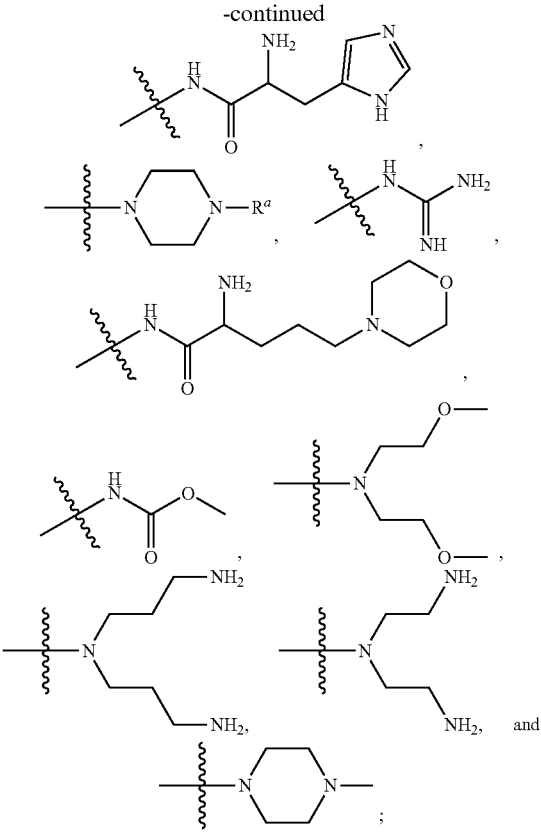

wherein $R^a$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl.

In certain embodiments, $X^1$ is —N($R^6$)($R^7$); and $R^7$ is hydrogen.

In certain embodiments, $X^1$ is selected from the group consisting of

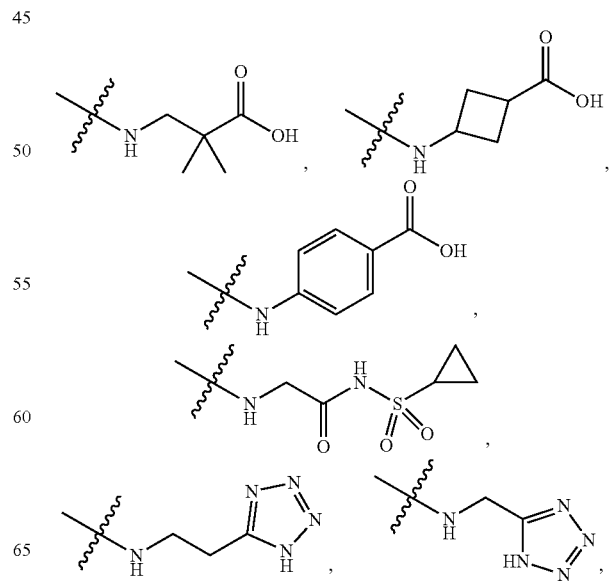

-continued

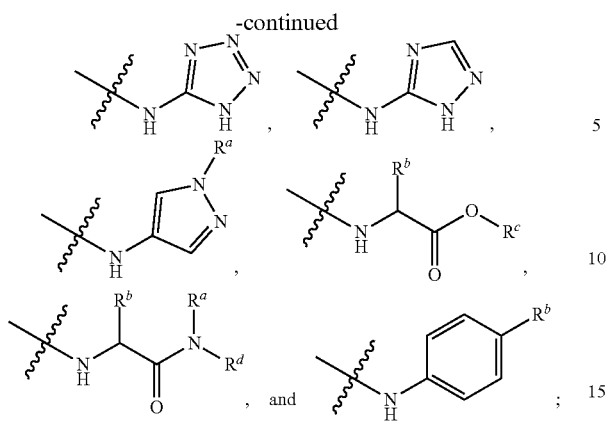

wherein, independently for each occurrence:

R$^a$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;

R$^b$ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl;

R$^c$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, and aminoalkyl; and R$^d$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or, when X$^1$ is

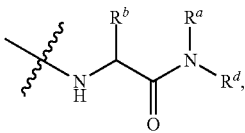

R$^a$ and R$^d$, together with the nitrogen to which they are attached, may form a substituted or unsubstituted 3- to 10-membered heterocyclic ring, wherein said ring is monocyclic, bicyclic, tricyclic, or spirocyclic.

In certain embodiments, X$^1$ is selected from the group consisting of

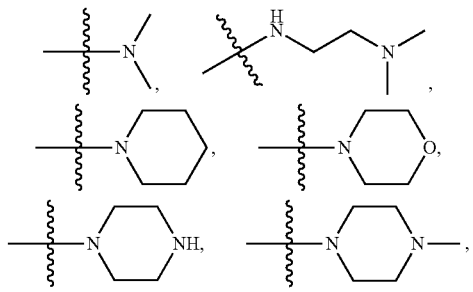

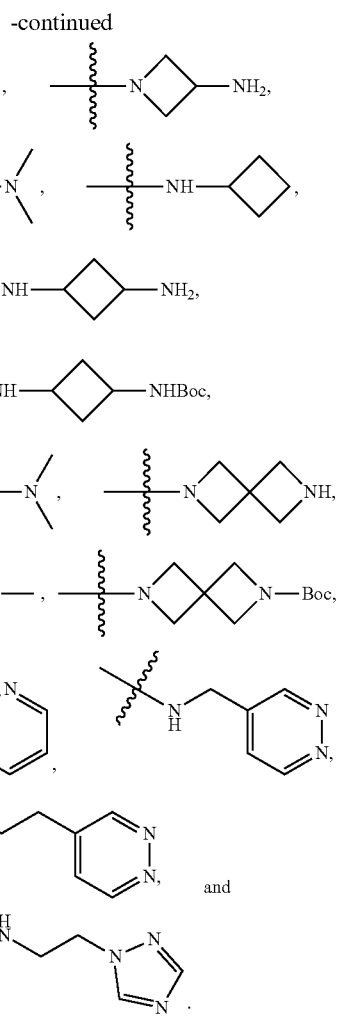

In certain embodiments, X$^1$ is selected from the group consisting of

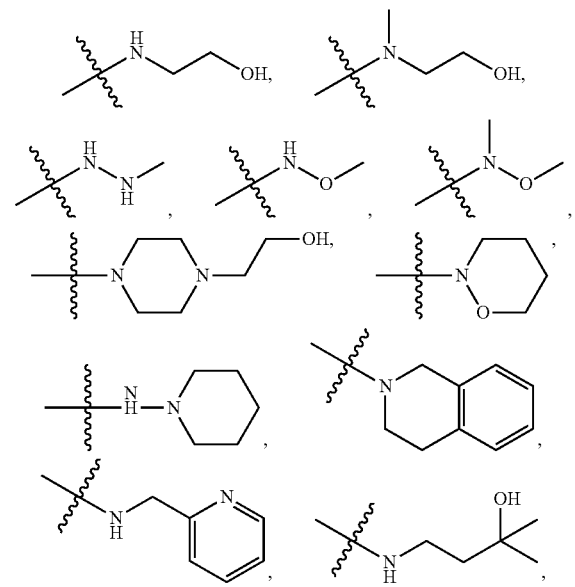

-continued
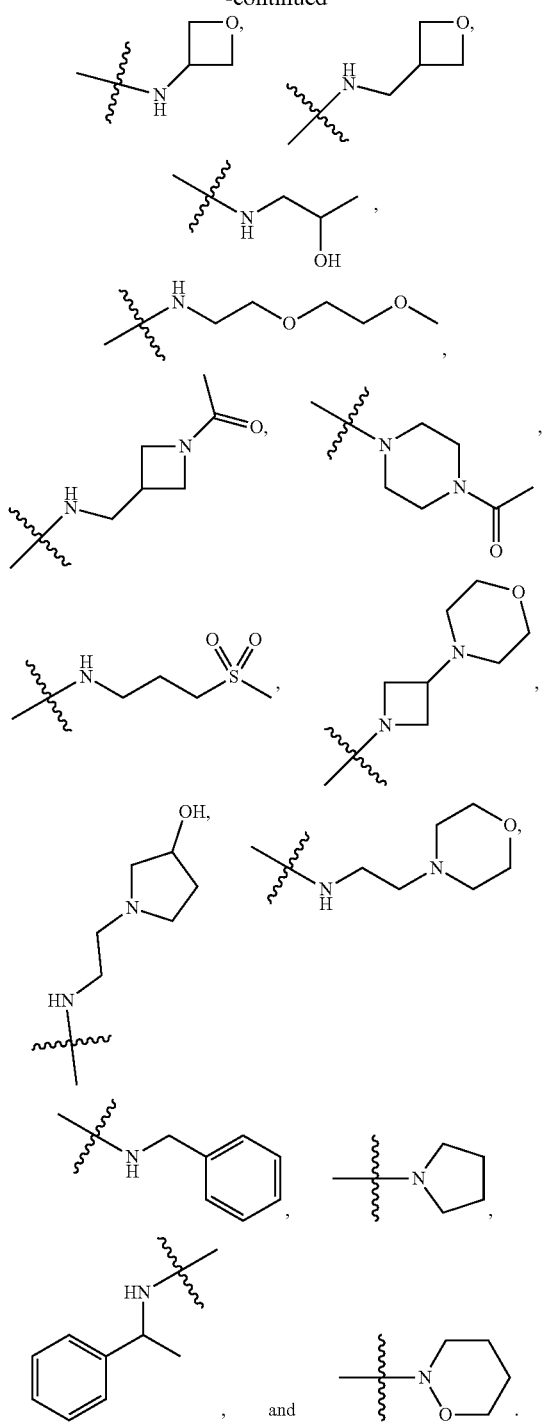
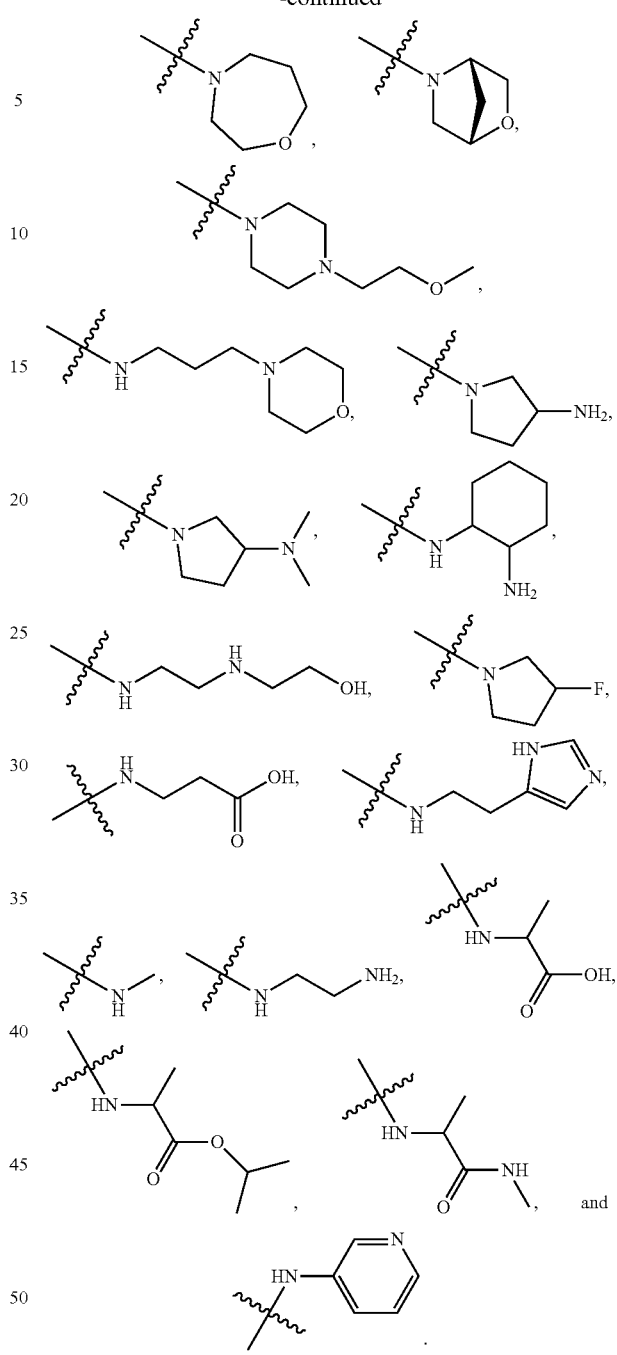
In certain embodiments, $X^1$ is selected from the group consisting of
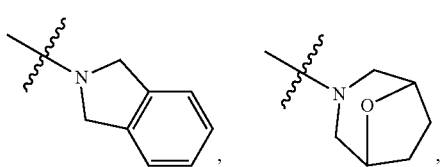
In certain embodiments, $X^1$ is selected from the group consisting of methyl, ethyl, propyl, isopropyl, propenyl,
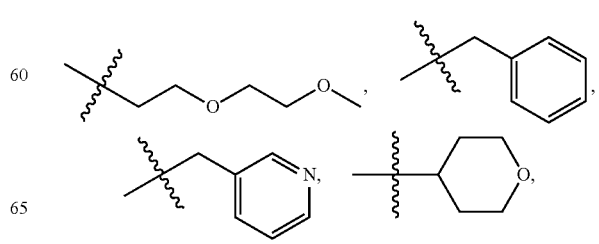

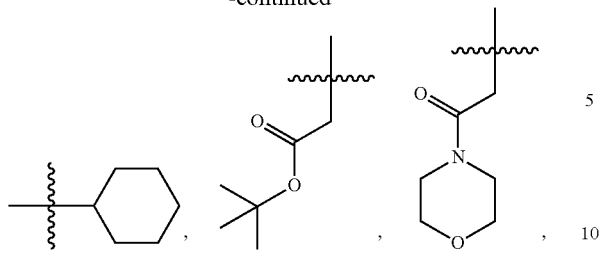

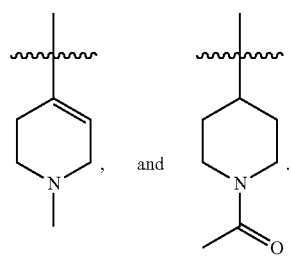

In certain embodiments, $X^1$ is —$OR^8$; and $R^8$ is selected from the group consisting of to methyl, ethyl, propyl, isopropyl, propenyl,

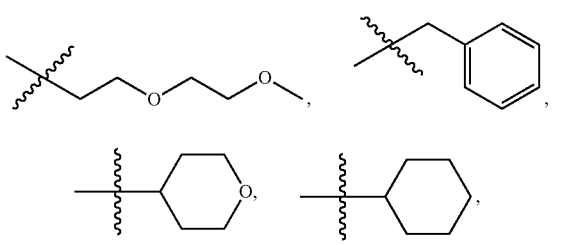

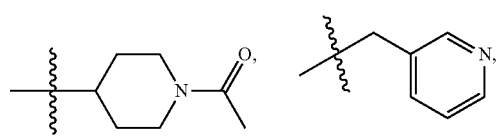

In certain embodiments, $R^5$ is hydrogen.
In certain embodiments, $R^5$ is alkyl.
In certain embodiments, $R^5$ is haloalkyl.

An aspect of the invention is a compound represented by Formula (IV) or a pharmaceutically acceptable salt thereof:

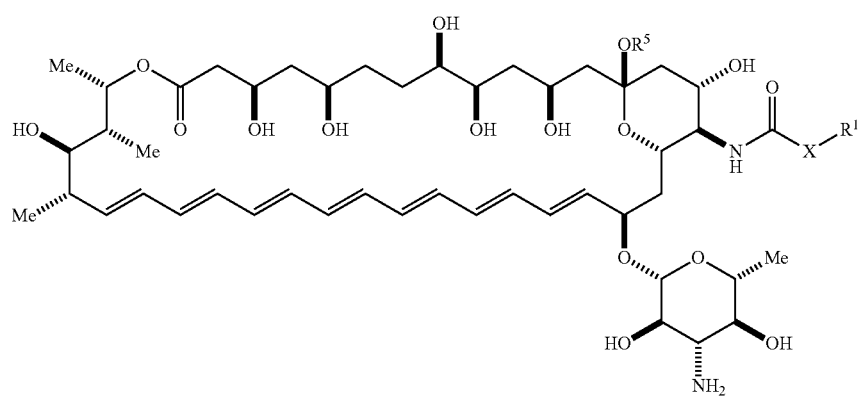

(IV)

wherein, independently for each occurrence:

X is —N(R²)—, —C(R³)(R³)—, or —O—;

R² is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;

R³ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl;

R⁵ is selected from the group consisting of hydrogen, alkyl, and haloalkyl;

when X is —N(R²)—, R¹ is a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or R¹ and R², together with the nitrogen to which they are attached, may form a substituted or unsubstituted 3- to 10-membered heterocyclic ring, wherein said ring is monocyclic, bicyclic, tricyclic, or spirocyclic;

when X is —C(R³)(R³)—, R¹ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl; or the two instances of R³, together with the carbon to which they are attached, may form a substituted or unsubstituted 3- to 10-membered aliphatic or heterocyclic ring, wherein said ring is monocyclic, bicyclic, tricyclic, or spirocyclic; and when X is —O—, R¹ is a substituted or unsubstituted group selected from the group consisting of alkyl, alkenyl, cycloalkyl, (cycloalkyl)alkyl, heterocyclyl, (heterocyclyl)alkyl, aryl, heteroaryl, aralkyl, heteroaralkyl, acyl, amino, amido, and aminoalkyl.

In certain embodiments, R² is hydrogen.
In certain embodiments, X is —N(R²)—.
In certain embodiments, X is —N(R²)—, wherein R² is hydrogen.
In certain embodiments, X is —C(R³)(R³)—.
In certain embodiments, X is —O—.
In certain embodiments, —XR¹ is selected from the group consisting of

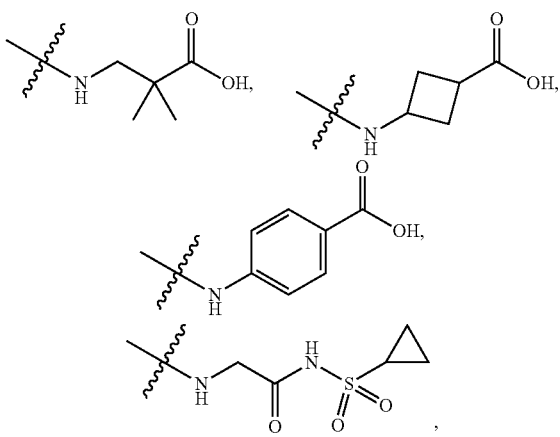

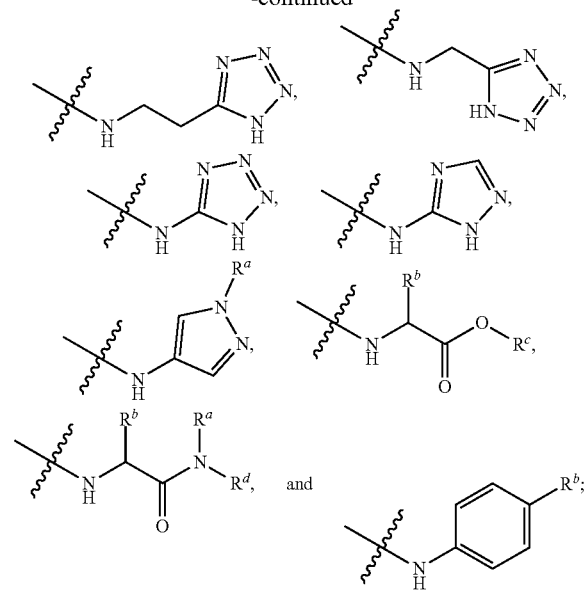

wherein, independently for each occurrence:

R^a is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;

R^b is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl;

R^c is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, and aminoalkyl; and R^d is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or, when —XR¹ is

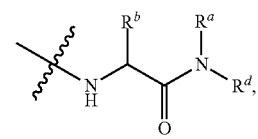

R^a and R^d, together with the nitrogen to which they are attached, may form a substituted or unsubstituted 3- to 10-membered heterocyclic ring, wherein said ring is monocyclic, bicyclic, tricyclic, or spirocyclic.

In certain embodiments, —XR¹ is selected from the group consisting of

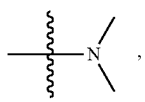

-continued
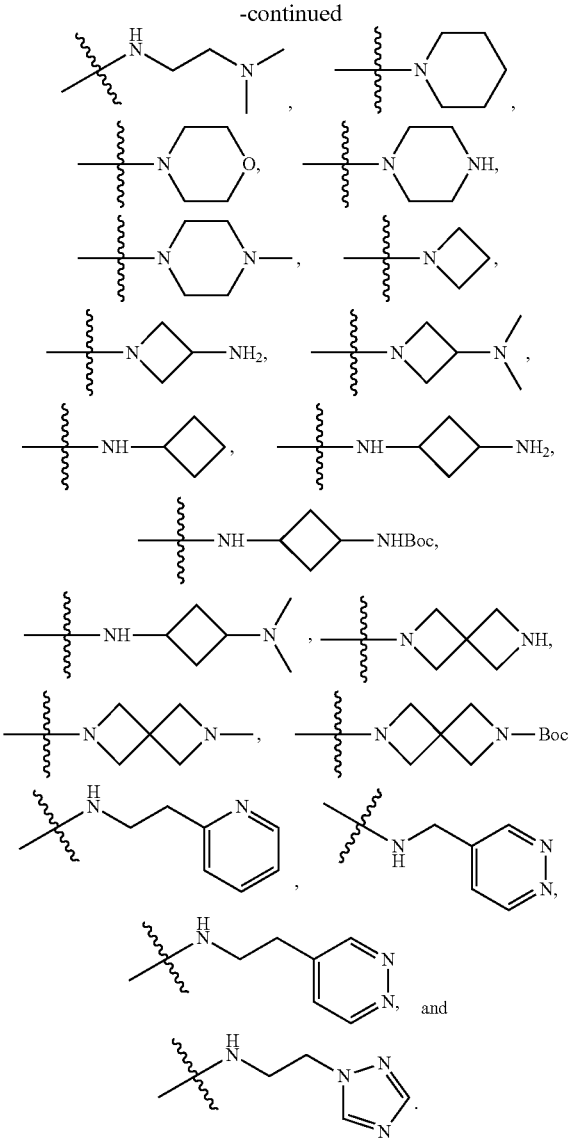
In certain embodiments, —XR¹ is selected from the group consisting of
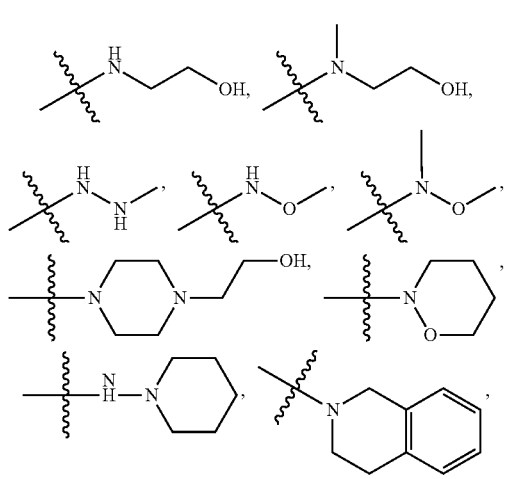
-continued
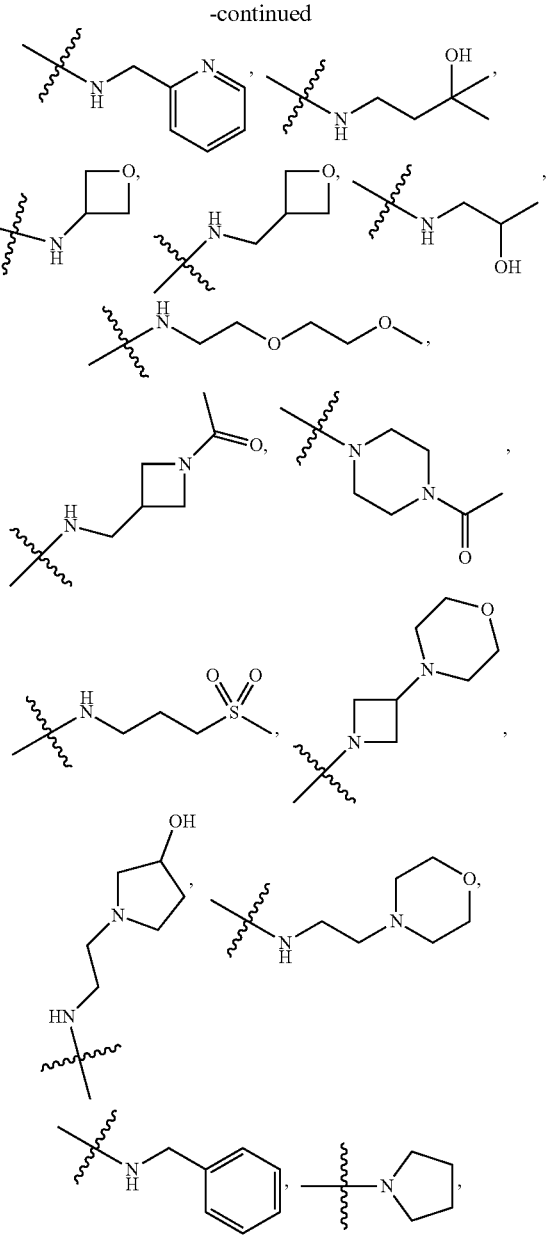
In certain embodiments, —XR¹ is selected from the group consisting of
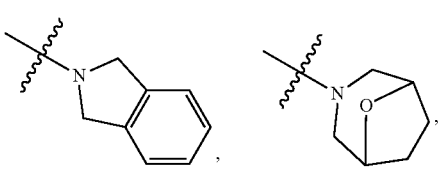

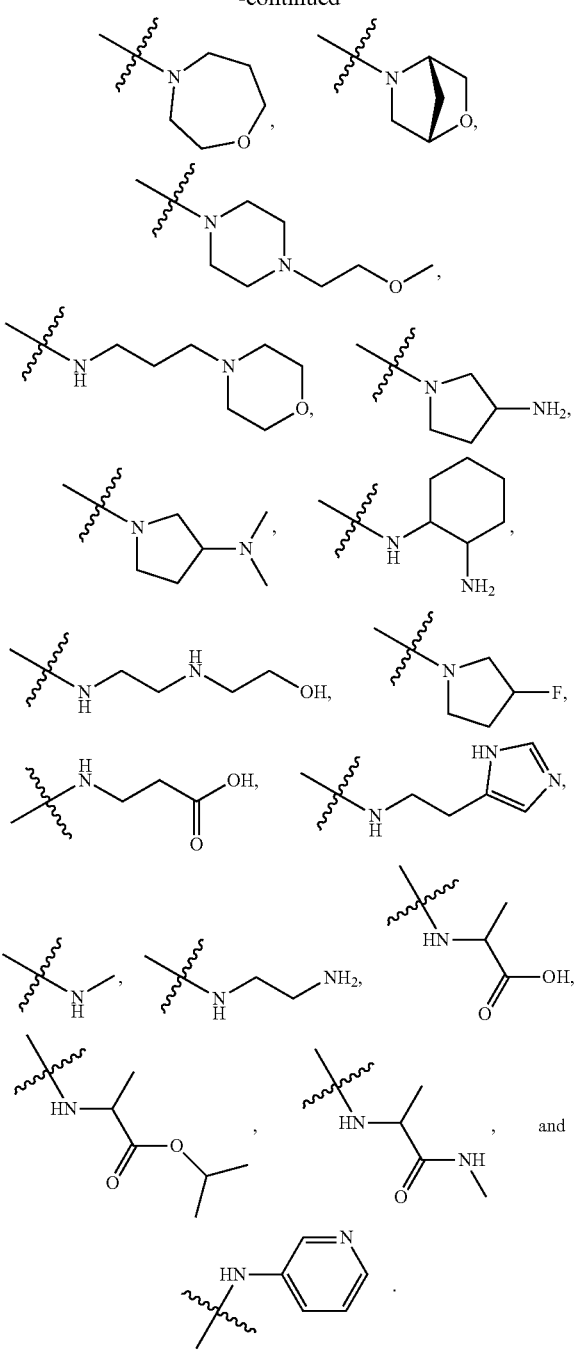
In certain embodiments, —XR[1] is selected from the group consisting of methyl, ethyl, propyl, isopropyl, propenyl,
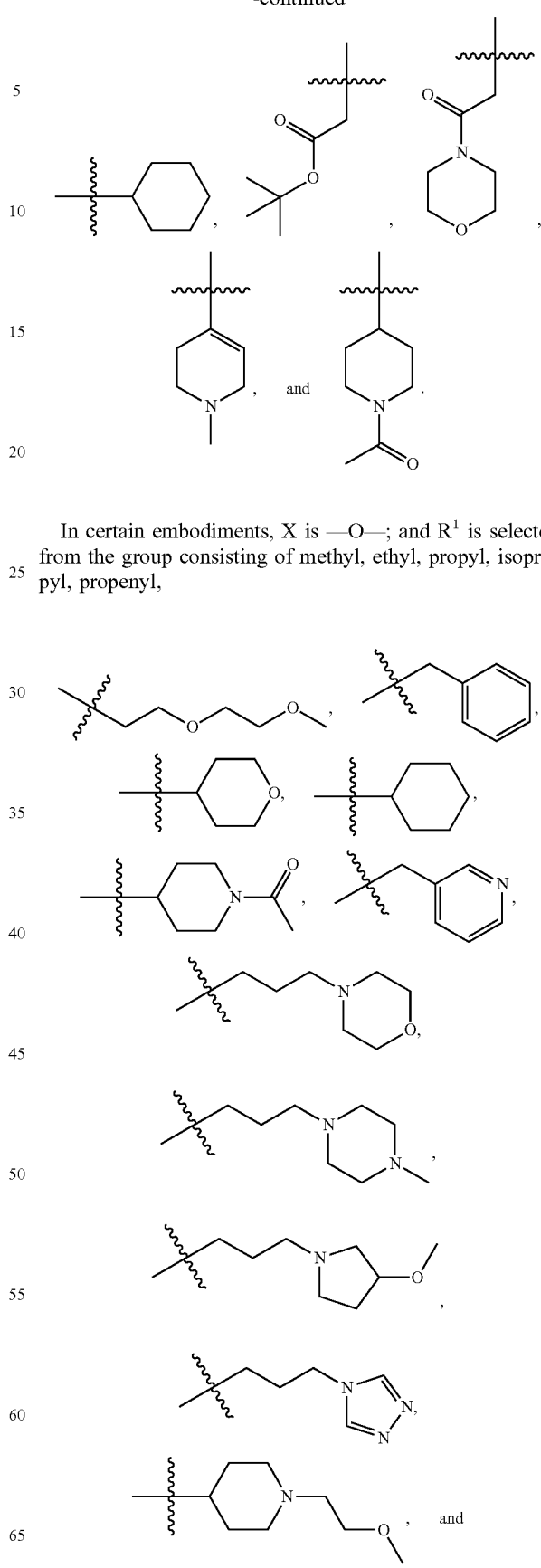
In certain embodiments, X is —O—; and R[1] is selected from the group consisting of methyl, ethyl, propyl, isopropyl, propenyl, -continued

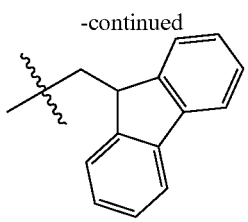

In certain embodiments, $R^5$ is hydrogen.
In certain embodiments, $R^5$ is alkyl.
In certain embodiments, $R^5$ is haloalkyl.
In certain embodiments of the compound of Formula (IV), the —N(H)—C(O)—XR$^1$ moiety is replaced with —N(alkyl)-C(O)—XR$^1$.

An aspect of the invention is a compound represented by Formula (V) or a pharmaceutically acceptable salt thereof:

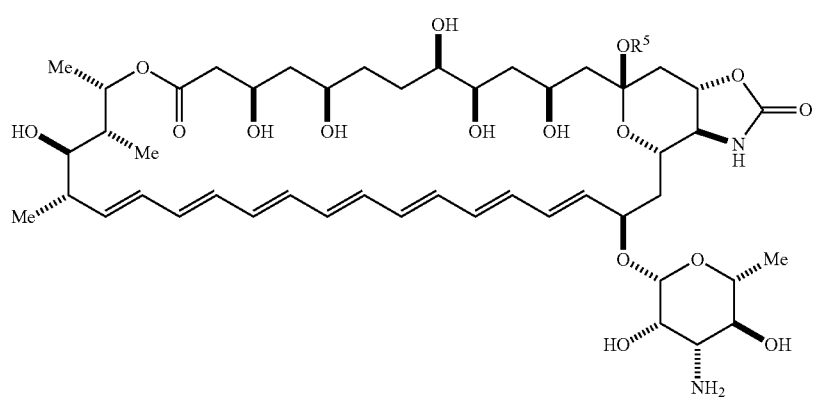

(V)

wherein $R^5$ is selected from the group consisting of hydrogen, alkyl, and haloalkyl.

In certain embodiments, $R^5$ is hydrogen.
In certain embodiments, $R^5$ is alkyl.
In certain embodiments, $R^5$ is haloalkyl.

Pharmaceutical Compositions

The invention also provides pharmaceutical compositions and methods for making same.

An aspect of the invention is a pharmaceutical composition, comprising a compound of the invention, or a pharmaceutically acceptable salt thereof, and a pharmaceutically acceptable carrier. The term "pharmaceutically acceptable carrier" means one or more compatible solid or liquid filler, diluent, or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficacy.

In certain embodiments, the pharmaceutical composition is an intravenous dosage form.

In certain embodiments, the pharmaceutical composition is an oral dosage form.

In certain embodiments, the pharmaceutical composition is a lyophilized preparation of the compound with deoxycholic acid.

In certain embodiments, the pharmaceutical composition is a lyophilized preparation of a liposome-intercalated or liposome-encapsulated active compound.

In certain embodiments, the pharmaceutical composition is a lipid complex of the compound in aqueous suspension.

In certain embodiments, the pharmaceutical composition is a cholesteryl sulfate complex of the compound.

The foregoing embodiments of pharmaceutical compositions of the invention are meant to be exemplary and are not limiting.

Also provided is a method for making such pharmaceutical compositions. The method comprises placing a compound of the invention, or a pharmaceutically acceptable salt thereof, in a pharmaceutically acceptable carrier.

Methods of the Invention

Compounds of the invention are useful for inhibiting growth of fungi and yeast, including, in particular, fungi and yeast of clinical significance as pathogens. Advantageously, the compounds of the invention have improved therapeutic indices compared to AmB, thereby providing agents with improved efficacy and reduced toxicity as compared to AmB. Compounds of the invention are useful in methods of treating fungal and yeast infections, including, in particular, systemic fungal and yeast infections. Compounds of the invention are also useful in the manufacture of medicaments for treating fungal and yeast infections, including, in particular, systemic fungal and yeast infections. The invention further provides the use of compounds of the invention for the treatment of fungal and yeast infections, including, in particular, systemic fungal and yeast infections.

An aspect of the invention is a method of treating a fungal infection, comprising administering to a subject in need thereof a therapeutically effective amount of a compound of the invention, thereby treating the fungal infection.

As used herein, "inhibit" or "inhibiting" means reduce by an objectively measurable amount or degree compared to control. In one embodiment, inhibit or inhibiting means reduce by at least a statistically significant amount compared to control. In one embodiment, inhibit or inhibiting means reduce by at least 5 percent compared to control. In various individual embodiments, inhibit or inhibiting means reduce by at least 10, 15, 20, 25, 30, 33, 40, 50, 60, 67, 70, 75, 80, 90, or 95 percent (%) compared to control.

As used herein, the terms "treat" and "treating" refer to performing an intervention that results in (a) preventing a condition or disease from occurring in a subject that may be at risk of developing or predisposed to having the condition or disease but has not yet been diagnosed as having it; (b) inhibiting a condition or disease, e.g., slowing or arresting its development; or (c) relieving or ameliorating a condition or disease, e.g., causing regression of the condition or disease. In one embodiment the terms "treating" and "treat" refer to performing an intervention that results in (a) inhibiting a condition or disease, e.g., slowing or arresting its development; or (b) relieving or ameliorating a condition or disease, e.g., causing regression of the condition or disease. For example, in one embodiment the terms "treating" and "treat" refer to performing an intervention that results in (a) inhibiting a fungal infection, e.g., slowing or arresting its development; or (b) relieving or ameliorating a fungal infection, e.g., causing regression of the fungal infection.

A "fungal infection" as used herein refers to an infection in or of a subject with a fungus as defined herein. In one embodiment the term "fungal infection" includes a yeast infection. A "yeast infection" as used herein refers to an infection in or of a subject with a yeast as defined herein.

As used herein, a "subject" refers to a living mammal. In various embodiments a subject is a non-human mammal, including, without limitation, a mouse, rat, hamster, guinea pig, rabbit, sheep, goat, cat, dog, pig, horse, cow, or non-human primate. In one embodiment a subject is a human.

As used herein, a "subject having a fungal infection" refers to a subject that exhibits at least one objective manifestation of a fungal infection. In one embodiment a subject having a fungal infection is a subject that has been diagnosed as having a fungal infection and is in need of treatment thereof. Methods of diagnosing a fungal infection are well known and need not be described here in any detail.

As used herein, a "subject having a yeast infection" refers to a subject that exhibits at least one objective manifestation of a yeast infection. In one embodiment a subject having a yeast infection is a subject that has been diagnosed as having a yeast infection and is in need of treatment thereof. Methods of diagnosing a yeast infection are well known and need not be described here in any detail.

In certain embodiments, the compound is administered systemically.

In certain embodiments, the compound is administered parenterally.

In certain embodiments, the compound is administered intravenously.

In certain embodiments, the compound is administered intraperitoneally.

In certain embodiments, the compound is administered enterally.

In certain embodiments, the compound is administered orally.

In certain embodiments, the compound is administered intraocularly.

In certain embodiments, the compound is administered topically.

Additional routes of administration of compounds of the invention are contemplated by the invention, including, without limitation, intravesicularly (urinary bladder), pulmonary, and intrathecally.

As used herein, the phrase "effective amount" refers to any amount that is sufficient to achieve a desired biological effect.

As used herein, the phrase "therapeutically effective amount" refers to an amount that is sufficient to achieve a desired therapeutic effect, e.g., to treat a fungal or yeast infection.

For any compound described herein, a therapeutically effective amount can, in general, be initially determined from in vitro studies, animal models, or both in vitro studies and animal models. In vitro methods are well known and can include determination of minimum inhibitory concentration (MIC), minimum fungicidal concentration (MFC), concentration at which growth is inhibited by 50 percent ($IC_{50}$), concentration at which growth is inhibited by 90 percent ($IC_{90}$), and the like. A therapeutically effective amount can also be determined from human data for compounds of the invention which have been tested in humans and for compounds which are known to exhibit similar pharmacological activities, such as other related active agents (e.g., AmB). Higher doses may be required for parenteral administration. The applied dose can be adjusted based on the relative bioavailability and potency of the administered compound. Adjusting the dose to achieve maximal efficacy based on the methods described herein and other methods as are well-known in the art is well within the capabilities of the ordinarily skilled artisan.

For any compound described herein, a therapeutically effective amount for use in human subjects can be initially determined from in vitro studies, animal models, or both in vitro studies and animal models. A therapeutically effective amount for use in human subjects can also be determined from human data for compounds of the invention which have been tested in humans and for compounds which are known to exhibit similar pharmacological activities, such as other related active agents (e.g., AmB). Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

Dosing and Formulation

Compounds of the invention can be combined with other therapeutic agents. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Examples of other therapeutic agents include other antifungal agents, including AmB, as well as other antibiotics, anti-viral agents, anti-inflammatory agents, immunosuppressive agents, and anti-cancer agents.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of active compounds will be, for human subjects, from about 0.01 milligrams/kg per day to 1000 milligrams/kg per day. It is expected that oral doses in the range of 0.5 to 50 milligrams/kg, in one or several administrations per day, will yield the desired results. Dosage may be adjusted appropriately to achieve desired drug levels, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

In one embodiment, intravenous administration of a compound of the invention may typically be from 0.1 mg/kg/day to 20 mg/kg/day. Intravenous dosing thus may be similar to, or advantageously, may exceed maximal tolerated doses of AmB. Intravenous dosing also may be similar to, or advantageously, may exceed maximal tolerated daily doses of AmB. Intravenous dosing also may be similar to, or advantageously, may exceed maximal tolerated cumulative doses of AmB.

Intravenous dosing also may be similar to, or advantageously, may exceed maximal recommended doses of AmB. Intravenous dosing also may be similar to, or advantageously, may exceed maximal recommended daily doses of AmB. Intravenous dosing also may be similar to, or advantageously, may exceed maximal recommended cumulative doses of AmB.

For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

Amphotericin B is commercially available in a number of formulations, including deoxycholate-based (sometimes referred to as desoxycholate-based) formulations and lipid-based (including liposomal) formulations. Amphotericin B derivative compounds of the invention similarly may be formulated, for example, and without limitation, as deoxycholate-based formulations and lipid-based (including liposomal) formulations.

For use in therapy, an effective amount of the compound of the invention can be administered to a subject by any mode that delivers the compound of the invention to the desired surface. Administering the pharmaceutical composition of the present invention may be accomplished by any means known to the skilled artisan. Routes of administration include but are not limited to oral, intravenous, intramuscular, intraperitoneal, subcutaneous, direct injection (for example, into a tumor or abscess), mucosal, pulmonary (e.g., inhalation), and topical.

For intravenous and other parenteral routes of administration, the compounds of the invention generally may be formulated similarly to AmB. For example, a compound of the invention can be formulated as a lyophilized preparation with deoxycholic acid, as a lyophilized preparation of liposome-intercalated or -encapsulated active compound, as a lipid complex in aqueous suspension, or as a cholesteryl sulfate complex. Lyophilized formulations are generally reconstituted in suitable aqueous solution, e.g., in sterile water or saline, shortly prior to administration.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4: 185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, ca-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5): 143-146 (1989) (endothelin-1); Hubbard et al., *Annal Int Med* 3:206-212 (1989) ($\alpha$1-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (μm), most preferably 0.5 to 5 μm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described above, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally at least one additional therapeutic agent included in a pharmaceutically acceptable carrier.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

Having now described the present invention in detail, the same will be more clearly understood by reference to the following examples, which are included herewith for purposes of illustration only and are not intended to be limiting of the invention.

EXAMPLES
Example 1. $C_{15}$-$C_{16}$ Oxazolidinone 1
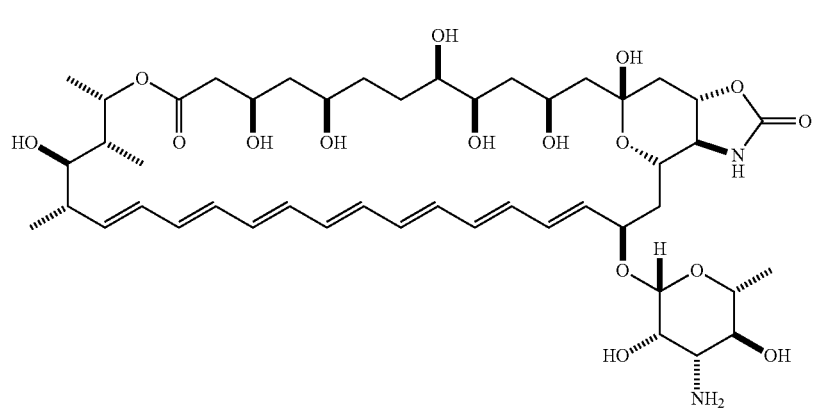
1
Scheme 1: Preparation of Compound 1
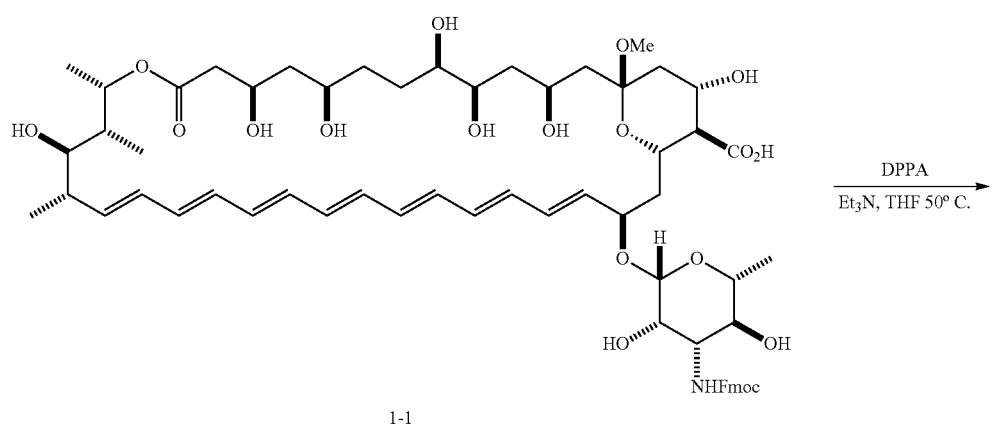
1-1
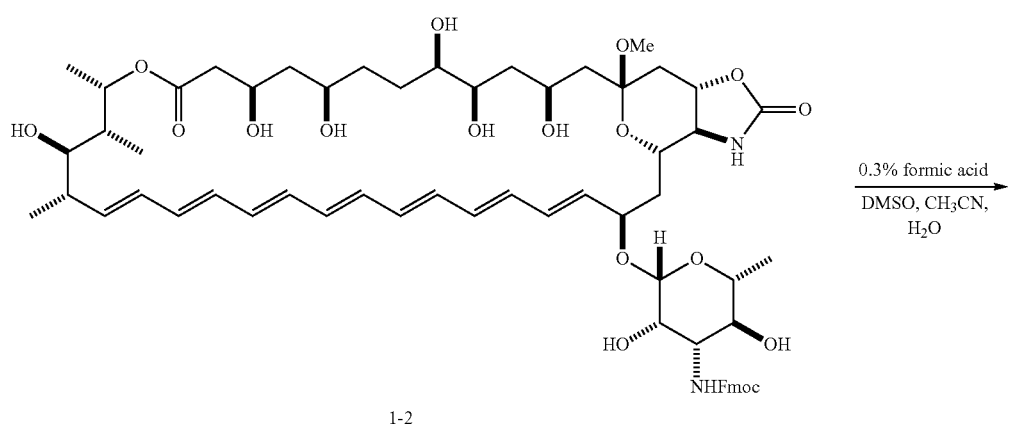
1-2

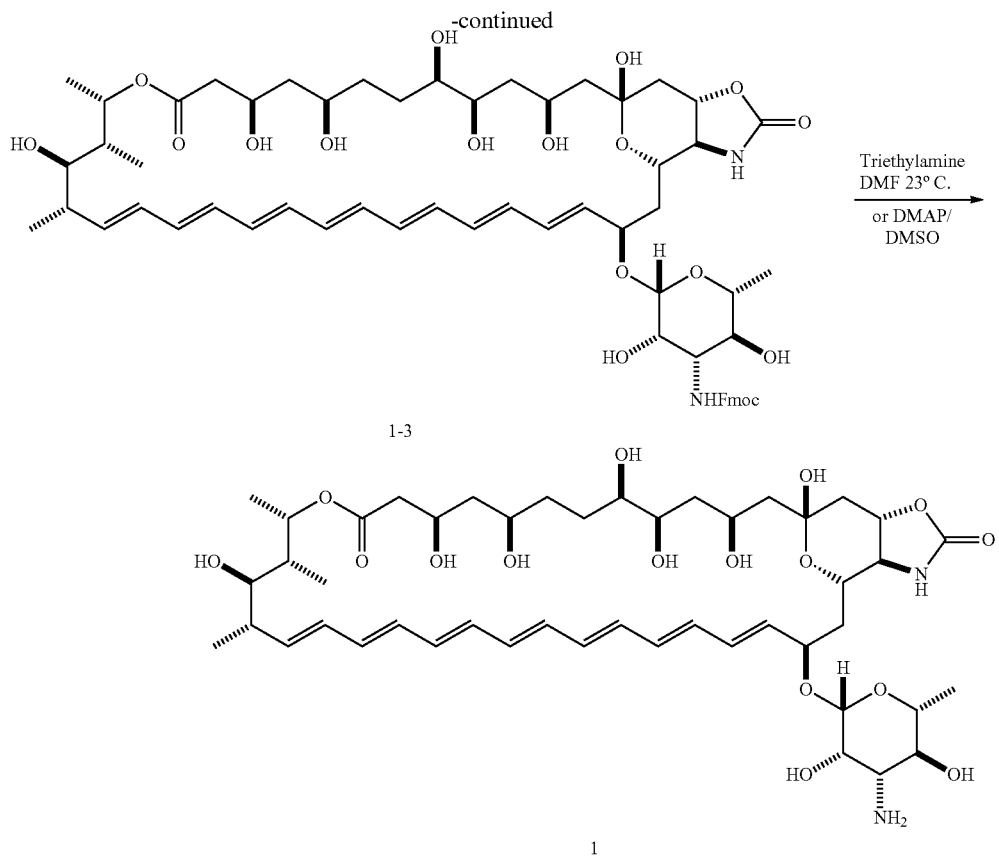

Preparation of 1-1: Step 1: A 2 L round-bottom flask was charged with Amphotericin B (Chem-Impex International) (I) (50 g, ca. 54 mmol). A mixture of DMF/MeOH (900 mL/450 mL) was added, followed by pyridine (25 mL) and FMOC-OSu (27.4 g, 81.3 mmol). The mixture was stirred at RT for 12 h and then poured into ether (5 L). The yellow precipitate was collected by filtration in a fritted glass funnel. It was then washed with more ether (4 L) and dried under high vacuum (covered with aluminum foil to prevent exposure to light) overnight. The yellow solid (64 g, >100% yield) thus obtained was used in the next step without further purification. LCMS: Observed mass 744 m/z, The [M+H]$^+$ ion was not observed.

Step 2: A 2 L round-bottom flask was charged with FMOC-protected Amphotericin B (64 g). A mixture of THF/MeOH (700 mL/700 mL) was added. The mixture was cooled in an ice/water bath and stirred under $N_2$ for 30 min. Camphor-10-sulfonic acid (CSA) (3.8 g) was added in one portion. The mixture was stirred at 0° C. for 2 h. Triethylamine (8 mL) was then added. The mixture was concentrated to approximately half its original volume and then poured into a mixture of hexanes/ether (2 L/2 L). The mixture was stirred at RT for 15 min and the yellow precipitate was collected by filtration using a fritted glass funnel. The solid was washed with more ether (ca. 500 mL) and dried under high vacuum (covered with aluminum foil to prevent exposure to light) for 2 h. The yellow solid thus obtained (68 g, >100% yield) was used in the next step without further purification. LCMS, Observed mass 742.7 m/z, the [M+H]$^+$ ion was not observed.

Preparation of 1-2: A 1 L round-bottom flask was charged with FMOC-protected ketal of amphotericin B 1-1 (68 g, ca. 55 mmol). Anhydrous THF (500 mL) was added and the suspension was stirred at RT for 10 min. Triethylamine (20 mL, 143.5 mmol) was then added. The mixture was stirred at RT for a further 15 min. Diphenylphosphoryl azide (16 mL, 68.6 mmol) was added in four equal portions at 3 minute intervals via syringe. The mixture was then heated to 50° C. and stirred for 2 hours. The reaction was cooled to room temperature and then poured into MTBE (1 L). The yellow precipitate was collected by filtration using a fritted glass funnel and then mixed with silica gel (ca. 100 g) and treated with DCM/MeOH (50 mL/5 mL). The slurry was concentrated, loaded onto a silica gel column (10 cm×48 cm) and purified using a linear gradient of 0-10% MeOH/DCM collecting 50 mL fractions. Pure fractions ($R_f$=0.5 on TLC, 10% MeOH/$CH_2Cl_2$) were combined and concentrated in vacuo to afford 1-2 as a yellow/orange solid (19.5 g, 16.86 mmol, 30.6% yield).

Preparation of 1-3: Compound 1-2 (300 milligrams) was dissolved in THF and treated with 16% formic acid in water. The solution was heated at 50° C. for 2 h. Evaporation of the solvent and purification by reverse-phase HPLC provided 1-3 (23 milligrams) (LCMS, 1166.1, M+Na).

Preparation of 1: Treatment of 1-3 with 2 equivalents of DMAP in DMSO at RT for 2 h or trimethylamine in DMF at RT for 12 h, followed by purification by RP-HPLC and lyophilization, provides the target compound 1.

Example 2. C16 Ureas 2
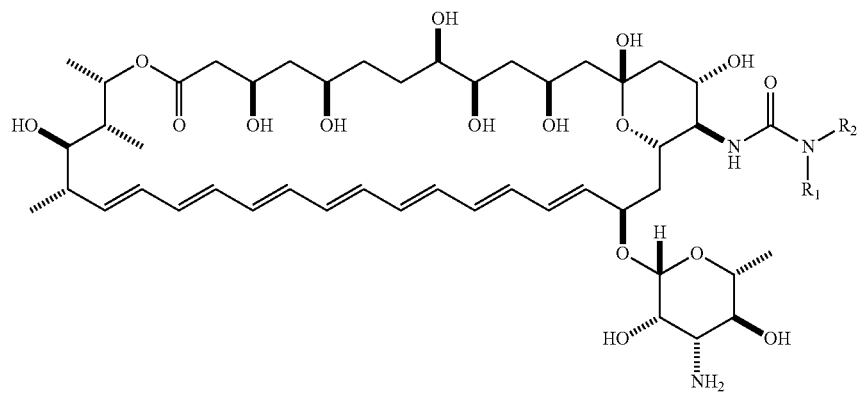
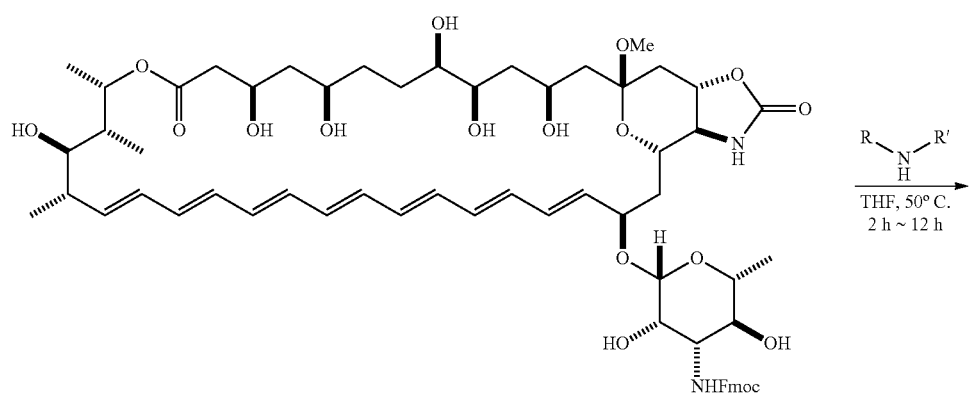
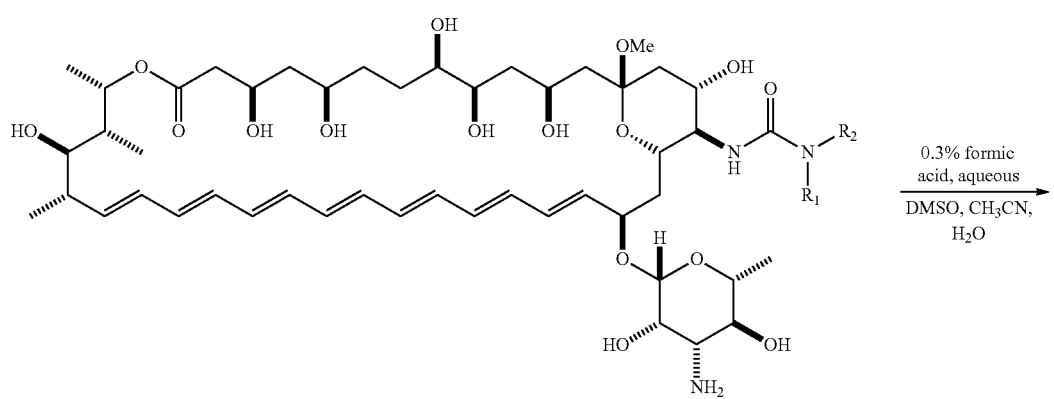

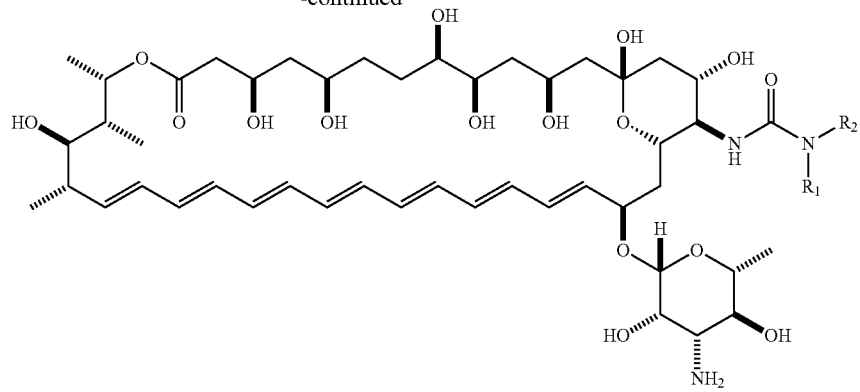

2

Compounds 2 can also be prepared according to the method described in Scheme 2, route 2. Isocyanate 3-2, prepared as described below, is treated with an amine (5-50 equivalents) in THF (0.1-0.6 M) at temperatures ranging from 23° C. to 80° C. Removal of the silyl groups with HF/pyridine and deketalization/purification with 0.3% formic acid in DMSO followed by purification in $H_2O/CH_3CN$ mixtures using 0.3% formic acid as a modifier provides the target ureas.

Scheme 2: Preparation of Ureas 2
Route 2:

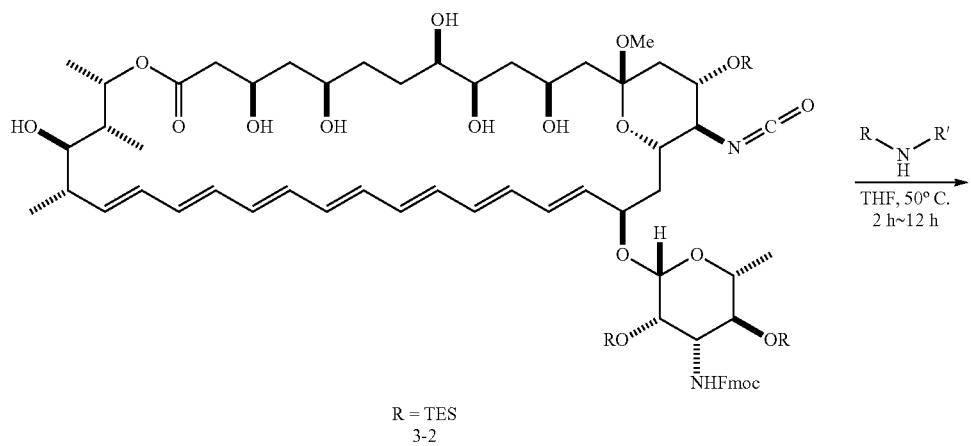

R = TES
3-2

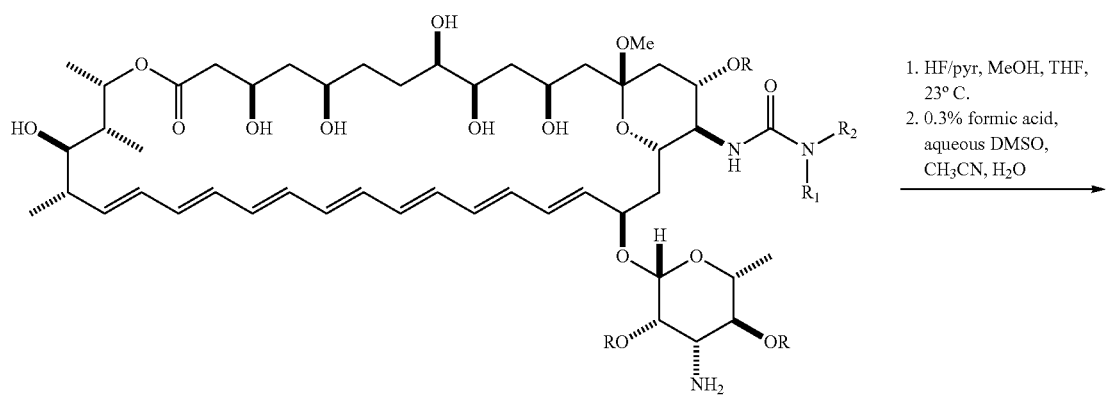

2-3

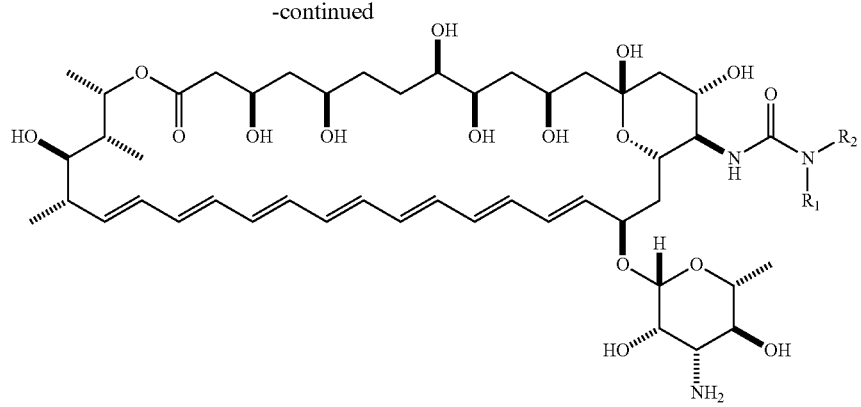
2
Specific Compounds 2
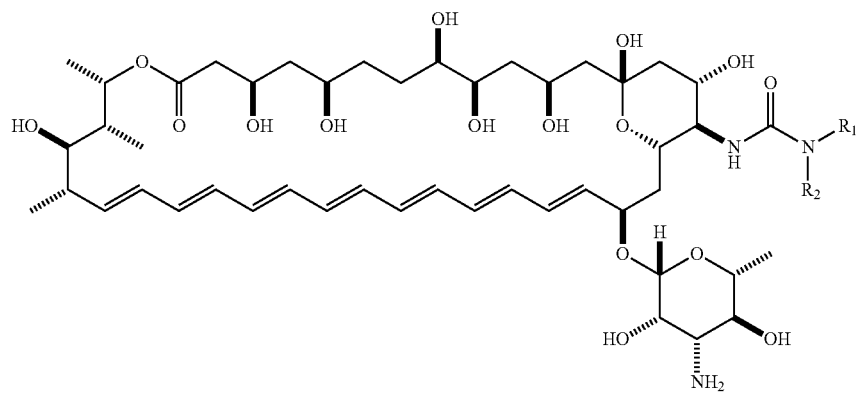
where H—NR₁R₂ is defined in Table 1:
TABLE 1
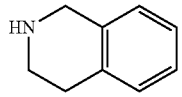 A
 B
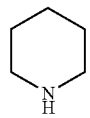 C
 D
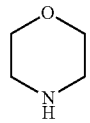 E
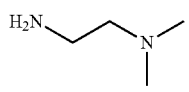 F
TABLE 1-continued
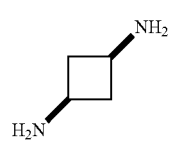 G
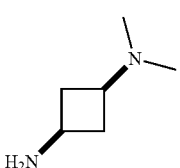 H
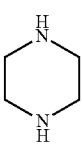 I
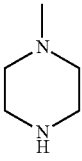 J TABLE 1-continued
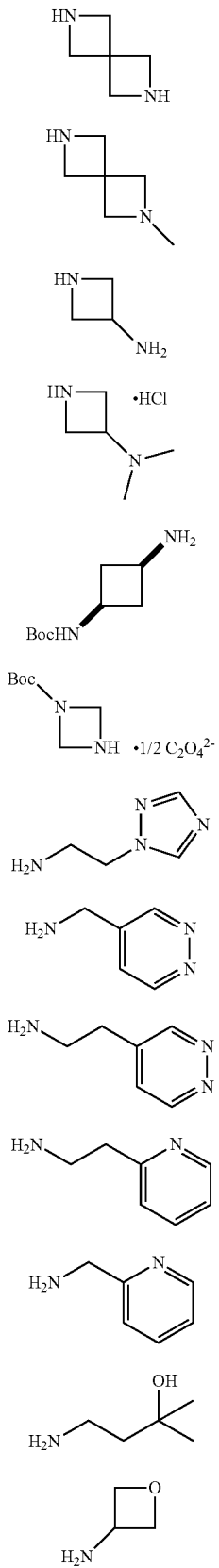
| | |
|---|---|
| | K |
| | L |
| | M |
| | N |
| | O |
| | P |
| | Q |
| | R |
| | S |
| | T |
| | U |
| | V |
| | W |
TABLE 1-continued
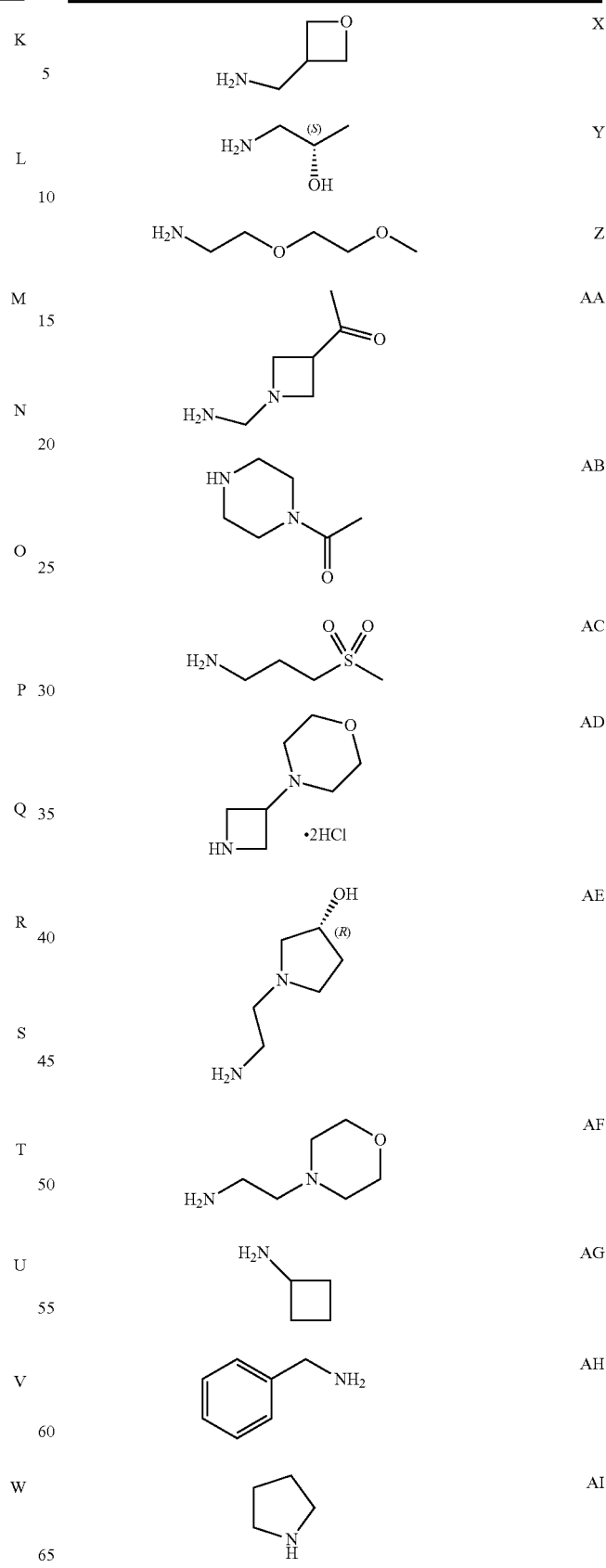
| | |
|---|---|
| | X |
| | Y |
| | Z |
| | AA |
| | AB |
| | AC |
| | AD |
| | AE |
| | AF |
| | AG |
| | AH |
| | AI |

TABLE 1-continued
| Structure | Label |
|---|---|
| 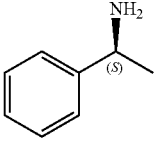 | AJ |
| 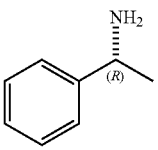 | AK |
| 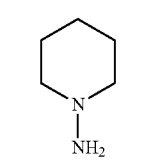 | AL |
| 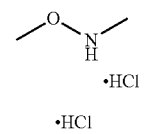 | AM |
| 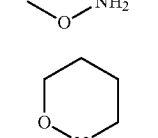 | AN |
| 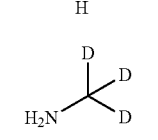 | AO |
| 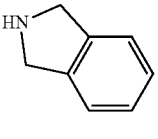 | AP |
| 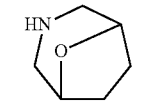 | AQ |
| 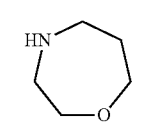 | AR |
| 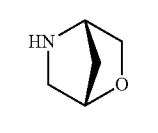 | AS |
| 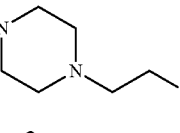 | AT |
| 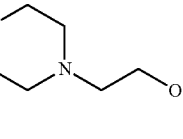 | AU |
| 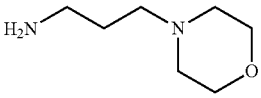 | AV |
|  | AW |
| 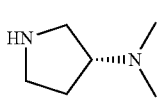 | AX |
| 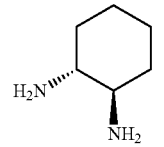 | AY |
| 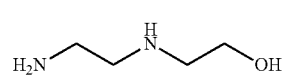 | AZ |
| 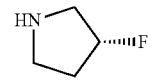 | BA |
| 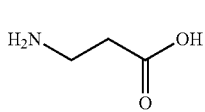 | BB |
| 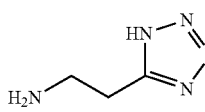 | BC |
| 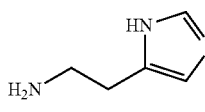 | BD |
| 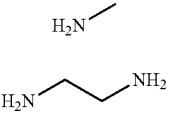 | BE |
|  | BF |
| 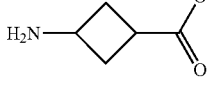 | BG |
| 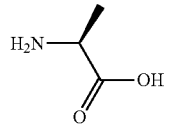 | BH |
| 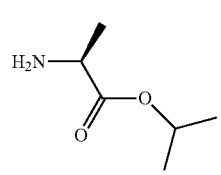 | BI |
|  | BJ |

TABLE 1-continued
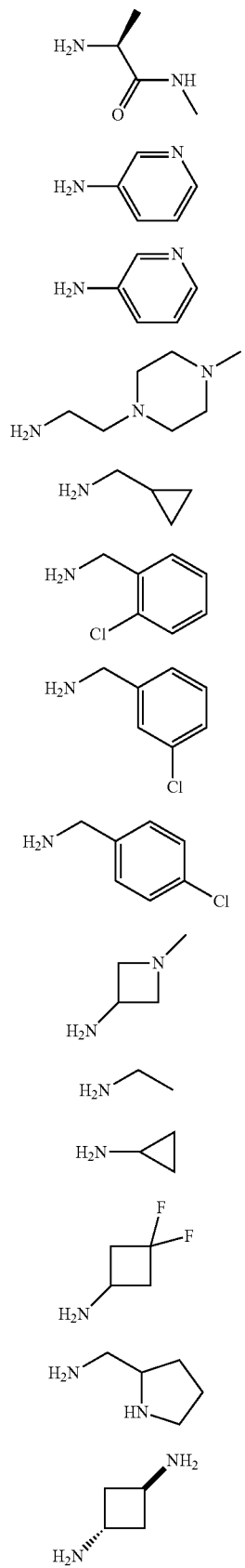
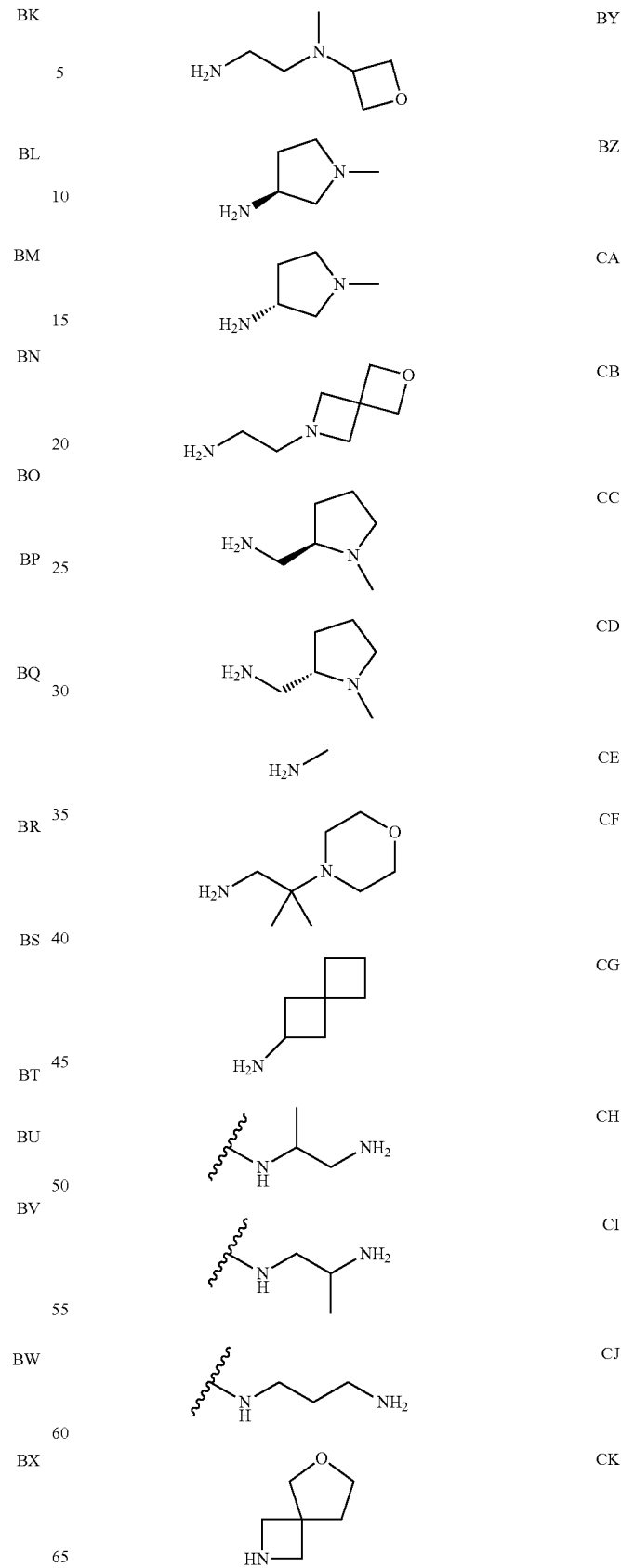

TABLE 1-continued

| ID | Structure |
|---|---|
| CL | piperidine-4-carboxylic acid (N-linked) |
| CM | H₂N-CH₂-cyclobutyl |
| CN | H₂N-CH(CH₃)₂ (isopropylamine) |
| CO | H₂N-CH₂-CH(CH₃)₂ (isobutylamine) |
| CP | H₂N-cyclohexyl |
| CQ | H₂N-CH₂CH₂-N(piperazine)-N-phenyl |
| CR | H₂N-cyclopentyl |
| CS | 4-(1H-tetrazol-5-yl)piperidine (N-linked) |
| CT | H₂N-CH₂-C₆H₄-C(O)OH (4-aminomethylbenzoic acid) |
| CU | H₂N-CD₃ |

Example 3. Preparation of Compound 2-I

Preparation of 2-2: To a solution of 1-2 (Example 1; 350 mg, 302.4 µmol, 1.00 eq.) in THF (16 mL) was added piperazine (93 mg, 1.08 mmol, 3.57 eq.) at 15° C. The mixture was stirred at 50° C. for 2 h under Ar$_2$. A yellow precipitate formed, and HPLC showed that 1-2 was consumed. The mixture was poured into MTBE (350 mL), and the solid was collected by filtration to provide crude 2-2-I (450 mg). The filter cake washed with EtOAc/MeOH=1:1 (3 mL), filtered, give 1-2 as yellow solid.

Preparation of 2: A solution of 2-2-I (450 mg) in aqueous formic acid (16% v/v, 3 mL) was stirred at 45° C. for 20 min. HPLC showed the methyl ketal was hydrolyzed completely. Toluene (20 mL) was added, and the mixture was concentrated in vacuum at 40° C. The residue was dissolved in DMSO (5 mL) and purified by prep-HPLC (C18, 5-µm, 250×50 mm, 80 mL/min, 3% to 33% MeCN: 0.1% FA (aq) over 20 minutes) to provide 2-I (70.00 mg, 23% yield) as a yellow solid.

$^1$H NMR (400 MHz, Methanol-d4+Pyr-d5): δ 8.70 (s, 1H) 6.16-6.52 (m, 14H) 5.37-5.55 (m, 2H) 4.80 (s, 1H) 4.50 (br. s., 1H) 4.39 (m, 1H) 4.25-4.37 (m, 4H) 3.37-3.61 (m, 10H) 3.25-3.37 (m, 1H) 2.97 (s, 4H) 2.37-2.42 (m, 3H) 2.24 (s, 2H) 1.47-1.87 (m, 14H) 1.29 (d, J=6 Hz, 3H) 1.23 (d, J=6 Hz, 3H) 1.12 (d, J=6 Hz, 3H) 1.11 (d, J=6 Hz, 3H). LCMS (ESI): m/z: [M+Na] calcd for C$_{51}$H$_{82}$N$_4$O$_{16}$Na: 1029.57; found 1029.6.

Example 4. Preparation of Compound 2-BF

Step 1: A 1 L round-bottom flask was charged with 1-2 (Example 1; 11.36 g, ca. 9.8 mmol). Anhydrous THF (100 mL) was added and the suspension/solution was stirred at RT for 10 min. Methyl amine (40 mL, 2 M in THF, 80 mmol) was then added and the mixture was stirred at RT for 12 h. More methyl amine (10 mL, 2 M in THF, 20 mmol) was added and the mixture was further stirred for 15 h until most of the starting material was consumed as determined by LCMS analysis (Method 1). A small amount (1-2%) of the starting Fmoc-deprotected oxazolidinone (RT=4.1 min) remained when the reaction was stopped. The reaction was then diluted with MTBE (500 mL) and filtered through a fritted glass funnel. The solid was washed with MTBE (50 mL) and then dried under high vacuum for 1 h. A yellow/orange solid, 2-2-BF, (9.9 g, >100% yield) was obtained. LCMS, RT=3.78 min, 966.8 m/z [M+H]$^+$.

Step 2: 2-2-BF was dissolved in 6 mL DMSO and diluted with water (1 mL). The pH of the solution was adjusted to 3 with 20% aq. formic acid. The mixture was loaded on an HPLC column and subjected to HPLC purification. Column: Microsorb (100 Å pore size, 10 µm particle size) C-18 column (50×450 mm); flow rate=100 mL/min; mobile phase A: 99.7% water, 0.3% HCOOH; mobile phase B: 99.7% ACN, 0.3% HCOOH; gradient elution from 0% B to 95% B over 95 min; detection at 383 nm. The total volume of eluant was 10 L. The compound eluted at 31-35% of buffer B. Eight 50 mL fractions containing the desired compound were combined and evaporated under reduced pressure at a bath temperature between 30-40° C. to 20% of the initial volume. The pH of the solution was adjusted to 7.5 with sodium bicarbonate. The suspension (100 mL) thus obtained was centrifuged at 4000 rpm. The supernatant was separated and the solid portion re-suspended in water (100 mL) and centrifuged again. The procedure was repeated three times until the disappearance of the salt signal on the ELSD chromatogram. The final solid was re-suspended in water and subjected to lyophilization to afford the target material (2-BF, 760 mg, 38%) as a yellow powder.

Example 5. Preparation of Compound 2-BC

Step 1: To a 20 mL vial was added b-alanine allylester hydrochloride (1.125 g, 6.79 mmol, 39 eq.), sodium carbonate (2.19 g, 20.66 mmol, 120 eq.), and DMF (8.6 mL). The resulting suspension was stirred at room temperature for 15 minutes. The suspension was then filtered through Celite followed by filtration through a syringe tip 0.2-µm filter. The resulting b-alanine allylester free base was then added to a 20 mL vial containing 1-2 (200 mg, 0.174 mmol, 1 eq.). The reaction was placed in a preheated heating block at 40° C. and allowed to stir for 5 h. The reaction was then directly purified directly by prep HPLC (C18, 5-mm, 30×150 mm, 25 mL/min, 95:5 to 40:60 0.3% HCO$_2$H (aq):MeCN over 10 minutes). Upon removal of the acetonitrile and aqueous formic acid solution in vacuo at 35° C., the C-13 methyl ketal is converted to a hemiketal yielding 2-BC-allylester as a yellow solid (59.4 mg, 32.5% yield).

Step 2: To a 40 mL vial was added 2-BC-allylester (370 mg, 352.3 mmol, 1 eq.), and thiosalicylic acid (203.4 mg, 1.76 mmol, 5 eq.). The vial was then brought into a glovebox and Pd(PPh$_3$)$_4$ was added (205 mg, 0.18 mmol, 0.5 eq.). The vial was sealed with a septa cap, removed from the glovebox, and DMF was added (17.6 mL, 0.2 M) via syringe. The reaction then stirred at room temperature for 1 h. The reaction was then poured into Et$_2$O (370 mL) in multiple 50 mL centrifuge tubes. The resulting suspension was then centrifuged at 3700 G for 5 minutes. The pale red supernatant was decanted and the resulting yellow/orange solid was dissolved in DMSO and purified by prep HPLC (C18, 5-mm, 50×250 mm, 80 mL/min, 80:20 to 40:60 0.3% HCO$_2$H (aq):MeCN over 9 minutes) yielding 2-BC as a yellow solid (124.4 mg, 35% yield). $^1$H NMR (400 MHz, Methanol-d4+Pyr-d5): δ ppm 6.45 (br. s., 11H), 5.02 (s, 1H), 4.42-4.84 (m, 5H), 4.31 (br. s., 1H), 3.68-4.09 (m, 7H), 3.40 (d, J=9.26 Hz, 1H), 2.47-2.82 (m, 5H), 2.40 (d, J=14.11 Hz, 2H), 2.24 (d, J=6.17 Hz, 2H), 1.60-2.16 (m, 11H), 1.44-1.60 (m, 5H), 1.40 (d, J=6.62 Hz, 3H), 1.27 (d, J=6.17 Hz, 3H), 1.21 (d, J=7.06 Hz, 3H). LCMS (ESI): m/z: [M+Na] calcd for C$_{50}$H$_{79}$N$_8$O$_{17}$Na: 1033.5; found 1033.4.

Example 6. Synthesis of Compound 2-B

Compound 2-B was synthesized in the manner similar to Compound 2-I (Example 3), except piperazine was substituted with N,N-Dimethylamine. $^1$H NMR (400 MHz, Methanol-d4+Py-d$^5$): δ 8.82 (s, 1H) 6.17-6.54 (m, 14H) 5.52 (d, 1H) 4.80 (s, 1H) 4.52 (br. s., 1H) 4.40 (s, 1H) 4.30-4.38 (m, 2H) 4.28-4.30 (m, 2H) 3.78-3.87 (m, 3H) 3.78 (t, J=4.8 Hz, 3H) 3.40-3.42 (m, 1H) 3.26-3.28 (m, 2H) 2.80 (s, 6H) 2.43-2.247 (m, 3H) 2.27-2.23 (m, 2H) 1.57-1.90 (m, 13H) 1.33 (d, J=6 Hz, 3H) 1.25 (d, J=6 Hz, 3H) 1.14 (d, J=6 Hz, 3H) 1.03 (d, J=6 Hz, 3H). LCMS (ESI): m/z: [M+Na] calcd for C$_{49}$H$_{79}$N$_3$O$_{16}$Na: 988.55; found 988.6.

Example 7. Synthesis of Compound 2-C

Compound 2-C was synthesized in the manner similar to Compound 2-I (Example 3), except piperazine was substituted with Piperidine. $^1$H NMR (400 MHz, Methanol-d4+Py-d$^5$): δ 8.67 (s, 1H) 6.16-6.50 (m, 14H) 5.36-5.40 (m, 2H) 4.79 (s, 1H) 4.63 (br. s., 1H) 4.51 (s, 1H) 4.27-4.37 (m, 4H) 3.66-3.84 (m, 7H) 3.25 (m, 3H) 2.23-2.42 (m, 4H) 1.53-1.90 (m, 22H) 1.33 (d, J=6 Hz, 3H) 1.23 (d, J=6 Hz, 3H) 1.12 (d, J=6 Hz, 3H) 1.03 (d, J=6 Hz, 3H). LCMS (ESI): m/z: [M+Na] calcd for C$_{52}$H$_{83}$N$_3$O$_{16}$Na: 1028.58; found 1028.6.

Example 8. Synthesis of Compound 2-J

Compound 2-J was synthesized in the manner similar to Compound 2-I (Example 3), except piperazine was substituted with N-methylpiperazine. $^1$H NMR (400 MHz, Methanol-d4+Py-d$^5$): δ 8.71 (s, 1H) 6.18-6.54 (m, 14H) 5.42-5.52 (m, 2H) 4.84 (s, 1H) 4.66 (br. s., 1H) 4.41 (s, 1H) 4.29-4.38 (m, 5H) 3.37-3.85 (m, 4H) 3.26-3.47 (m, 7H) 2.29-2.43 (m, 3H) 2.25-2.26 (m, 6H) 2.09 (s, 4H) 1.58-1.60 (m, 15H) 1.32 (d, J=6 Hz, 3H) 1.26 (d, J=6 Hz, 3H) 1.24 (d, J=6 Hz, 3H) 1.13 (d, J=6 Hz, 3H). LCMS (ESI): m/z: [M+Na] calcd for C$_{52}$H$_{84}$N$_4$O$_{16}$Na: 1043.59; found 1043.5.

Example 9. Synthesis of Compound 2-D

Compound 2-D was synthesized in the manner similar to Compound 2-I (Example 3), except piperazine was substituted with azetidine. $^1$H NMR (400 MHz, Methanol-d4+Pyr-d5): δ 8.77 (s, 1H) 6.16-6.55 (m, 14H) 4.84-5.52 (m, 2H) 4.84 (s, 1H) 4.66 (br. s., 1H) 4.53 (t, 1H) 4.24-4.36 (m, 5H) 3.86-3.88 (m, 5H) 3.70-3.85 (m, 3H) 3.28-3.50 (m, 4H) 2.43-2.45 (m, 3H) 2.26 (s, 2H) 1.59-1.92 (m, 14H) 1.35 (d, J=6 Hz, 3H) 1.26 (d, J=6 Hz, 3H) 1.15 (d, J=6 Hz, 3H) 1.07 (d, J=6 Hz, 3H). LCMS (ESI): m/z: [M+Na] calcd for C$_{50}$H$_{79}$N$_3$O$_{16}$Na: 1000.55; found 1000.5.

Example 10. Synthesis of Compound 2-F

Compound 2-F was synthesized in the manner similar to Compound 2-I, except piperazine was substituted with N',N' 1-dimethylethane-1,2-diamine. $^1$H NMR (400 MHz, Methanol-d4+Pyr-d5): δ 8.62 (s, 1H) 6.17-6.51 (m, 14H) 5.34-5.48 (m, 2H) 4.77 (s, 1H) 4.48 (br. s., 1H) 4.36 (m, 1H) 4.23-4.30 (m, 3H) 4.05 (m, 1H) 3.42-3.81 (m, 6H) 3.22-3.26 (m, 1H) 2.92 (m, 2H) 2.620 (s, 6H) 2.44-2.52 (m, 4H) 2.20-2.44 (m, 2H) 1.58-1.86 (m, 6H) 1.51-1.54 (m, 7H) 1.32 (d, J=6 Hz, 3H) 1.23 (d, J=6 Hz, 3H) 1.12 (d, J=6 Hz, 3H) 1.04 (d, J=6 Hz, 3H). LCMS (ESI): m/z: [M+H] calcd for C$_{51}$H$_{84}$N$_4$O$_{16}$: 1009.59; found 1009.6.

Example 11. Synthesis of Compound 2-T

Compound 2-T was synthesized in the manner similar to Compound 2-I (Example 3), except piperazine was substituted with 2-(pyridin-2-yl)ethanamine. $^1$H NMR (400 MHz, Methanol-d4+Pyr-d5): δ 8.64 (s, 1H) 8.38-8.39 (m, 1H) 7.53-7.57 (m, 1H) 7.28-7.31 (m, 1H) 7.17-7.20 (m, 14H) 6.16-6.35 (m, 14H) 5.33-5.50 (m, 3H) 4.84 (s, 1H) 4.64 (br. s., 2H) 4.49 (t, 1H) 3.71-4.44 (m, 3H) 3.57-3.68 (m, 2H) 3.54-3.55 (m, 3H) 3.45-3.54 (m, 2H) 3.23-3.25 (m, 1H) 2.96-2.97 (m, 2H) 1.85-2.23 (m, 4H) 1.82-1.85 (m, 2H) 1.50-1.82 (m, 14H) 1.32 (d, J=6 Hz, 3H) 1.23 (d, J=6 Hz, 3H) 1.12 (d, J=6 Hz, 3H) 1.04 (d, J=6 Hz, 3H). LCMS (ESI): m/z: [M+Na] calcd for C$_{54}$H$_{82}$N$_4$O$_{16}$Na: 1065.57; found 1065.4.

Example 12. Synthesis of Compound 2-U

Compound 2-U was synthesized in the manner similar to Compound 2-I (Example 3), except piperazine was substituted with pyridin-2-ylmethanamine. $^1$H NMR (400 MHz, Methanol-d4+Pyr-d5): δ 8.80 (s, 1H) 8.42-8.43 (m, 1H) 7.51-7.52 (m, 1H) 7.38-7.40 (m, 1H) 7.02-7.03 (m, 1H) 6.21-6.58 (m, 14H) 5.56 (s, 1H) 4.91 (s, 1H) 4.23-4.71 (m, 5H) 3.77-3.89 (m, 4H) 3.25-3.50 (m, 4H) 2.30-3.25 (m, 1H) 2.28-2.30 (m, 2H) 1.92-2.28 (m, 2H) 1.57-1.89 (m, 13H) 1.35 (d, J=6 Hz, 3H) 1.26 (d, J=6 Hz, 3H) 1.14 (d, J=6 Hz, 3H) 1.09 (d, J=6 Hz, 3H). LCMS (ESI): m/z: [M+Na] calcd for C$_{53}$H$_{80}$N$_4$O$_{16}$Na: 1051.56; found 1051.4.

Example 13. Synthesis of Compound 2-Y

Compound 2-Y was synthesized in the manner similar to Compound 2-I (Example 3), except piperazine was substituted with (S)-1-aminopropan-2-ol. $^1$H NMR (400 MHz, Methanol-d4+Pyr-d5): δ 8.74 (s, 1H), 6.15-6.51 (m, 14H), 5.29-5.37 (m, 2H), 4.85 (s, 1H), 4.65 (br. s., 1H), 4.38 (t, 1H), 4.33-4.35 (m, 5H), 3.85-3.87 (m, 2H), 3.71-3.74 (m, 1H), 3.66-3.69 (m, 1H), 3.23-3.49 (m, 2H), 2.21-2.37 (m, 3H), 1.55-1.87 (m, 11H), 1.23-1.31 (m, 13H), 1.06-1.13 (m, 15H). LCMS (ESI): m/z: [M+Na] calcd for $C_{50}H_{81}N_3O_{17}Na$: 1018.56; found 1018.5.

Example 14. Synthesis of Compound 2-AB

Compound 2-AB was synthesized in the manner similar to Compound 2-I (Example 3), except piperazine was substituted with 1-(piperazin-1-yl)ethanone. $^1$H NMR (400 MHz, Methanol-d4+Pyr-d5): δ 8.68-8.71 (s, 2H) 6.21-6.53 (m, 13H) 5.54 (m, 2H) 4.69-4.84 (m, 5H) 4.35-4.40 (m, 2H) 3.67-3.91 (m, 9H) 3.38-3.53 (m, 4H) 1.59-2.50 (m, 35H) 1.30 (d, J=6 Hz, 3H) 1.26 (d, J=6 Hz, 3H) 1.20 (d, J=6 Hz, 3H) 1.10 (d, J=6 Hz, 3H). LCMS (ESI): m/z: [M+Na] calcd for $C_{53}H_{84}N_4O_{16}Na$: 1071.58.

Example 15. Synthesis of Compound 2-AF

Compound 2-AF was synthesized in the manner similar to Compound 2-I (Example 3), except piperazine was substituted with 2-morpholinoethanamine. $^1$H NMR (400 MHz, Methanol-d4+Pyr-d5): δ 8.62 (s, 1H) 6.18-6.52 (m, 14H) 5.39-5.51 (m, 2H) 4.86 (s, 1H) 4.68 (br. s., 1H) 4.46-4.52 (t, 1H) 4.35 (m, 2H) 3.73-3.88 (m, 4H) 3.37-3.61 (m, 10H) 2.26-2.48 (m, 12H) 1.34-1.88 (m, 12H) 1.25 (d, J=6 Hz, 3H) 1.14 (d, J=6 Hz, 3H) 1.07 (d, J=6 Hz, 3H) 1.06 (d, J=6 Hz, 3H). LCMS (ESI): m/z: [M+H] calcd for $C_{53}H_{87}N_4O_{17}$: 1051.60; found 1051.70.

Example 16. Synthesis of Compound 2-BN

Compound 2-BN was synthesized in the manner similar to Compound 2-I (Example 3), except piperazine was substituted with 2-(4-methylpiperazin-1-yl)ethanamine. $^1$H NMR (400 MHz, Methanol-d4+Pyr-d5): δ ppm 6.03-6.60 (m, 14H), 5.49 (d, J=6.02 Hz, 1H) 5.35-5.43 (m, 1H) 4.80 (s, 1H) 4.65 (d, J=6.90 Hz, 1H) 4.46-4.54 (m, 1H) 4.33 (br. s., 1H) 4.19-4.28 (m, 2H) 4.01-4.12 (m, 2H) 3.79-3.88 (m, 2H) 3.72 (d, J=11.17 Hz, 1H) 3.51-3.68 (m, 3H) 3.43 (dd, J=9.03, 6.02 Hz, 2H) 3.27 (d, J=9.79 Hz, 2H) 2.32-2.59 (m, 13H) 2.16-2.28 (m, 5H) 1.81-2.04 (m, 5H) 1.36-1.80 (m, 11H) 1.34 (d, J=6.15 Hz, 3H) 1.25 (d, J=6.40 Hz, 3H) 1.15 (d, J=6.27 Hz, 3H) 1.06 (d, J=7.03 Hz, 3H). LCMS (ESI): m/z: [M+H] calcd for $C_{54}H_{90}N_5O_{16}$: 1064.63; found 1064.6.

Example 17. Synthesis of Compound 2-BO

Compound 2-BO was synthesized in the manner similar to Compound 2-I (Example 3), except piperazine was substituted with cyclopropylmethanamine. $^1$H NMR (400 MHz, Methanol-d4+Pyr-d5): δ 5.86-6.26 (m, 13H), 5.22 (d, J=5.73 Hz, 1H), 5.08 (br. s., 2H), 4.33 (br. s., 1H), 4.21 (br. s., 1H), 3.92-4.11 (m, 2H), 3.68-3.86 (m, 2H), 3.53 (t, J=9.04 Hz, 1H), 3.28-3.46 (m, 2H), 3.01-3.15 (m, 3H), 2.93 (d, J=8.82 Hz, 1H), 2.65-2.81 (m, 2H), 2.25-2.50 (m, 2H), 2.01-2.19 (m, 2H), 1.85-1.97 (m, 2H), 1.03-2.00 (m, 14H), 1.01 (d, J=5.73 Hz, 3H), 0.92 (d, J=6.17 Hz, 3H), 0.81 (d, J=6.17 Hz, 3H), 0.73 (d, J=7.06 Hz, 3H). LCMS (ESI): m/z: [M+Na] calcd for $C_{51}H_8N_3O_{16}Na$: 1014.56; found 1014.6.

Example 18. Synthesis of Compound 2-BP

Compound 2-BP was synthesized in the manner similar to Compound 2-I (Example 3), except piperazine was substituted with (2-chlorophenyl)methanamine. $^1$H NMR (400 MHz, Methanol-d4+Pyr-d5): δ ppm 8.73-8.85 (m, 1H) 7.47-7.54 (m, 1H) 7.21-7.25 (m, 1H) 7.10-7.15 (m, 1H) 7.01-7.09 (m, 1H) 6.10-6.58 (m, 12H) 5.49-5.59 (m, 1H) 5.36-5.41 (m, 1H) 4.81 (s, 1H) 4.62-4.71 (m, 1H) 4.48 (s, 4H) 4.31-4.41 (m, 2H) 4.22-4.28 (m, 1H) 4.06-4.17 (m, 1H) 3.80-3.91 (m, 1H) 3.67-3.78 (m, 2H) 3.54-3.64 (m, 1H) 3.37-3.48 (m, 1H) 3.18-3.27 (m, 1H) 2.98-3.09 (m, 1H) 2.16-2.64 (m, 5H) 1.99-2.13 (m, 1H) 1.79-1.96 (m, 3H) 1.40-1.78 (m, 7H) 1.32 (d, J=6.17 Hz, 4H) 1.24 (d, J=6.17 Hz, 3H) 1.12 (d, J=6.62 Hz, 3H) 1.05 (d, J=7.06 Hz, 3H). LCMS (ESI): m/z: [M+Na] calcd for $C_{54}H_{80}ClN_3O_{16}Na$: 1084.52; found 1084.4.

Example 19. Synthesis of Compound 2-BQ

Compound 2-BQ was synthesized in the manner similar to Compound 2-I (Example 3), except piperazine was substituted with (3-chlorophenyl)methanamine. $^1$H NMR (400 MHz, Methanol-d4+Pyr-d5): δ ppm 8.76-8.82 (m, 1H) 7.33 (s, 2H), 7.08-7.16 (m, 3H), 6.86-6.93 (m, 1H), 6.07-6.63 (m, 12H), 5.48-5.58 (m, 1H), 5.36-5.41 (m, 1H), 4.81 (s, 1H), 4.62-4.74 (m, 1H), 4.53 (t, J=10.36 Hz, 1H), 4.24-4.45 (m, 5H), 4.08-4.21 (m, 1H), 3.85 (t, J=9.70 Hz, 1H), 3.60-3.79 (m, 3H), 3.32-3.46 (m, 2H), 3.24 (d, J=9.70 Hz, 1H), 3.15 (d, J=9.70 Hz, 1H), 2.59 (dd, J=14.55, 4.41 Hz, 1H), 2.32-2.52 (m, 2H), 2.17-2.31 (m, 2H), 1.98-2.15 (m, 1H), 1.78-1.97 (m, 3H), 1.37-1.78 (m, 8H), 1.33 (d, J=6.17 Hz, 3H), 1.18-1.27 (m, 3H), 1.12 (d, J=6.17 Hz, 3H), 1.05 (d, J=7.06 Hz, 3H). LCMS (ESI): m/z: [M+Na] calcd for $C_{54}H_{80}ClN_3O_{16}Na$: 1084.52; found: 1084.5.

Example 20. Synthesis of Compound 2-BS

Compound 2-BS was synthesized in the manner similar to Compound 2-I (Example 3), except piperazine was substituted with 1-methylazetidin-3-amine. $^1$H NMR (400 MHz, Methanol-d4+Pyr-d5): δ ppm 6.00-6.60 (m, 13H) 5.51 (d, J=5.29 Hz, 1H) 5.32-5.42 (m, 2H) 4.82 (s, 1H) 4.39-4.71 (m, 4H) 4.22-4.37 (m, 2H) 3.78-4.19 (m, 5H) 3.40-3.76 (m, 7H) 3.21-3.33 (m, 6H) 2.53 (s, 3H) 2.32-2.46 (m, 2H) 2.19-2.26 (m, 1H) 1.35-2.16 (m, 13H) 1.33 (d, J=6.17 Hz, 3H) 1.23 (d, J=6.62 Hz, 3H) 1.08-1.16 (m, 3H) 1.04 (d, J=7.06 Hz, 3H). LCMS (ESI): m/z: [M+H] calcd for $C_{51}H_{83}N_4O_{16}$:1007.57; found 1007.5.

Example 21. Synthesis of Compound 2-Z

Compound 2-Z was synthesized in the manner similar to Compound 2-I (Example 3), except piperazine was substituted with 2-(2-methoxyethoxy)ethanamine. $^1$H NMR (400 MHz, Methanol-d4+Pyr-d5): δ ppm 8.75-8.73 (1H, M) 6.54-6.19 (14H, m), 5.49-5.39 (2H, m), 4.80-3.28 (25H, m), 2.23-0.92 (30H, m). LCMS (ESI): m/z: [M+Na] calcd for $C_{52}H_{85}N_3O_{18}$: 1062.6; found 1062.6.

Example 22. Synthesis of Compound 2-AE

Compound 2-AE was synthesized in the manner similar to Compound 2-I (Example 3), except piperazine was substituted with (R)-1-(2-aminoethyl)pyrrolidin-3-ol. $^1$H NMR (400 MHz, Methanol-d4+Pyr-d5): δ ppm 6.48-6.15 (14H, m), 5.37-5.32 (2H, m), 4.83-2.86 (22H, m), 2.25-0.97 (33H, m). LCMS (ESI): m/z: [M+H] calcd for $C_{53}H_{87}N_4O_{17}$: 1051.6; found 1051.6.

Example 23. Synthesis of Compound 2-AH

Compound 2-AH was synthesized in the manner similar to Compound 2-I (Example 3), except piperazine was substituted with phenylmethanamine. ¹H NMR (400 MHz, Methanol-d4+Pyr-d5): δ ppm 8.73 (1H, m), 7.31-7.12 (5H, m), 6.49-6.16 (14H, m), 5.37-5.27 (2H, m), 4.79-3.23 (16H, m) 2.36-1.04 (30H, m). LCMS (ESI): m/z: [M+Na] calcd for $C_{54}H_{81}N_3O_{16}Na$: 1050.6; found 1050.6.

Example 24. Synthesis of Compound 2-E

Compound 2-E was synthesized in the manner similar to Compound 2-I (Example 3), except piperazine was substituted with morpholine. ¹H NMR (400 MHz, Methanol-d4+Pyr-d5): δ 6.09-6.57 (m, 13H) 5.51 (d, J=6.17 Hz, 1H) 4.80 (s, 1H) 4.64 (br. S., 1H) 4.52 (br. S., 1H) 4.31-4.45 (m, 2H) 4.20-4.31 (m, 2H) 3.62-3.90 (m, 5H) 3.52 (d, J=4.41 Hz, 4H) 3.39 (d, J=4.41 Hz, 5H) 3.18-3.27 (m, 2H) 2.32-2.53 (m, 3H) 2.17-2.31 (m, 2H) 2.04 (d, J=11.03 Hz, 2H) 1.87 (d, J=7.94 Hz, 3H) 1.62-1.79 (m, 3H) 1.27-1.62 (m, 10H) 1.23 (d, J=6.17 Hz, 3H) 1.12 (d, J=6.17 Hz, 3H) 1.04 (d, J=7.06 Hz, 3H). LCMS (ESI): m/z: [M+Na] calcd for $C_{51}H_{81}N_3O_{17}Na$: 1030.6; found 1030.6.

Example 25. Synthesis of Compound 2-AG

Compound 2-AG was synthesized in the manner similar to Compound 2-I (Example 3), except piperazine was substituted with cyclobutanamine. ¹H NMR (400 MHz, Methanol-d4+Pyr-d5): δ 6.05-6.63 (m, 13H) 4.82 (s, 1H) 4.66 (br. s., 1H) 4.52 (t, J=10.54 Hz, 1H) 4.18-4.43 (m, 4H) 4.03-4.14 (m, 1H) 3.85 (br. s., 1H) 3.64-3.78 (m, 2H) 3.60 (br. s., 1H) 3.46 (dd, J=8.78, 6.27 Hz, 1H) 3.27 (d, J=9.54 Hz, 1H) 1.96-2.57 (m, 10H) 1.62-1.96 (m, 9H) 1.38-1.63 (m, 8H) 1.35 (d, J=6.02 Hz, 4H) 1.25 (d, J=6.53 Hz, 3H) 1.15 (d, J=6.53 Hz, 3H) 1.07 (d, J=7.53 Hz, 3H). LCMS (ESI): m/z: [M+Na] calcd for $C_{51}H_{81}N_3O_{16}Na$: 1014.5; found 1014.5.

Example 26. Synthesis of Compound 2-AI

Compound 2-AI was synthesized in the manner similar to Compound 2-I (Example 3), except piperazine was substituted with pyrrolidine. ¹H NMR (400 MHz, Methanol-d4+Pyr-d5): 66.10-6.61 (m, 12H) 5.53 (d, J=5.52 Hz, 1H) 4.83 (s, 1H) 4.68 (br. s., 1H) 4.51-4.61 (m, 1H) 4.24-4.48 (m, 4H) 3.67-3.92 (m, 4H) 3.19-3.31 (m, 5H) 2.20-2.56 (m, 5H) 2.00-2.14 (m, 1H) 1.84-2.00 (m, 3H) 1.30-1.83 (m, 17H) 1.26 (d, J=6.02 Hz, 3H) 1.14 (d, J=6.02 Hz, 3H) 1.07 (d, J=7.53 Hz, 3H). LCMS (ESI): m/z: [M+Na] calcd for $C_{51}H_{81}N_3O_{16}Na$: 1014.5; found 1014.5.

Example 27. Synthesis of Compound 2-BT

Compound 2-BT was synthesized in the manner similar to Compound 2-I (Example 3), except piperazine was substituted with ethanamine. ¹H NMR (400 MHz, Methanol-d4+Pyr-d5): δ 8.69 (s, 1H), 6.14-6.48 (m, 13H), 5.36-5.49 (m, 3H), 4.84 (s, 1H), 4.81 (br. s., 1H), 4.64 (t, 1H), 4.48-4.53 (m, 1H), 4.24-4.34 (m, 3H), 4.06-4.08 (m, 1H), 3.74-3.84 (m, 1H), 3.60-3.74 (m, 1H), 3.42-3.47 (m, 1H), 3.23-3.26 (m, 2H), 3.13-3.17 (m, 3H), 2.34-2.50 (m, 3H), 2.20-2.24 (m, 2H), 1.86 (m, 2H), 1.41-1.72 (m, 7H), 1.31 (d, J=6 Hz, 3H), 1.23 (d, J=6 Hz, 3H), 1.11 (d, J=6 Hz, 3H), 0.98 (d, J=6 Hz, 3H). LCMS (ESI): m/z: [M+Na] calcd for $C_{49}H_{79}N_3O_{16}Na$: 988.55; found 988.5.

Example 28. Synthesis of Compound 2-BU

Compound 2-BU was synthesized in the manner similar to Compound 2-I (Example 3), except piperazine was substituted with cyclopropanamine. ¹H NMR (400 MHz, Methanol-d4+Pyr-d5): δ ppm 7.37 (d, J=8.03 Hz, 2H) 7.21 (t, J=7.78 Hz, 2H) 6.97 (t, J=7.28 Hz, 1H) 6.09-6.57 (m, 13H) 5.50 (br. s., 2H) 5.36-5.45 (m, 2H) 4.77 (s, 1H) 4.63 (br. s., 1H) 4.46-4.55 (m, 2H) 4.27-4.39 (m, 3H) 4.21 (d, J=3.01 Hz, 1H) 4.04-4.15 (m, 2H) 3.79-3.89 (m, 2H) 3.73 (d, J=11.04 Hz, 2H) 3.53-3.66 (m, 3H) 3.42 (dd, J=9.03, 6.02 Hz, 1H) 3.26 (br. s., 1H) 3.12 (d, J=9.03 Hz, 3H) 2.50-2.59 (m, 2H) 2.41-2.49 (m, 2H) 2.33-2.40 (m, 1H) 2.19-2.29 (m, 3H) 1.95-2.06 (m, 2H) 1.81-1.94 (m, 4H) 1.37-1.79 (m, 12H) 1.33 (d, J=6.02 Hz, 3H) 1.25 (d, J=6.53 Hz, 3H) 1.15 (d, J=6.53 Hz, 3H) 1.07 (d, J=7.53 Hz, 3H) 0.60 (d, J=7.03 Hz, 3H) 0.46 (br. s., 3H). LCMS (ESI): m/z: [M+Na] calcd for $C_{50}H_{79}N_3O_{16}Na$: 1000.55; found 1000.5.

Example 29. Synthesis of Compound 2-BV

Compound 2-BV was synthesized in the manner similar to Compound 2-I (Example 3), except piperazine was substituted with 3,3-difluorocyclobutanamine. ¹H NMR (400 MHz, Methanol-d4+Pyr-d5): δ ppm 6.03-6.56 (m, 13H) 5.48 (d, J=6.62 Hz, 1H) 5.31-5.39 (m, 2H) 4.72 (s, 1H) 4.60 (br. s., 1H) 4.48 (t, J=10.14 Hz, 1H) 4.20-4.37 (m, 2H) 4.10-4.19 (m, 2H) 3.97-4.09 (m, 1H) 3.81 (t, J=9.48 Hz, 1H) 3.70 (d, J=10.58 Hz, 1H) 3.44-3.63 (m, 2H) 3.31-3.41 (m, 1H) 3.22 (d, J=9.26 Hz, 1H) 2.66-3.02 (m, 3H) 2.28-2.63 (m, 5H) 2.13-2.26 (m, 2H) 1.98 (d, J=8.38 Hz, 1H) 1.59-1.91 (m, 5H) 1.32-1.58 (m, 6H) 1.30 (d, J=6.17 Hz, 3H) 1.21 (d, J=6.62 Hz, 3H) 1.10 (d, J=6.62 Hz, 3H) 1.02 (d, J=7.06 Hz, 3H). LCMS (ESI): m/z: [M–H₂O] calcd for $C_{51}H_{79}F_2N_3O_{16}$: 1027.54; found 1010.3.

Example 30. Synthesis of Compound 2-BW

Compound 2-BW was synthesized in the manner similar to Compound 2-I (Example 3), except piperazine was substituted with (9H-fluoren-9-yl)methyl 2-(aminomethyl)pyrrolidine-1-carboxylate. ¹H NMR (400 MHz, Methanol-d4+Pyr-d5): δ 8.73 (s, 2H) 6.46-6.49 (m, 2H) 6.18-6.33 (m, 11H) 5.5 (s, 2H) 4.75 (s, 1H) 4.52-4.61 (m, 1H) 4.44-4.52 (m, 2H) 4.24-4.34 (m, 3H) 4.12 (s, 1H) 3.72-3.83 (m, 2H) 3.57 (t, 1H) 3.51 (s, 2H) 3.04-3.10 (m, 3H) 2.19-2.42 (m, 3H) 1.53-1.87 (m, 16H) 1.28 (d, J=6 Hz, 3H) 1.23 (d, J=6 Hz, 3H) 1.11 (d, J=6 Hz, 3H) 1.04 (d, J=6 Hz, 3H). LCMS (ESI): m/z: [M+H] calcd for $C_{52}H_{84}N_4O_{16}$: 1021.59; found 1021.5.

Example 31. Synthesis of Compound 2-G

Compound 2-G was synthesized in the manner similar to Compound 2-I (Example 3), except piperazine was substituted with (1S,3S)-cyclobutane-1,3-diamine. ¹H NMR (400 MHz, Methanol-d4+Pyr-d5): δ 8.76 (s, 1H) 6.16-6.56 (m, 13H) 5.54-5.55 (m, 1H) 4.86 (s, 1H) 4.46-4.56 (m, 2H) 4.38-(m, 2H) 4.12-4.18 (m, 2H) 3.68-3.88 (m, 3H) 3.38-3.49 (m, 2H) 3.38-3.15 (m, 1H) 3.22-3.24 (m, 1H) 1.38-2.74 (m, 22H) 1.32 (d, J=6 Hz, 3H) 1.24 (d, J=6 Hz, 3H) 1.11 (d, J=6 Hz, 3H) 1.04 (d, J=6 Hz, 3H). LCMS (ESI): m/z: [M+H] calcd for $C_{51}H_{82}N_4O_{16}$: 1007.57; found 1007.5.

Example 32. Synthesis of Compound 2-BX

Compound 2-BX was synthesized in the manner similar to Compound 2-I (Example 3), except piperazine was substituted with trans-cyclobutane-1,3-diamine. ¹H NMR (400 MHz, Methanol-d4+Pyr-d5): δ ppm 8.67-8.75 (m, 1H) 6.07-6.62 (m, 13H) 5.52 (d, J=6.17 Hz, 1H) 5.34-5.44 (m, 2H)

4.83 (s, 1H) 4.23-4.73 (m, 5H) 4.12 (td, J=10.36, 4.85 Hz, 1H) 3.59-3.95 (m, 5H) 3.32-3.51 (m, 3H) 3.24 (d, J=9.26 Hz, 1H) 2.18-2.63 (m, 8H) 1.95-2.12 (m, 1H) 1.61-1.94 (m, 6H) 1.33-1.61 (m, 6H) 1.31 (d, J=5.73 Hz, 3H) 1.23 (d, J=6.17 Hz, 3H) 1.12 (d, J=6.17 Hz, 3H) 1.04 (d, J=7.06 Hz, 3H). LCMS (ESI): m/z: [M+Na] calcd for $C_{51}H_{82}N_4O_{16}Na$: 1029.57; found 1029.5.

Example 33. Synthesis of Compound 2-L

Compound 2-L was synthesized in the manner similar to Compound 2-I (Example 3), except piperazine was substituted with 2-methyl-2,6-diazaspiro[3.3]heptane. $^1$H NMR (400 MHz, Methanol-d4+Pyr-d5): δ ppm 6.29 (br. s., 13H), 5.50 (d, J=4.41 Hz, 2H), 4.83 (s, 1H), 4.60-4.69 (m, 1H), 4.46-4.57 (m, 1H), 4.34 (d, J=3.09 Hz, 3H), 4.23 (d, J=3.97 Hz, 2H), 3.95-4.06 (m, 4H), 3.62-3.88 (m, 5H), 3.39-3.57 (m, 4H), 3.14 (d, J=8.82 Hz, 1H), 2.91 (d, J=14.55 Hz, 1H), 2.31-2.51 (m, 4H), 2.14-2.30 (m, 5H), 1.27-2.09 (m, 19H), 1.23 (d, J=6.17 Hz, 3H), 1.12 (d, J=6.17 Hz, 3H), 1.00-1.09 (m, 4H). LCMS (ESI): m/z: [M+Na] calcd for $C_{53}H_{84}N_4O_{16}Na$: 1055.6; found 1055.6.

Example 34. Synthesis of Compound 2-BY

Compound 2-BY was synthesized in the manner similar to Compound 2-I (Example 3), except piperazine was substituted with $N_1$-methyl-$N_1$-(oxetan-3-yl)ethane-1,2-diamine. $^1$H NMR (500 MHz, Pyridine-d5: Methanol-$d_4$=1:1): δ 8.76 (d, J=104.4 Hz, 2H), 7.76 (d, J=7.5 Hz, 1H), 7.32 (t, J=7.5 Hz, 1H), 6.69-5.78 (m, 7H), 5.51 (d, J=6.5 Hz, 1H), 5.37 (dd, J=14.7, 10.2 Hz, 1H), 4.79 (d, J=7.5 Hz, 1H), 4.64 (s, 1H), 4.58-4.44 (m, 4H), 4.39-4.30 (m, 1H), 4.25 (d, J=20.8 Hz, 2H), 4.07 (d, J=11.9 Hz, 1H), 3.89-3.67 (m, 2H), 3.69-3.55 (m, 2H), 3.51-3.35 (m, 2H), 3.26 (t, J=7.3 Hz, 3H), 2.79 (t, J=11.9 Hz, 1H), 2.52 (d, J=15.8 Hz, 1H), 2.47-2.35 (m, 2H), 2.34 (d, J=4.7 Hz, 1H), 2.28-2.16 (m, 4H), 1.99 (s, 2H), 1.85 (q, J=15.1, 11.1 Hz, 2H), 1.77-1.62 (m, 1H), 1.55 (dd, J=13.2, 8.4 Hz, 2H), 1.47 (s, 1H), 1.42-1.37 (m, 1H), 1.33 (d, J=6.4 Hz, 3H), 1.23 (d, J=6.3 Hz, 3H), 1.12 (d, J=6.4 Hz, 3H), 1.05 (d, J=7.1 Hz, 3H), 0.76 (s, 1H). LCMS (ESI): Calcd for $C_{53}H_{86}N_4O_{17}$: 1051.28; m/Z: [M+H] found 1052.40.

Example 35. Synthesis of Compound 2-BZ

Compound 2-BZ was synthesized in the manner similar to Compound 2-I (Example 3), except piperazine was substituted with (S)-1-methylpyrrolidin-3-amine. $^1$H NMR (500 MHz, Pyridine-d5: Methanol-$d_4$=1:1): δ 8.77 (s, 1H), 6.55-6.34 (m, 2H), 6.34-6.26 (m, 9H), 6.19 (ddt, J=19.9, 14.0, 6.5 Hz, 1H), 5.52 (d, J=7.3 Hz, 1H), 5.38 (dd, J=14.6, 10.2 Hz, 1H), 4.80 (d, J=16.4 Hz, 1H), 4.65 (s, 1H), 4.52 (t, J=10.8 Hz, 1H), 4.41-4.18 (m, 2H), 4.07 (d, J=12.0 Hz, 1H), 3.88-3.69 (m, 2H), 3.69-3.41 (m, 1H), 3.25 (d, J=9.5 Hz, 1H), 2.72 (d, J=26.5 Hz, 2H), 2.54-2.34 (m, 2H), 2.29 (s, 2H), 2.27-2.19 (m, 2H), 1.89 (d, J=12.6 Hz, 2H), 1.55 (t, J=12.0 Hz, 2H), 1.33 (dd, J=9.4, 6.1 Hz, 3H), 1.24 (d, J=6.3 Hz, 3H), 1.13 (d, J=6.4 Hz, 3H), 1.05 (d, J=7.0 Hz, 3H). LCMS (ESI): Calcd for $C_{52}H_{84}N_4O_{16}$: 1020.59; m/Z: [M+H] found 1021.35.

Example 36. Synthesis of Compound 2-CA

Compound 2-CA was synthesized in the manner similar to Compound 2-I (Example 3), except piperazine was substituted with (R)-1-methylpyrrolidin-3-amine. $^1$H NMR (500 MHz, Methanol-$d_4$): δ 8.52 (s, 2H), 6.53-6.06 (m, 11H), 5.95 (dd, J=15.4, 8.8 Hz, 1H), 5.38 (dd, J=13.7, 9.0 Hz, 2H), 4.58 (s, 1H), 4.45 (d, J=8.5 Hz, 0H), 4.33 (dd, J=24.7, 14.1 Hz, 1H), 4.18 (t, J=9.8 Hz, 1H), 4.11-3.87 (m, 1H), 3.86-3.64 (m, 2H), 3.65-3.40 (m, 1H), 3.42-3.31 (m, 2H), 3.26-3.06 (m, 2H), 3.07-2.96 (m, 1H), 2.95-2.72 (m, 1H), 2.67 (d, J=11.1 Hz, 3H), 2.40 (q, J=7.5, 6.8 Hz, 2H), 2.29 (dd, J=17.2, 9.8 Hz, 1H), 2.19 (dd, J=17.0, 2.6 Hz, 1H), 2.15-1.77 (m, 1H), 1.72 (dd, J=13.6, 8.3 Hz, 3H), 1.59 (d, J=13.9 Hz, 1H), 1.53-1.29 (m, 3H), 1.28 (d, J=6.1 Hz, 4H), 1.19 (d, J=6.4 Hz, 3H), 1.11 (d, J=6.4 Hz, 3H), 1.01 (d, J=7.2 Hz, 3H). LCMS (ESI): Calcd for $C_{52}H_{84}N_4O_{16}$: 1020.59; m/Z: [M+H]: found 1022.35.

Example 37. Synthesis of Compound 2-CB

Compound 2-CB was synthesized in the manner similar to Compound 2-I (Example 3), except piperazine was substituted with 2-(2-oxa-6-azaspiro[3.3]heptan-6-yl)ethan-1-amine. $^1$H NMR (500 MHz, Methanol-$d_4$): δ 8.55 (s, 2H), 6.31 (dddd, J=62.3, 48.4, 19.6, 8.8 Hz, 10H), 5.94 (dd, J=15.2, 9.0 Hz, 1H), 5.48-5.29 (m, 2H), 4.76 (s, 4H), 4.58 (s, 1H), 4.18 (t, J=9.8 Hz, 1H), 4.10-3.91 (m, 2H), 3.82 (td, J=10.5, 4.7 Hz, 1H), 3.74 (s, 4H), 3.60 (d, J=11.0 Hz, 1H), 3.38 (t, J=9.6 Hz, 1H), 3.29-3.08 (m, 2H), 3.10-2.97 (m, 1H), 2.75 (d, J=7.5 Hz, 2H), 2.38 (d, J=6.8 Hz, 0H), 2.29 (dd, J=17.2, 9.8 Hz, 1H), 2.25-2.13 (m, 2H), 2.13-1.94 (m, 1H), 1.86-1.66 (m, 4H), 1.59 (d, J=13.8 Hz, 1H), 1.28 (d, J=6.3 Hz, 3H), 1.20 (d, J=6.4 Hz, 3H), 1.12 (d, J=6.4 Hz, 3H), 1.02 (d, J=7.2 Hz, 3H). LCMS (ESI): Calcd for: $C_{54}H_{86}N_4O_{17}$ 1062.60; m/Z: [M+H] found 1063.50.

Example 38. Synthesis of Compound 2-CC

Compound 2-CC was synthesized in the manner similar to Compound 2-I (Example 3), except piperazine was substituted with (R)-1-methyl-2-aminomethylpyrrolidine. $^1$H NMR (500 MHz, Methanol-$d_4$): δ 8.53 (s, 4H), 6.51-6.13 (m, 8H), 5.99 (dd, J=15.3, 9.1 Hz, 1H), 5.42-5.33 (m, 2H), 4.55 (s, 1H), 4.45-4.32 (m, 2H), 4.25 (s, 1H), 4.18 (s, 2H), 4.03-3.94 (m, 1H), 3.91 (d, J=3.1 Hz, 1H), 3.72 (t, J=9.2 Hz, 1H), 3.61 (d, J=10.8 Hz, 1H), 3.52-3.44 (m, 2H), 3.36 (d, J=8.2 Hz, 1H), 3.23-3.15 (m, 2H), 3.09-3.00 (m, 2H), 2.84 (d, J=9.7 Hz, 1H), 2.70 (s, 3H), 2.38 (d, J=5.6 Hz, 1H), 2.30 (dd, J=17.0, 9.8 Hz, 1H), 2.23-2.08 (m, 4H), 2.08-1.97 (m, 2H), 1.84-1.64 (m, 6H), 1.61 (d, J=14.1 Hz, 1H), 1.53-1.29 (m, 5H), 1.28 (d, J=6.3 Hz, 3H), 1.20 (d, J=6.3 Hz, 3H), 1.12 (d, J=6.3 Hz, 3H), 1.02 (d, J=7.2 Hz, 3H). LC-MS: Calculated $(C_{53}H_{86}N_4O_{16}+H)^+$: 1035.61. Observed: 1036.45.

Example 39. Synthesis of Compound 2-CD

Compound 2-CD was synthesized in the manner similar to Compound 2-I (Example 3), except piperazine was substituted with (S)-1-methyl-2-aminomethylpyrrolidine. $^1$H NMR (500 MHz, Methanol-$d_4$): δ 8.53 (s, 4H), 6.50-6.12 (m, 8H), 5.99 (dd, J=14.9, 9.1 Hz, 1H), 5.42-5.34 (m, 2H), 4.58 (s, 1H), 4.46-4.31 (m, 2H), 4.18 (s, 3H), 3.96 (d, J=16.6 Hz, 2H), 3.76-3.67 (m, 1H), 3.60 (d, J=11.3 Hz, 1H), 3.47-3.37 (m, 2H), 3.28-3.13 (m, 3H), 3.09-3.01 (m, 2H), 2.90 (t, J=12.5 Hz, 1H), 2.71 (d, J=8.6 Hz, 3H), 2.38 (d, J=7.0 Hz, 1H), 2.29 (dd, J=17.2, 9.8 Hz, 1H), 2.25-2.07 (m, 4H), 2.04-1.96 (m, 2H), 1.83-1.68 (m, 6H), 1.60 (d, J=14.0 Hz, 1H), 1.52-1.32 (m, 5H), 1.28 (d, J=6.2 Hz, 3H), 1.20 (d, J=6.5 Hz, 3H), 1.12 (d, J=6.4 Hz, 3H), 1.02 (d, J=7.2 Hz, 3H). LC-MS: Calculated $(C_{53}H_{86}N_4O_{16}+H)^+$: 1035.61. Observed: 1036.45.

Example 40. Synthesis of Compound 2-CE Methyl Ketal

Compound 2-CE methyl ketal was synthesized in the manner similar to Compound 2-3-I, except piperazine was substituted with methyl amine, and formic acid was not used in the mobile phase (acetonitrile/water) during purification. $^1$H NMR (500 MHz, Methanol-d$_4$): δ 6.49-6.10 (m, 12H), 5.86 (dd, J=14.3, 7.1 Hz, 1H), 5.45 (dd, J=14.0, 9.5 Hz, 1H), 5.30-5.18 (m, 1H), 4.61 (t, J=7.3 Hz, 1H), 4.52 (s, 1H), 4.20-4.11 (m, 1H), 3.99-3.91 (m, 1H), 3.80 (s, 1H), 3.71 (dd, J=9.5, 5.0 Hz, 2H), 3.66 (t, J=9.0 Hz, 1H), 3.51 (d, J=10.5 Hz, 1H), 3.41-3.34 (m, 2H), 3.30-3.04 (m, 7H), 2.72 (s, 3H), 2.53 (s, 1H), 2.42-2.34 (m, 1H), 2.34-2.22 (m, 2H), 2.17 (dd, J=14.8, 7.3 Hz, 1H), 1.92-1.78 (m, 2H), 1.78-1.65 (m, 3H), 1.64-1.57 (m, 2H), 1.52 (t, J=12.2 Hz, 1H), 1.44 (tdd, J=14.0, 12.7, 10.4, 5.8 Hz, 5H), 1.27 (d, J=5.9 Hz, 3H), 1.20 (d, J=6.4 Hz, 3H), 1.11 (d, J=6.5 Hz, 3H), 1.01 (d, J=7.2 Hz, 3H). LC-MS: Calculated $(C_{49}H_{79}N_3O_{16}+H)^+$: 966.55. Observed: 966.50.

Example 41. Synthesis of Compound 2-CF

Compound 2-CF was synthesized in the manner similar to Compound 2-I (Example 3), except piperazine was substituted with 2-methyl-2-morpholinopropan-1-amine. $^1$H NMR (500 MHz, Methanol-d$_4$): δ 7.84 (d, J=7.5 Hz, 3H), 7.78 (d, J=7.5 Hz, 1H), 7.73 (d, J=7.6 Hz, 1H), 7.66 (d, J=7.4 Hz, 3H), 7.42 (t, J=7.4 Hz, 3H), 7.36 (td, J=7.4, 1.2 Hz, 4H), 7.33-7.28 (m, 1H), 6.55-6.13 (m, 15H), 5.93 (dd, J=15.1, 9.0 Hz, 1H), 5.36 (d, J=8.5 Hz, 3H), 4.57 (d, J=10.3 Hz, 3H), 4.45 (d, J=8.1 Hz, 1H), 4.34 (t, J=10.4 Hz, 1H), 4.22-4.13 (m, 3H), 4.03 (d, J=8.9 Hz, 1H), 3.92 (d, J=3.1 Hz, 1H), 3.84-3.75 (m, 1H), 3.75-3.53 (m, 16H), 3.44 (d, J=5.2 Hz, 7H), 3.35 (s, 2H), 3.29-3.21 (m, 4H), 3.23-3.07 (m, 8H), 3.01 (s, 2H), 2.89 (s, 2H), 2.66 (s, 45H), 2.59 (s, 13H), 2.60-2.53 (m, 3H), 2.52 (d, J=15.4 Hz, 4H), 2.36 (t, J=4.7 Hz, 7H), 2.24-2.14 (m, 2H), 2.03 (s, 4H), 1.83-1.72 (m, 2H), 1.72 (s, 2H), 1.59 (d, J=13.6 Hz, 3H), 1.53-1.37 (m, 3H), 1.36-1.24 (m, 7H), 1.20 (d, J=6.4 Hz, 5H), 1.12 (d, J=7.9 Hz, 8H), 1.07-0.97 (m, 31H). LC-MS: Calculated $(C_{55}H_{90}N_4O_{17}+H)^+$: 1080.34. Observed: 1080.40.

Example 42. Synthesis of Compound 2-CG

Compound 2-CG was synthesized in the manner similar to Compound 2-I (Example 3), except piperazine was substituted with spiro[3.3]heptan-2-amine. $^1$H NMR (400 MHz, Methanol-d4+Pyr-d5): δ 8.76 (s, 1H) 6.04-6.62 (m, 13H) 5.51 (d, J=5.73 Hz, 1H) 4.80 (s, 1H) 4.64 (br. s., 1H) 4.51 (t, J=10.14 Hz, 1H) 4.20-4.38 (m, 3H) 4.01-4.18 (m, 2H) 3.84 (br. s., 1H) 3.55-3.76 (m, 3H) 3.39-3.50 (m, 1H) 3.24 (d, J=9.70 Hz, 2H) 2.28-2.58 (m, 4H) 2.14-2.25 (m, 3H) 1.96-2.08 (m, 1H) 1.37-1.93 (m, 23H) 1.33 (d, J=6.17 Hz, 4H) 1.23 (d, J=6.17 Hz, 3H) 1.12 (d, J=6.17 Hz, 3H) 1.04 (d, J=7.06 Hz, 3H). LCMS (ESI): m/z: [M+H] calcd for $C_{55}H_{87}N_3O_{16}$: 1032.59; found 1032.6.

Example 43. Synthesis of Compound 2-CH

Compound 2-CH was synthesized in the manner similar to Compound 2-I (Example 3) and 2-CL (Example 55), except piperazine was substituted with allyl (2-aminopropyl)carbamate (3). $^1$H NMR (400 MHz, Methanol-d4+Pyr-d5): δ ppm 6.11-6.61 (m, 10H), 5.55 (d, J=6.02 Hz, 1H), 4.80-4.90 (m, 1H), 4.60-4.75 (m, 1H), 4.56 (d, J=18.70 Hz, 1H), 4.45 (br. s., 1H), 4.24-4.41 (m, 2H), 4.15 (d, J=6.27 Hz, 1H), 3.58-3.90 (m, 4H), 3.42-3.56 (m, 3H), 3.12-3.22 (m, 2H), 2.98-3.08 (m, 1H), 2.90 (dd, J=14.62, 2.95 Hz, 1H), 2.71-2.83 (m, 1H), 2.33-2.68 (m, 3H), 2.17-2.31 (m, 2H), 1.31-2.09 (m, 20H), 1.20-1.31 (m, 6H), 1.15 (d, J=6.27 Hz, 3H), 1.02-1.10 (m, 5H), 0.72 (s, 2H). LCMS (ESI): m/z: [M+Na] calcd for $C_{50}H_{82}N_4O_{16}Na$: 1017.5; found 1017.5.

Synthesis of allyl (2-aminopropyl)carbamate (3)

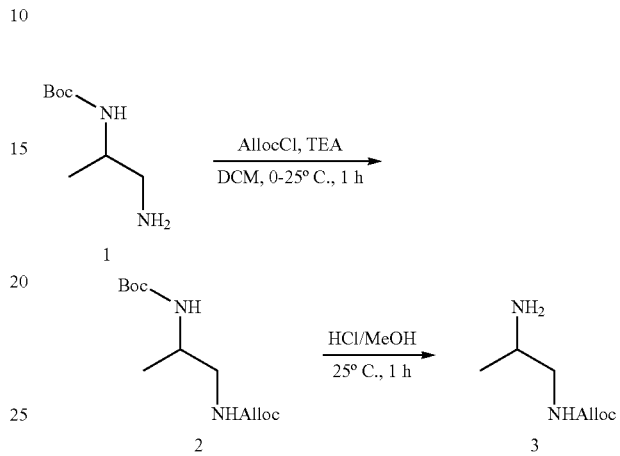

Step 1: To a solution of compound 1 (800.00 mg, 4.59 mmol, 1.00 equiv.) in DCM (6.00 mL) was added allyl carbonochloridate (1.66 g, 13.77 mmol, 1.46 mL, 3.00 equiv.) slowly at 0° C. The mixture was stirred at 25° C. for 1 hour. The mixture was quenched by addition 10% citric acid solution, and extracted with DCM (45 mL). The combined organic layers were dried over Na$_2$SO$_4$, filtered and concentrated under reduced pressure to give the 1.4 g of compound 2. $^1$H NMR (400 MHz, CDCl$_3$-d): δ ppm 1.07 (d, J=6.62 Hz, 3H), 1.27-1.42 (m, 10H), 2.94-3.28 (m, 3H), 3.43 (d, J=7.50 Hz, 1H), 3.70 (br. s., 1H), 4.39-4.63 (m, 2H), 5.04-5.31 (m, 2H), 5.78-5.95 (m, 1H).

Step 2: To a solution of compound 2 (1.40 g, 5.42 mmol, 1.00 equiv.) in MeOH (5.00 mL) was added HCl/MeOH (1 M, 5.42 mL, 1.00 equiv.). The mixture was stirred at 25° C. for 1 hour, and concentrated under reduced pressure to give 1.2 g of compound 3. The residue was neutralized by Ion-exchange resin. $^1$H NMR (400 MHz, Methanol-d4): δ ppm 1.26 (d, J=6.62 Hz, 4H), 3.26-3.31 (m, 5H), 4.55 (d, J=4.85 Hz, 2H), 5.18 (d, J=10.14 Hz, 1H), 5.30 (d, J=17.20 Hz, 1H), 5.85-6.03 (m, 1H).

Example 44. Synthesis of Compound 2-CI

Compound 2-CI was synthesized in the manner similar to Compound 2-I (Example 3) and 2-CL (Example 55), except piperazine was substituted with allyl(1-aminopropan-2-yl)carbamate (3). $^1$H NMR (400 MHz, Methanol-d4+Py-d5): δ ppm 6.07-6.64 (m, 9H), 5.53 (d, J=6.17 Hz, 1H), 4.85 (br. s., 1H), 4.67 (br. s., 1H), 4.45-4.59 (m, 2H), 4.33 (d, J=7.50 Hz, 2H), 4.09-4.23 (m, 1H), 3.39-4.03 (m, 10H), 2.67-2.93 (m, 1H), 2.32-2.67 (m, 4H), 1.96-2.31 (m, 4H), 1.40-1.95 (m, 12H), 1.18-1.40 (m, 8H), 1.12 (d, J=6.17 Hz, 3H), 0.98-1.07 (m, 3H). LCMS (ESI): m/z: [M+Na] calcd for $C_{50}H_{82}N_4O_{16}Na$: 1017.6; found 1017.6.

Synthesis of allyl(1-aminopropan-2-yl)carbamate (3)

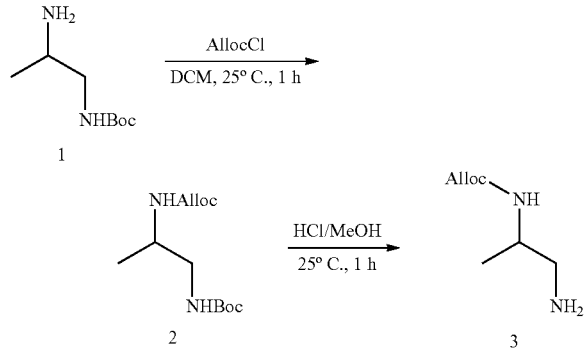

Step 1: To a solution of allyl carbonochloridate (1.66 g, 13.77 mmol, 1.46 mL, 3.00 equiv.) in DCM (10.00 mL) was added compound 1 (800.00 mg, 4.59 mmol, 1.00 equiv.) slowly at 0° C. The mixture was stirred at 25° C. for 1 hour. The mixture was quenched by addition 10% citric acid solution, and extracted with DCM (45 mL). The combined organic layers were dried over $Na_2SO_4$, and filtered. Concentration under reduced pressure resulted in 1.2 g of compound 2.

Step 2: To a solution of compound 2 (500.00 mg, 1.94 mmol, 1.00 equiv.) in MeOH (2.00 mL) was added HCl/MeOH (1 M, 1.94 mL, 1.00 equiv.). The mixture was stirred at 25° C. for 1 hour. The mixture was concentrated under reduced pressure to give 380 mg of compound 3. The residue was alkalized by Ion-exchange resin and submitted to the next step without further purification.

Example 45. Synthesis of Compound 2-AD

Compound 2-AD was synthesized in the manner similar to Compound 2-I (Example 3), except piperazine was substituted with 4-(azetidin-3-yl)morpholine. 1H NMR (400 MHz, Methanol-d4+Pyr-d5): δ ppm 6.05-6.62 (m, 11H), 4.78-4.91 (m, 1H), 4.47-4.72 (m, 1H), 4.11-4.46 (m, 4H), 3.66-4.09 (m, 5H), 3.55 (br. s., 4H), 2.78-3.01 (m, 1H), 2.50 (s, 1H), 1.89 (br. s., 2H), 1.99-2.33 (m, 4H), 1.65-1.83 (m, 1H), 1.43-1.64 (m, 1H), 1.33 (d, J=5.73 Hz, 3H), 1.23 (br. s., 2H), 1.12 (d, J=6.17 Hz, 3H), 1.01-1.07 (m, 1H). LCMS (ESI): m/z: [M+Na] calcd for $C_{54}H_{86}N_4O_{17}Na$: 1085.6; found 1085.6.

Example 46. Synthesis of Compound 2-CM

Compound 2-CM was synthesized in the manner similar to Compound 2-I (Example 3), except piperazine was substituted with cyclobutylmethanamine. $^1$H NMR (400 MHz, Methanol-d4+Pyr-d5): δ ppm 6.08-6.56 (m, 12H), 5.45-5.57 (m, 1H), 5.34-5.42 (m, 1H), 4.75-4.83 (m, 1H), 4.60-4.68 (m, 1H), 4.45-4.55 (m, 1H), 4.30-4.40 (m, 1H), 4.26 (br. s., 2H), 4.00-4.11 (m, 1H), 3.84 (br. s., 1H), 3.73 (d, J=11.03 Hz, 1H), 3.61 (t, J=9.26 Hz, 2H), 3.43 (br. s., 1H), 3.20-3.27 (m, 1H), 3.07-3.20 (m, 3H), 2.29-2.58 (m, 4H), 2.16-2.27 (m, 2H), 1.96-2.08 (m, 1H), 1.77-1.94 (m, 6H), 1.62-1.76 (m, 5H), 1.49-1.62 (m, 5H), 1.44-1.49 (m, 1H), 1.39-1.43 (m, 1H), 1.32 (d, J=5.73 Hz, 4H), 1.23 (d, J=6.17 Hz, 3H), 0.93-1.16 (m, 6H). LCMS (ESI): m/z: [M+H] calcd for $C_{52}H_{84}N_3O_{16}$: 1006.5; found 1006.5.

Example 47. Synthesis of Compound 2-CN

Compound 2-CN was synthesized in the manner similar to Compound 2-I (Example 3), except piperazine was substituted with isopropylamine. $^1$H NMR (400 MHz, Methanol-d4+Pyr-d5): δ ppm 6.05-6.57 (m, 14H), 5.44-5.56 (m, 1H), 5.32-5.43 (m, 2H), 4.76 (s, 1H), 4.57-4.67 (m, 1H), 4.43-4.54 (m, 1H), 4.27-4.38 (m, 1H), 4.18 (d, J=2.65 Hz, 2H), 3.96-4.08 (m, 1H), 3.86 (dt, J=13.01, 6.73 Hz, 3H), 3.67-3.75 (m, 1H), 3.48-3.63 (m, 2H), 3.40 (br. s., 1H), 3.24 (d, J=9.70 Hz, 1H), 2.99-3.10 (m, 1H), 2.31-2.51 (m, 3H), 2.17-2.26 (m, 2H), 1.93-2.04 (m, 1H), 1.61-1.92 (m, 7H), 1.54-1.59 (m, 1H), 1.51-1.54 (m, 1H), 1.48-1.51 (m, 1H), 1.43-1.48 (m, 1H), 1.39-1.43 (m, 1H), 1.36-1.39 (m, 1H), 1.33-1.36 (m, 1H), 1.31 (d, J=6.17 Hz, 3H), 1.23 (d, J=6.17 Hz, 3H), 1.13 (br. s., 2H), 1.11 (br. s., 2H), 1.10 (s, 1H), 1.08 (s, 2H), 1.05 (br. s., 2H), 1.03 (s, 4H), 1.01 (br. s., 3H). LCMS (ESI): m/z: [M+Na] calcd for $C_{50}H_{81}N_3O_{16}Na$: 1002.5; found 1002.5.

Example 48. Synthesis of Compound 2-CO

Compound 2-CO was synthesized in the manner similar to Compound 2-I (Example 3), except piperazine was substituted with isobutylamine. $^1$H NMR (400 MHz, Methanol-d4+Pyr-d5): δ ppm 6.06-6.57 (m, 15H), 5.44-5.56 (m, 1H), 5.33-5.42 (m, 2H), 4.77 (s, 1H), 4.57-4.68 (m, 1H), 4.44-4.54 (m, 1H), 4.33 (br. s., 1H), 4.22 (br. s., 2H), 3.99-4.09 (m, 1H), 3.83 (br. s., 1H), 3.72 (d, J=11.03 Hz, 1H), 3.57 (t, J=9.48 Hz, 2H), 3.36-3.46 (m, 1H), 3.24 (d, J=9.26 Hz, 1H), 3.09 (d, J=9.26 Hz, 1H), 2.87-3.03 (m, 3H), 2.34 (d, J=9.70 Hz, 3H), 2.16-2.28 (m, 2H), 2.01 (br. s., 1H), 1.77-1.92 (m, 3H), 1.60-1.77 (m, 4H), 1.55-1.60 (m, 1H), 1.52-1.55 (m, 2H), 1.49-1.52 (m, 1H), 1.44-1.49 (m, 1H), 1.39-1.43 (m, 1H), 1.36-1.39 (m, 1H), 1.33-1.36 (m, 1H), 1.31 (d, J=5.73 Hz, 3H), 1.23 (d, J=6.62 Hz, 3H), 1.12 (d, J=6.17 Hz, 3H), 1.04 (d, J=7.06 Hz, 3H). LCMS (ESI): m/z: [M+Na] calcd for $C_{51}H_{83}N_3O_{16}Na$: 1016.5; found 1016.5.

Example 49. Synthesis of Compound 2-CP

Compound 2-CP was synthesized in the manner similar to Compound 2-I (Example 3), except piperazine was substituted with cyclohexylamine. $^1$H NMR (400 MHz, Methanol-d4+Py-d5): δ ppm 6.08-6.63 (m, 13H), 5.53 (d, J=5.29 Hz, 2H), 4.74 (s, 1H), 4.64 (br. s., 1H), 4.52 (t, J=9.92 Hz, 1H), 4.21-4.43 (m, 3H), 4.00-4.14 (m, 3H), 3.84 (t, J=9.26 Hz, 2H), 3.73 (d, J=11.03 Hz, 1H), 3.52-3.69 (m, 3H), 3.37-3.45 (m, 2H), 3.23 (d, J=9.70 Hz, 2H), 2.76 (d, J=7.50 Hz, 1H), 2.53-2.62 (m, 1H), 2.32-2.50 (m, 3H), 2.16-2.29 (m, 2H), 2.02 (dd, J=16.32, 10.14 Hz, 2H), 1.83-1.96 (m, 4H), 1.62-1.82 (m, 6H), 1.45-1.61 (m, 8H), 1.28-1.44 (m, 7H), 1.23 (d, J=6.62 Hz, 4H), 1.07-1.19 (m, 7H), 1.04 (d, J=7.06 Hz, 6H). LCMS (ESI): m/z: [M+Na] calcd for $C_{53}H_{85}N_3O_{16}Na$: 1042.6; found 1042.6.

Example 50. Synthesis of Compound 2-CQ

Compound 2-CQ was synthesized in the manner similar to Compound 2-I (Example 3), except piperazine was substituted with 2-(4-phenylpiperazin-1-yl)ethan-1-amine. $^1$H NMR (400 MHz, Methanol-d4+Py-d5): δ ppm 6.97-7.06 (m, 1H), 6.87 (d, J=8.38 Hz, 3H), 6.76 (t, J=7.06 Hz, 1H), 6.10-6.59 (m, 12H), 5.52 (d, J=5.29 Hz, 1H), 4.76 (s, 1H), 4.65 (br. s., 1H), 4.52 (t, J=10.36 Hz, 1H), 4.23-4.42 (m, 2H), 4.03-4.18 (m, 2H), 3.77-3.91 (m, 1H), 3.59-3.76 (m, 1H), 3.34-3.49 (m, 4H), 3.18-3.26 (m, 1H), 2.96-3.14 (m, 5H), 2.77 (d, J=7.50 Hz, 1H), 2.30-2.65 (m, 11H), 2.16-2.28 (m, 2H), 1.96-2.10 (m, 1H), 1.63-1.93 (m, 6H), 1.36-1.61 (m, 6H), 1.34 (br. s., 3H), 1.23 (d, J=6.17 Hz, 3H), 1.12 (d, J=6.17 Hz, 7H). LCMS (ESI): m/z: [M+H] calcd for $C_{59}H_{92}N_5O_{16}$: 1126.65; found 1126.6.

Example 51. Synthesis of Compound 2-CR

Compound 2-CR was synthesized in the manner similar to Compound 2-I (Example 3), except piperazine was substituted with cyclopentylamine. $^1$H NMR (400 MHz, Methanol-d4+Pyr-d5): δ ppm 6.03-6.60 (m, 13H), 5.48 (d, J=5.29 Hz, 2H), 5.35 (dd, J=14.33, 10.36 Hz, 2H), 4.68 (s, 1H), 4.59 (br. s., 1H), 4.47 (t, J=9.92 Hz, 1H), 4.29 (t, J=9.48 Hz, 1H), 4.15-4.24 (m, 1H), 3.91-4.09 (m, 3H), 3.80 (t, J=9.92 Hz, 1H), 3.69 (d, J=10.58 Hz, 1H), 3.55 (t, J=9.92 Hz, 1H), 3.33-3.40 (m, 2H), 3.20 (br. s., 1H), 2.74 (d, J=8.38 Hz, 1H), 2.27-2.54 (m, 4H), 2.13-2.25 (m, 2H), 1.60-2.04 (m, 10H), 1.35-1.58 (m, 11H), 1.26-1.34 (m, 5H), 1.21 (d, J=6.62 Hz, 3H), 1.10 (d, J=6.17 Hz, 3H), 1.02 (d, J=7.06 Hz, 3H). LCMS (ESI): m/z: [M+H] calcd for $C_{52}H_{83}N_3O_{15}Na$: 1028.6; Found: 1028.6.

Example 52. Synthesis of Compound 2-CS

Compound 2-CS was synthesized in the manner similar to Compound 2-I (Example 3), except piperazine was substituted with 4-tetrazolo-piperidine. $^1$H NMR (400 MHz, Methanol-d4+Pyr-d5): δ ppm 6.06-6.64 (m, 14H), 5.51 (br. s., 1H), 4.75 (s, 1H), 4.40-4.54 (m, 2H), 4.28-4.39 (m, 3H), 4.24 (d, J=3.53 Hz, 1H), 3.96 (d, J=13.23 Hz, 1H), 3.65-3.87 (m, 4H), 3.38-3.56 (m, 2H), 3.23 (d, J=9.70 Hz, 1H), 3.14 (br. s., 1H), 2.84 (t, J=12.13 Hz, 1H), 2.28-2.52 (m, 2H), 2.16-2.27 (m, 2H), 1.78-2.08 (m, 8H), 1.62-1.77 (m, 3H), 1.29-1.61 (m, 6H), 1.26 (d, J=6.17 Hz, 3H), 1.22 (d, J=6.17 Hz, 3H), 1.10 (d, J=6.62 Hz, 3H), 1.03 (d, J=7.06 Hz, 3H). LCMS (ESI): m/z: [M+Na] calcd for $C_{53}H_{83}N_7O_{16}Na$: 1096.59; found 1096.6.

Synthesis of 4-tetrazolo-piperidine

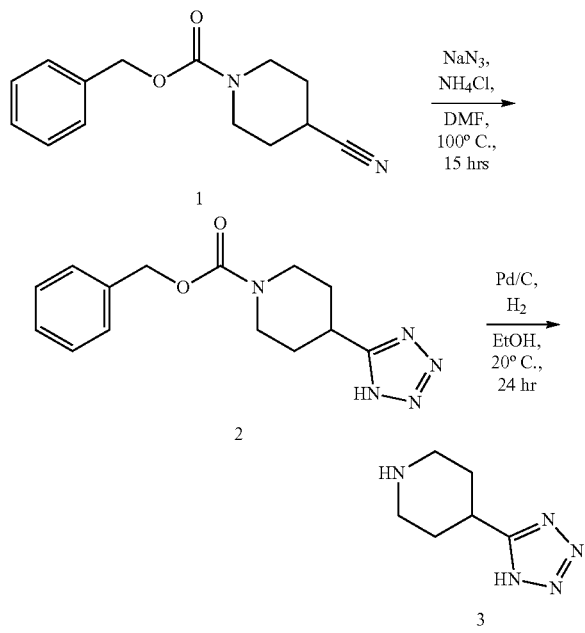

Step 1: NH$_4$Cl (3.28 g, 61.41 mmol, 3.00 equiv.) and NaN$_3$ (3.99 g, 61.41 mmol, 3.00 equiv.) were added to a solution of compound 1 (5.00 g, 20.47 mmol, 1.00 equiv.) in DMF (50.00 mL) and the resulting mixture was stirred at 100° C. for 15 hrs. The reaction mixture was poured into H$_2$O (300 mL), and extracted with EtOAc (200 mL*3). Combined the organic phases were washed with brine (100 mL*5), dried over Na$_2$SO$_4$, filtered. Concentration under reduced pressure resulted in 4.6 g of 2 as light yellow oil which was submitted to the next step with out further purification. $^1$H NMR (400 MHz, CDCl$_3$): δ ppm 7.34-7.28 (m, 5H), 5.15 (s, 1H), 4.25-4.21 (m, 2H), 3.32-3.30 (m, 1H), 3.29-3.26 (m, 2H), 2.13-2.04 (m, 2H), 1.88-1.79 (m, 2H). LCMS (ESI): m/z: [M+Na] calcd for $C_{14}H_{17}N_5O_2Na$; 310.14; found 310.0.

Step 2: A mixture of compound 2 (2.60 g, 9.05 mmol, 1.00 equiv.) and Pd/C (600.00 mg, 50% H$_2$O) in EtOH (120.00 mL) was stirred at 20° C. under H$_2$ for 24 hrs. The resulting mixture was filtered through celite, washed with MeOH: H$_2$O (5:1, about 200 mL), and concentrated under reduced pressure to give 1.0 g of compound 3 as white solid. $^1$H NMR (400 MHz, D20): δ ppm 3.49-3.46 (m, 2H), 3.29-3.26 (m, 1H), 3.21-3.15 (m, 2H), 2.27-2.24 (m, 2H), 2.05-1.96 (m, 2H). LCMS (ESI): m/z: [M+H] calcd for $C_6H_{12}N_5$: 153.10; found 154.1.

Example 53. Synthesis of Compound 2-AW

Compound 2-AW was synthesized in the manner similar to Compound 2-I (Example 3), except piperazine was substituted with N-(3-propylamino)morpholine. $^1$H NMR (400 MHz, Methanol-d4+Pyr-d5): δ ppm 8.67-8.85 (m, 1H), 6.10-6.61 (m, 12H), 5.55 (d, J=6.53 Hz, 1H), 4.86 (s, 1H), 4.64-4.77 (m, 1H), 4.55 (t, J=10.29 Hz, 1H), 4.27-4.45 (m, 2H), 4.08-4.22 (m, 1H), 3.88 (t, J=9.54 Hz, 1H), 3.64-3.80 (m, 2H), 3.59 (t, J=4.27 Hz, 5H), 3.43-3.52 (m, 1H), 3.37 (br. s., 1H), 3.12-3.30 (m, 4H), 2.59 (dd, J=14.31, 4.77 Hz, 1H), 2.35-2.54 (m, 2H), 2.18-2.33 (m, 9H), 2.00-2.14 (m, 1H), 1.81-1.97 (m, 3H), 1.44-1.79 (m, 10H), 1.30-1.41 (m, 4H), 1.22-1.30 (m, 3H), 1.14 (d, J=6.53 Hz, 3H), 1.07 (d, J=7.03 Hz, 3H). LCMS (ESI): m/z: [M+H] calcd for $C_{54}H_{89}N_4O_{17}$: 1065.61; found 1065.7.

Example 54. Synthesis of Compound 2-AT

Compound 2-AT was synthesized in the manner similar to Compound 2-I (Example 3), except piperazine was substituted with (1S,4S)-2-oxa-5-azabicyclo[2.2.1]heptane. $^1$H NMR (400 MHz, Methanol-d4+Pyr-d5): δ ppm 6.14-6.63 (m, 12H), 5.54 (d, J=5.02 Hz, 2H), 4.76 (s, 1H), 4.61-4.71 (m, 2H), 4.46-4.59 (m, 2H), 4.31-4.45 (m, 2H), 4.18-4.28 (m, 1H), 4.16 (br. s., 1H), 3.96 (d, J=7.53 Hz, 1H), 3.86 (t, J=10.04 Hz, 1H), 3.70-3.82 (m, 2H), 3.45-3.53 (m, 1H), 3.26 (d, J=10.04 Hz, 1H), 3.16 (s, 1H), 2.96 (d, J=8.03 Hz, 1H), 2.42-2.53 (m, 2H), 2.35-2.41 (m, 1H), 2.21-2.31 (m, 2H), 1.98-2.09 (m, 1H), 1.64-1.97 (m, 8H), 1.42-1.63 (m, 5H), 1.31-1.39 (m, 4H), 1.26 (d, J=6.53 Hz, 3H), 1.15 (d, J=6.02 Hz, 3H), 1.07 (d, J=7.53 Hz, 3H). LCMS (ESI): m/z: [M+Na] calcd for $C_{52}H_{81}N_3O_{17}Na$: 1042.56; found 1042.6.

Example 55. Synthesis of Compound 2-CL

Compound 2-CL was synthesized in the manner similar to Compound 2-I (Example 3), except piperazine was substituted with allyl piperidine-4-carboxylate.

Deprotection Step. To a solution of allyl carboxylate of 2-CL (500.00 mg, 458.59 umol, 1.00 equiv.) in DMF (13.00 mL) was added 2-sulfanylbenzoic acid (141.42 mg, 917.18 umol, 2.00 equiv.) was added Pd(PPh$_3$)$_4$ (264.96 mg, 229.29 umol, 0.50 equiv.) under N$_2$ protected. The mixture was stirred at 25° C. for 1 hr, and filtered. The resulting mixture was purified by prep-HPLC (FA) chromatography to give 50.00 mg of 2-CL as a light yellow solid. $^1$H NMR (400 MHz, Methanol-d4+Pyr-d5): δ ppm 6.03-6.56 (m, 13H), 5.47 (d, J=7.06 Hz, 1H), 5.35 (dd, J=14.11, 10.58 Hz, 1H), 4.72 (s, 1H), 4.39-4.57 (m, 1H), 4.25-4.37 (m, 1H), 4.10-4.25 (m, 2H), 3.75-3.89 (m, 1H), 3.57-3.73 (m, 2H), 3.39-3.48 (m, 1H), 3.32-3.38 (m, 1H), 3.17-3.25 (m, 1H), 2.73-2.89 (m, 2H), 2.29-2.49 (m, 3H), 2.14-2.25 (m, 1H), 1.79-1.92 (m, 5H), 1.59-1.76 (m, 6H), 1.29-1.58 (m, 6H), 1.26 (d, J=5.73 Hz, 3H), 1.21 (d, J=6.17 Hz, 3H), 1.10 (d, J=6.62 Hz, 3H), 1.03 (d, J=7.06 Hz, 3H). LCMS (ESI): m/z: [M+Na] calcd for C$_{53}$H$_{85}$N$_3$O$_{18}$Na: 1072.59; found 1072.6.

Example 56. Synthesis of Compound 2-CT

Compound 2-CT was synthesized in the manner similar to Compound 2-I (Example 3) and 2-CL (Example 55), except piperazine was substituted with allyl-4-(aminomethyl)benzoate. Two peaks were isolated upon deprotection and prep-HPLC purification. Peak one: $^1$H NMR (400 MHz, Methanol-d4+Pyr-d5): δ ppm 8.03 (d, J=7.50 Hz, 2H), 7.32 (d, J=7.06 Hz, 2H), 6.06-6.52 (m, 11H), 4.75 (s, 1H), 4.60-4.72 (m, 1H), 4.48 (d, J=16.32 Hz, 1H), 4.26-4.41 (m, 2H), 4.08-4.25 (m, 1H), 3.86 (br. s., 1H), 3.62-3.81 (m, 3H), 3.47 (br. s., 1H), 3.16 (br. s., 1H), 2.33-2.52 (m, 3H), 2.19-2.27 (m, 2H), 2.03 (br. s., 1H), 1.89 (d, J=14.11 Hz, 2H), 1.64-1.78 (m, 2H), 1.33-1.62 (m, 6H), 1.30 (d, J=5.73 Hz, 3H), 1.23 (d, J=6.17 Hz, 3H), 1.11 (d, J=6.17 Hz, 3H), 1.04 (d, J=6.62 Hz, 3H). LCMS (ESI): m/z: [M+H] calcd for C$_{55}$H$_{82}$N$_3$O$_{18}$: 1072.55; found 1072.50. Peak 2: $^1$H NMR (400 MHz, Methanol-d4+Py-d5): δ ppm 8.10 (d, J=6.62 Hz, 3H), 7.36 (d, J=7.50 Hz, 3H), 5.82-6.78 (m, 9H), 4.93 (br. s., 1H), 4.60-4.84 (m, 2H), 4.45 (br. s., 3H), 4.22 (br. s., 2H), 3.81-4.11 (m, 4H), 3.70 (br. s., 2H), 2.42-2.60 (m, 3H), 2.25 (br. s., 1H), 1.40-2.14 (m, 14H), 1.19-1.36 (m, 7H), 1.10 (br. s., 4H), 0.92-1.06 (m, 3H). LCMS (ESI): m/z: found 1054.40.

Example 57. Synthesis of Compound 2-AR

Compound 2-AR was synthesized in the manner similar to Compound 2-I (Example 3), except piperazine was substituted with 8-oxa-3-azabicyclo[3.2.1]octane. $^1$H NMR (400 MHz, Methanol-d4+Pyr-d5): δ ppm 6.05-6.51 (m, 8H), 5.47 (br. s., 1H), 5.34-5.43 (m, 3H), 4.79 (s, 1H), 4.61 (br. s., 1H), 4.46-4.54 (m, 1H), 4.36 (d, J=9.26 Hz, 1H), 4.10-4.27 (m, 3H), 3.76-3.87 (m, 1H), 3.60-3.75 (m, 3H), 3.37-3.45 (m, 1H), 3.33 (d, J=3.97 Hz, 1H), 3.24 (br. s., 2H), 2.99 (d, J=12.35 Hz, 2H), 2.29-2.46 (m, 1H), 2.14-2.28 (m, 1H), 1.79-1.96 (m, 2H), 1.60-1.78 (m, 5H), 1.49-1.59 (m, 3H), 1.37-1.49 (m, 2H), 1.16-1.32 (m, 6H), 1.00-1.13 (m, 6H). LCMS (ESI): m/z: [M+Na] calcd for C$_{53}$H$_{83}$N$_3$O$_{17}$Na: 1056.57; found 1056.6.

Example 58. Synthesis of Compound 2-CU

Compound 2-CU was synthesized in the manner similar to Compound 2-I (Example 3), except piperazine was substituted with methan-d3-amine. $^1$H NMR (400 MHz, Methanol-d4+Pyr-d5): δ ppm 6.20-6.70 (m, 13H), 5.64 (d, J=6.17 Hz, 2H), 4.95 (s, 1H), 4.79 (d, J=5.73 Hz, 1H) 4.64 (t, J=10.36 Hz, 1H,) 4.34-4.55 (m, 3H), 4.14-4.32 (m, 1H), 3.97 (br. s., 1H), 3.71-3.91 (m, 3H), 3.58 (dd, J=9.26, 6.17 Hz, 2H), 3.38 (d, J=9.26 Hz, 1H), 3.28 (d, J=7.50 Hz, 1H), 2.92-3.08 (m, 1H), 2.79 (d, J=6.62 Hz, 1H), 2.45-2.69 (m, 3H), 2.24-2.42 (m, 2H) 2.09-2.22 (m, 1H), 1.90-2.06 (m, 3H), 1.75-1.88 (m, 3H), 1.52-1.73 (m, 6H), 1.42-1.51 (m, 4H), 1.37 (d, J=6.17 Hz, 3H), 1.25 (d, J=5.73 Hz, 3H), 1.18 (d, J=7.06 Hz, 3H). LCMS (ESI): m/z: [M+Na] calcd for C$_{48}$H$_{74}$D3N$_3$O$_{16}$Na: 977.55; found 977.5.

Example 59. Synthesis of Compound 2-CJ

Compound 2-CJ was synthesized in the manner similar to Compound 2-I (Example 3) and 2-CL (Example 55), except piperazine was substituted with allyl (3-aminopropyl)carbamate. LCMS (ESI): m/z: [M+H] found 995.5.

Example 60. Synthesis of Compound 2-CK

Compound 2-CK was synthesized in the manner similar to Compound 2-I (Example 3), except piperazine was substituted with 6-oxa-2-azaspiro[3.4]octane. LCMS (ESI): m/z: [M+Na] found 1056.3.

Example 61. Synthesis of Compound 2-Q

Compound 2-Q was synthesized in the manner similar to Compound 2-I (Example 3), except piperazine was substituted with 2-(1H-1,2,4-triazol-1-yl)ethan-1-amine. LC-MS: Calculated (C$_{51}$H$_{80}$N$_6$O$_{16}$+H)$^+$: 1033.56. Observed: 1033.50.

Example 62. Sample Characterization Data of Ureas 2

TABLE 2

Sample Characterization Data of Ureas 2

| Compound ID | Isolated Yield from 1-2 | Observed Mass | LC retention time (min) | LC Conditions | LC Purity |
|---|---|---|---|---|---|
| 2-B | 7% | 988.6 (M + Na) | 7.39 | A | 98% |
| 2-C | 3% | 1028.6 (M + Na) | 7.88 | A | 97% |
| 2-E | 6% | 1030.6 (M + Na) | 7.46 | A | 99% |
| 2-J | 10% | 1043.6 (M + Na) | 6.81 | A | 97% |
| 2-D | 24% | 1000.5 (M + Na) | 7.4 | A | 97% |
| 2-F | 13% | 1009.6 (M + H) | 6.87 | A | 96% |
| 2-I | 23% | 1029.6 (M + Na) | 6.8 | A | 98% |
| 2-T | 10% | 1065.6 (M + Na) | 7.07 | A | 99% |
| 2-U | 18% | 1051.6 (M + Na) | 6.96 | A | 99% |
| 2-Y | 23% | 1018.5 (M + Na) | 7.37 | A | 99% |
| 2-AG | 6% | 1014.5 (M + Na) | 7.97 | A | 99% |
| 2-AB | 8% | 1071.6 (M + Na) | 7.55 | A | 99% |
| 2-AF | 9% | 1051.7 (M + H) | 7.41 | A | 99% |
| 2-AI | 19% | 1014.5 (M + Na) | 7.55 | A | 99% |
| 2-BC | 38% | 1033.4 (M + Na) | 4.55 | C | 98% |

Conditions for LC analysis: Conditions A: Agilent 1260, 6120 MS, Column: Phenomenex Luna 5 μm C18(2) 100 Å 50×2.0 mm, 0.8 mL/min, column temperature: 40° C., mobile Phase: A: 4 L H$_2$O (with 1.5 mL TFA) B: 4 L Acetonitrile (with 0.75 mL TFA), Gradient (min, % B): 0, 10; 0.4, 10; 3.40, 100; 3.85, 100; 3.86, 10. LC purity calculated from the peak area ratio monitoring at 383 nM. Conditions B: Agilent LCMS, Zorbax Eclipse C18 1.8 μM, 2.1×50 mm, 0.4 mL/min, linear gradient from 95:5 to 5:95 H$_2$O, acetonitrile over 8 minutes with each eluent containing 0.1% formic acid. Conditions C: Shimadzu LC-MS system (Shimadzu Co., Japan), Phenomenex Onyx Monolithic C18 column (4.6×50 mm), p/n CHO-7644 (Phenomenex Co.); samples dissolved in DMSO were eluted using a linear gradient of 0.1% HCOOH in 100% water (mobile phase A) to 0.1% HCOOH acetonitrile in 100% acetonitrile (mobile phase B).

Example 63. C16-Carbamates 3
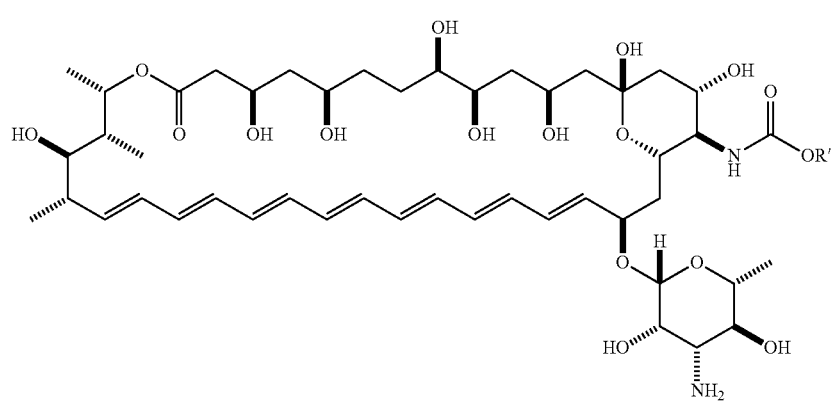
Scheme 3: Preparation of 3
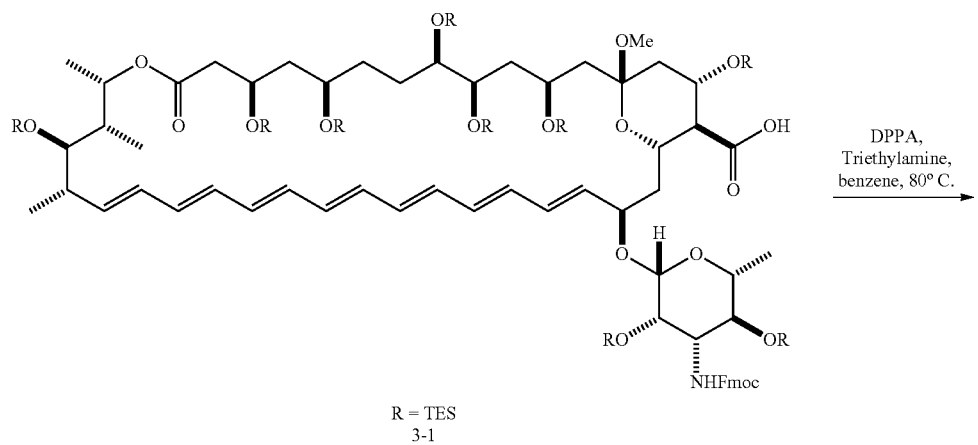
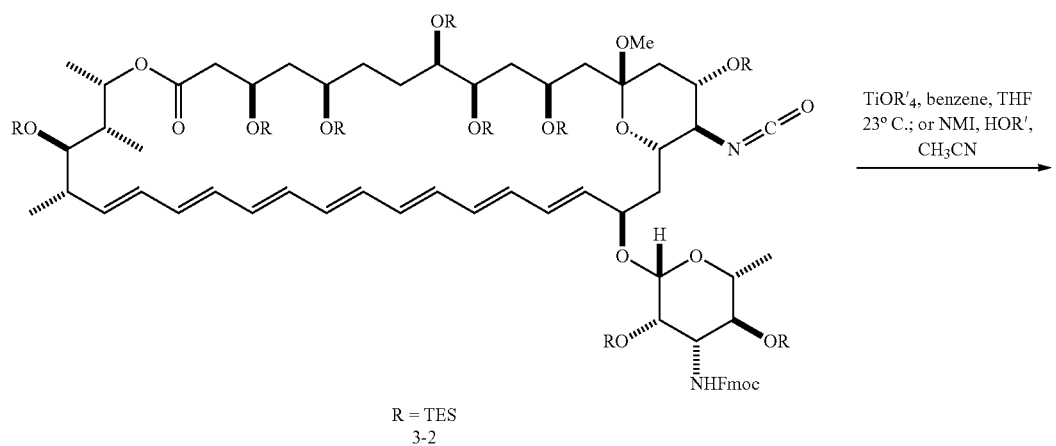

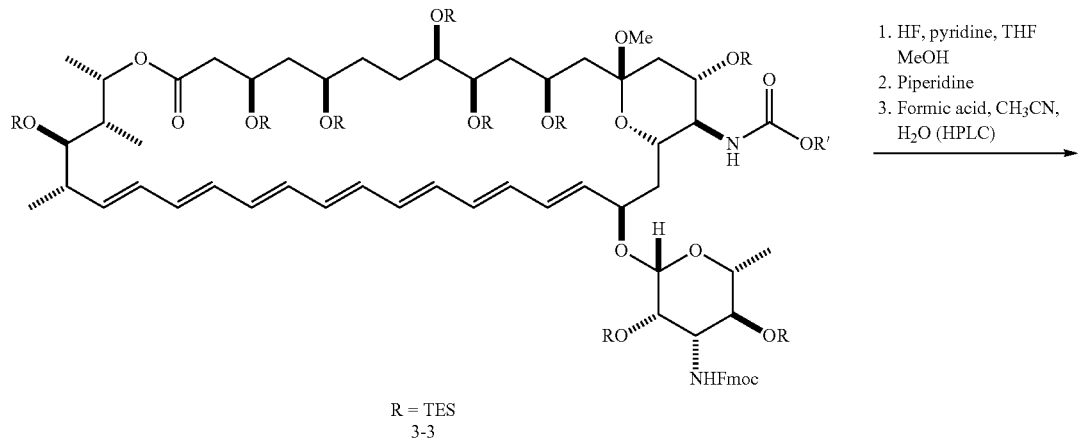

R = TES
3-3

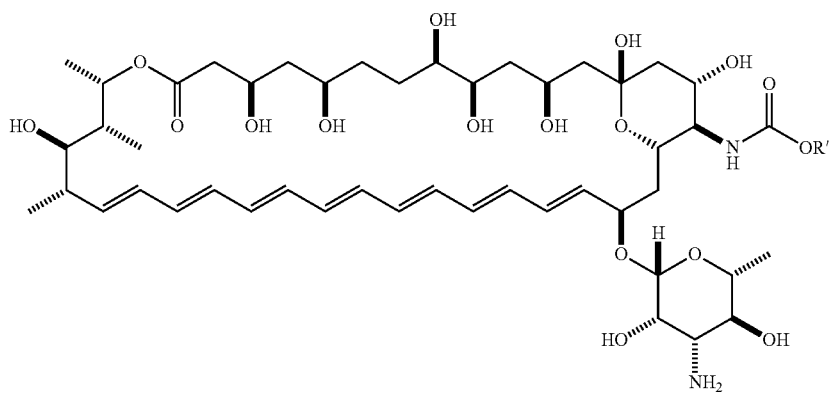

3

Preparation of 3-2: To a 40 mL vial was added 3-1 (602.6 mg, 275.3 µmol, 1 eq.), prepared as described in Driver et al., *J Chem Soc Perkin Trans* 3155-7 (1992), and benzene (13.7 mL). Triethylamine (115 µL, 0.822 mmol, 3 eq.) was added followed by DPPA (71 µL, 33.0 mmol, 1.2 eq.). The reaction was then placed in a preheated heating block at 80° C. and allowed to stir for 3.5 hours. The reaction was then transferred to a 125 mL separatory funnel with water (25 mL) and diethyl ether (50 mL). The layers were separated and the organic layer was washed with brine (25 mL), dried over $Na_2SO_4$, filtered and concentrated in vacuo. The resulting red/orange oil was then purified by $SiO_2$ chromatography (100:0 to 0:100 Hexane:$Et_2O$) yielding 3-2 as an orange solid (168.7 mg, 0.077 mmol, 28% yield). TLC (hexanes: $Et_2O$ 7:3) $R_f$=0.64, visualized by CAM HRMS (ESI): Calculated for $C_{117}H_{210}N_2O_{18}Si_9$ (M+Na$^+$): 2206.3400, Found: 2206.3413.

Preparation of 3-3-A: To a 1.5 mL vial was added 3-2 (as a stock solution (100 µL of 150 mg in 1.5 mL benzene) 10 mg, 4.57 µmol, 1 eq.), and titanium isopropoxide (as a stock solution (50 µL of 25 µL in 4.6 mL benzene) 0.27 µL, 0.914 µmol, 0.2 eq.) and THF (80 µL). The reaction was then allowed to stir at room temperature for 1 h. The reaction was then diluted with water (1.5 mL) and diethyl ether (1.5 mL). The layers were separated and the organic layer was dried over $Na_2SO_4$, filtered and concentrated in vacuo. The resulting red/orange oil was then purified by $SiO_2$ chromatography (100:0 to 80:20 hexane:$Et_2O$) yielding 3-3-A as an orange solid. TLC (hexanes:$Et_2O$ 7:3), $R_f$=0.51, stained by CAM. LRMS (ESI) 2266.6 (M+Na).

$^1$H NMR (500 MHz, Acetone-d$_6$): δ 7.88 (d, J=7.5 Hz, 2H), 7.70 (d, J=7.5 Hz, 2H), 7.43 (t, J=7.3 Hz, 2H), 7.36-7.32 (m, 2H), 6.59-6.08 (m, 12H), 6.03 (dd, J=15.5, 6.1 Hz, 1H), 5.51 (dd, J=14.9, 9.5 Hz, 1H), 5.35 (d, J=9.9 Hz, 1H), 4.87 (p, J=6.3 Hz, 1H), 4.77-4.73 (m, 1H), 4.71-4.67 (m, 1H), 4.65 (s, 1H), 4.48 (dd, J=10.5, 6.5 Hz, 1H), 4.37 (dd, J=10.4, 6.5 Hz, 1H), 4.25 (app t, J=6.3 Hz, 2H), 4.18-4.09 (m, 1H 4.07-3.97 (m, 2H), 3.87-3.84 (m, 1H), 3.76 (app dd, J=11.8, 6.9 Hz, 1H), 3.70 (d, J=8.9 Hz, 1H), 3.74-3.66 (m, 2H), 3.47-3.34 (m, 2H), 3.35-3.28 (m, 1H), 3.15 (s, 3H), 2.58 (d, J=6.6 Hz, 1H), 2.47-2.40 (m, 2H), 2.26 (app dd, J=15.6, 7.4 Hz, 2H), 2.20-2.15 (m, 1H), 1.94-1.85 (m, 4H), 1.84-1.80 (d, J=13.1 Hz, 3H), 1.79-1.68 (m, 4H), 1.68-1.61 (d, J=9.3 Hz, 2H), 1.54-1.56 (s, 1H), 1.26 (app dd, J=6.2, 3.2 Hz, 6H), 1.22 (d, J=6.2 Hz, 3H), 1.18 (d, J=6.0 Hz, 3H), 1.14-0.83 (m, 87H), 0.81-0.53 (m, 54H).

Preparation of 3-A: Treatment of 3-3-A with HF, pyridine, evaporation of the solution and treatment of the residue with piperidine in DMF provides the carbamate 3-A after purification by HPLC with 0.1% to 0.3% formic acid modified $H_2O/CH_3CN$.

Specific Compounds 3

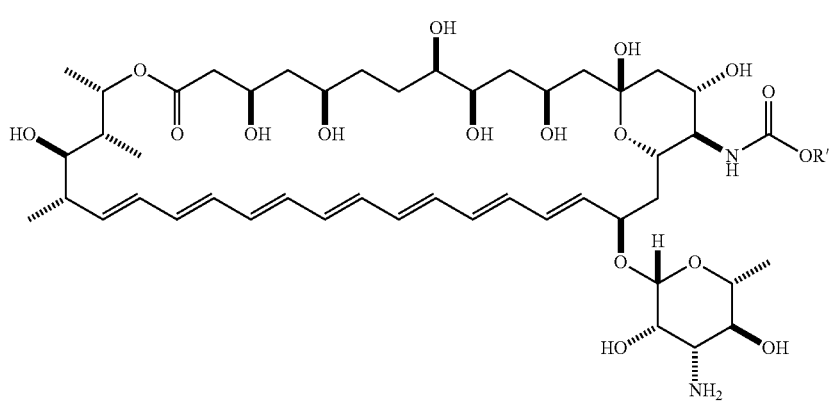

where HOR' is depicted in Table 3:

TABLE 3

| | |
|---|---|
| HO-CH(CH₃)₂ (isopropanol) | A |
| HO-CH₃ (methanol) | B |
| HO-CH₂-C₆H₅ (benzyl alcohol) | C |
| HO-CH₂CH₂-O-CH₂CH₂-O-CH₃ | D |
| HO-CH₂-CH=CH₂ (allyl alcohol) | E |
| HO-CH₂CH₃ (ethanol) | F |
| tetrahydropyran-4-ol | G |
| cyclohexanol | H |
| 1-acetylpiperidin-4-ol | I |

TABLE 3-continued

| | |
|---|---|
| 3-(hydroxymethyl)pyridine | J |
| 3-morpholinopropan-1-ol | K |
| 3-(4-methylpiperazin-1-yl)propan-1-ol | L |
| 3-(3-methoxypyrrolidin-1-yl)propan-1-ol | M |
| 3-(4H-1,2,4-triazol-4-yl)propan-1-ol | N |
| 1-(2-methoxyethyl)piperidin-4-ol | O |

Example 64. C16 Amides
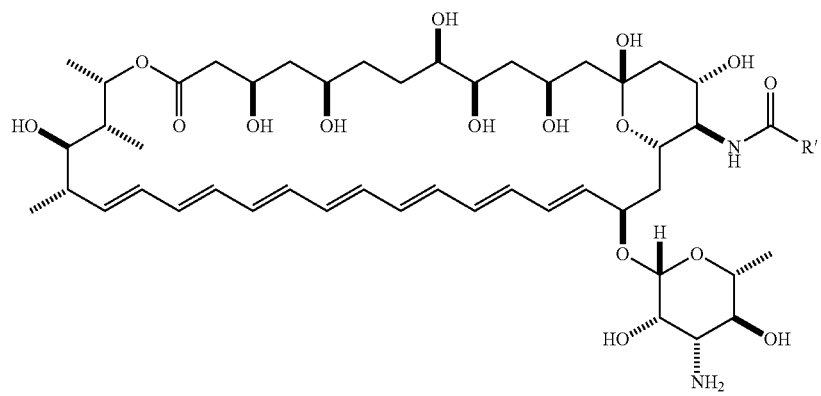
Scheme 4: Preparation of Amides 4:
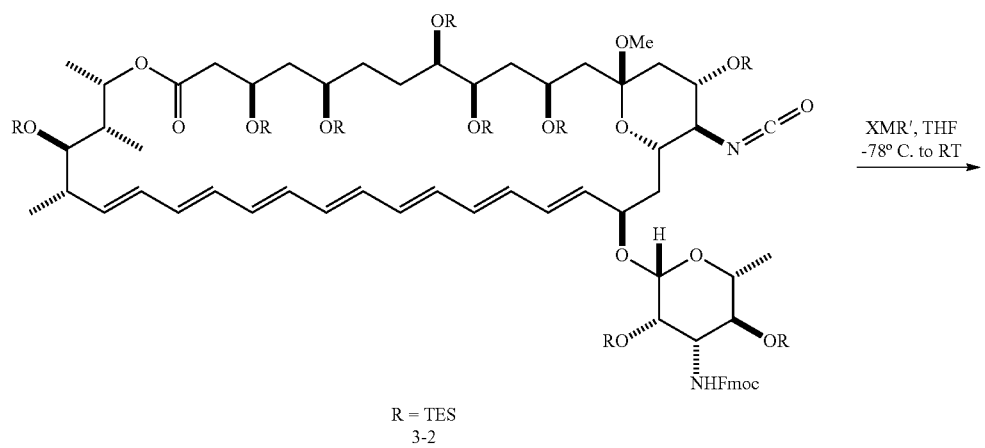
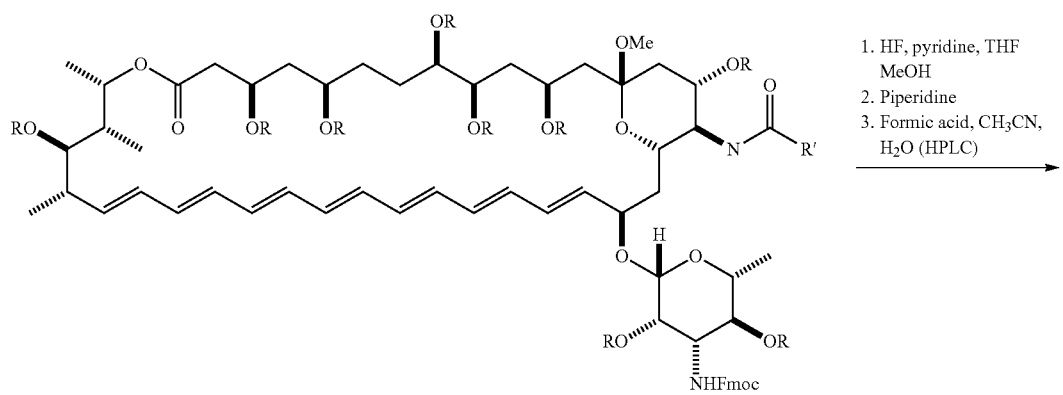

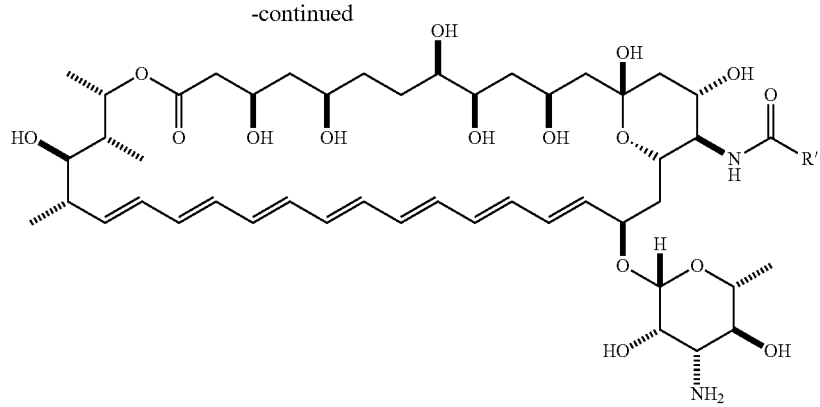

4

Amides 4 are prepared according to the routes described in Scheme 4. Specifically, treatment of the isocyanate 3-2 with organometallic reagents (i.e., organozinc reagents, organomagnesium reagents, organolithium reagents) provides the desired amides intermediates 4-1 according, for example, to the methods described in Carlin and Smith, *J Am Chem Soc* 69: 2007 (1947) or Szczesniak et al., *J Org Chem* 79(23): 11700-13 (2014). Deprotection of the amphotericin derivative is accomplished generally according to the methods of Driver et al., *J Chem Soc Perkin Trans* 3155-7 (1992) allows the isolation of the desired amides 4, as described in Scheme 4.

Specific Compounds 4

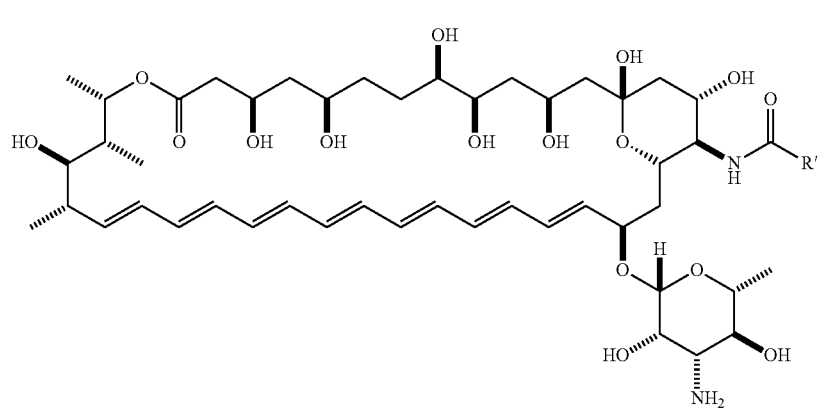

4 where R' and the site of connectivity are depicted in Table 4:

TABLE 4

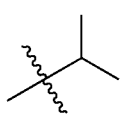 [SMILES: *C(C)C]  A

TABLE 4-continued

  B

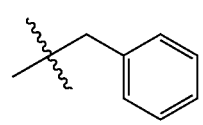 [SMILES: *Cc1ccccc1]  C

TABLE 4-continued

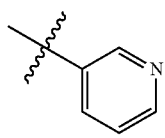 [SMILES: *c1cccnc1]  D

TABLE 4-continued
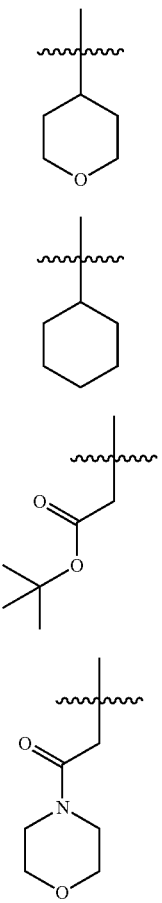
| | |
|---|---|
| E | (tetrahydropyran) |
| F | (cyclohexyl) |
| G | (tert-butyl ester) |
| H | (morpholine amide) |
TABLE 4-continued
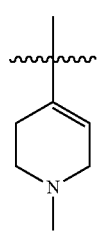 [SMILES: *C1=CCN(C)CC1]
| | |
|---|---|
| I | (N-methyl tetrahydropyridine) |
| J | (N-acetyl piperidine) |
Example 65. C3' Amides and Carbamates 5
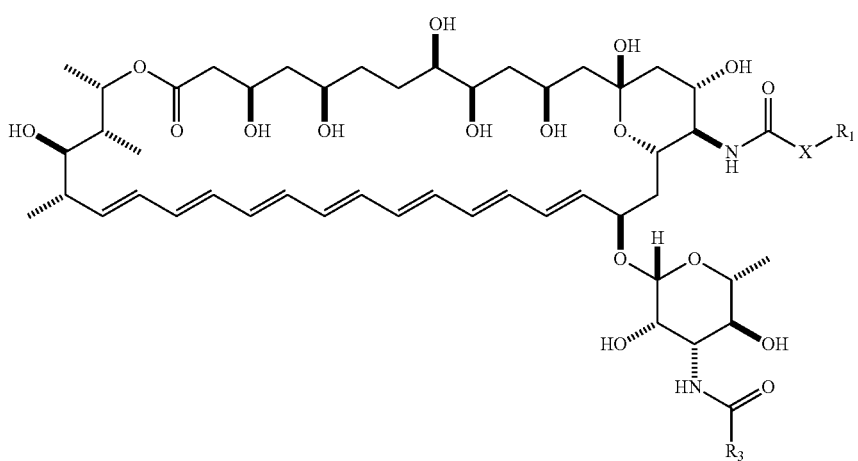
X = O or C or NR$_2$ Scheme 5: Preparation of Amides and Carbamates 5:

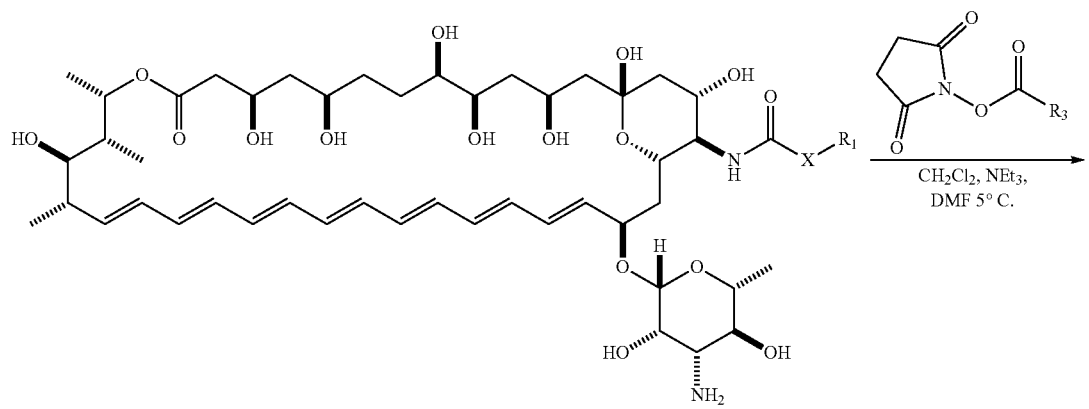

X = O or C or NR$_2$
2, 3, or 4

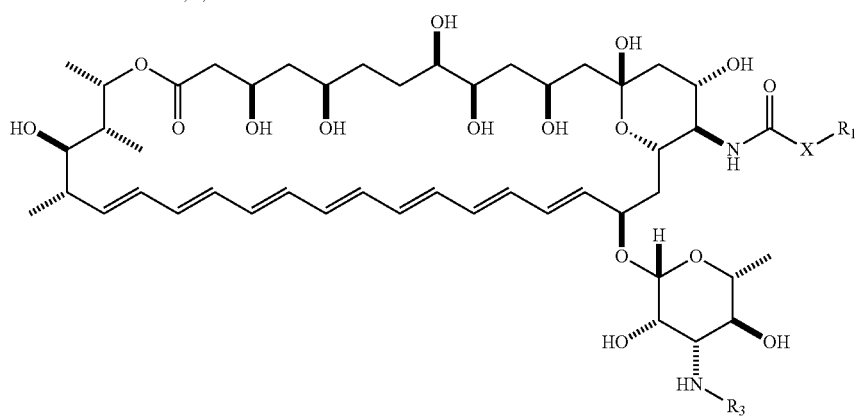

X = O or C or NR$_2$
5

Compounds 5 are accessed from 2-BF (Example 4) according to the procedure established by Wright et al., *J Antibiotics* 35: 911-4 (1982). Specifically, for the synthesis of 5-C, the bis-Fmoc-protected N-hydroxysuccinimide ester of D-lysine (3 equiv., prepared as described in Russ, *J Bioorg Chem* 33: 139 (2007)) and Et$_3$N (1 equiv.) are added to a solution of 2-BF (1 equiv.) in dry DMF. The reaction mixture is kept at 37° C. for 1 h, and then H$_2$O is added. The mixture is extracted with butanol. Organic fractions are combined concentrated. The addition of diethyl ether pro- vides a yellow precipitate, which is filtered off, washed with diethyl ether and purified to produce 5-C. In examples where the Fmoc protecting group is not cleaved from the substrate during the coupling reaction, it can be efficiently removed using 1,5-diazabicyclo[4.3.0]non-5-ene (DBN) or piperidine in DMF, followed by reprecipitation by addition of the DMF mixture to a large volume of diethyl ether.

Alternatively, Compounds 5 can be prepared by the following procedure:

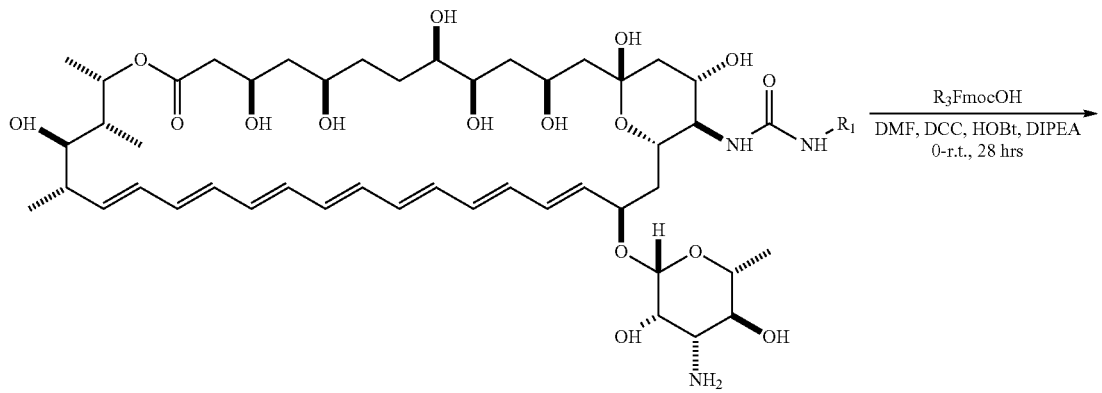

Compound 2.

-continued
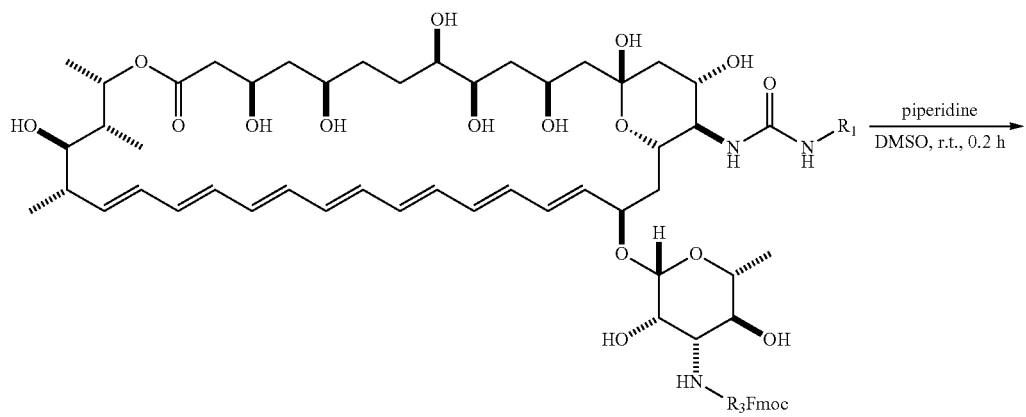
5-1
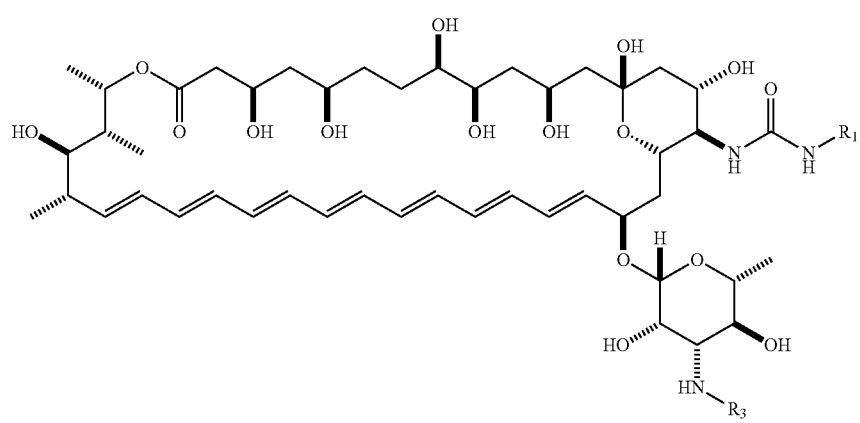
Compound 5.
Specific Compounds 5
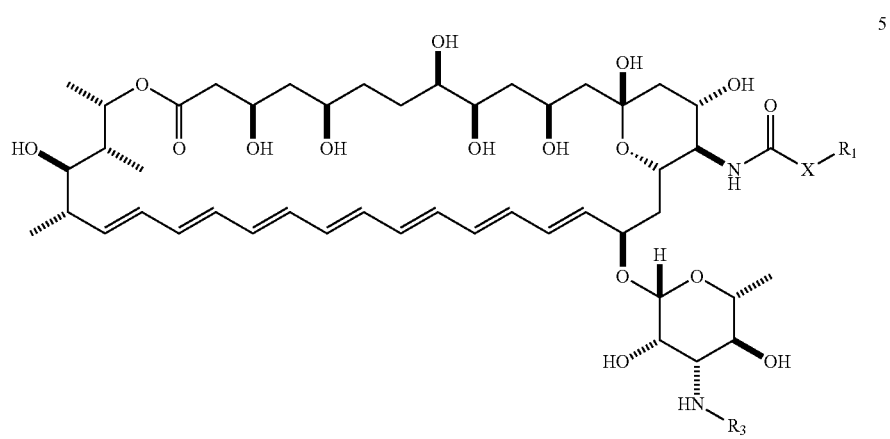
5
X = O or C or NR$_2$ where R³ defined according to the structure above are depicted in Table 5, and XR₁ defined according to the structure above are depicted in Table 6:

TABLE 5

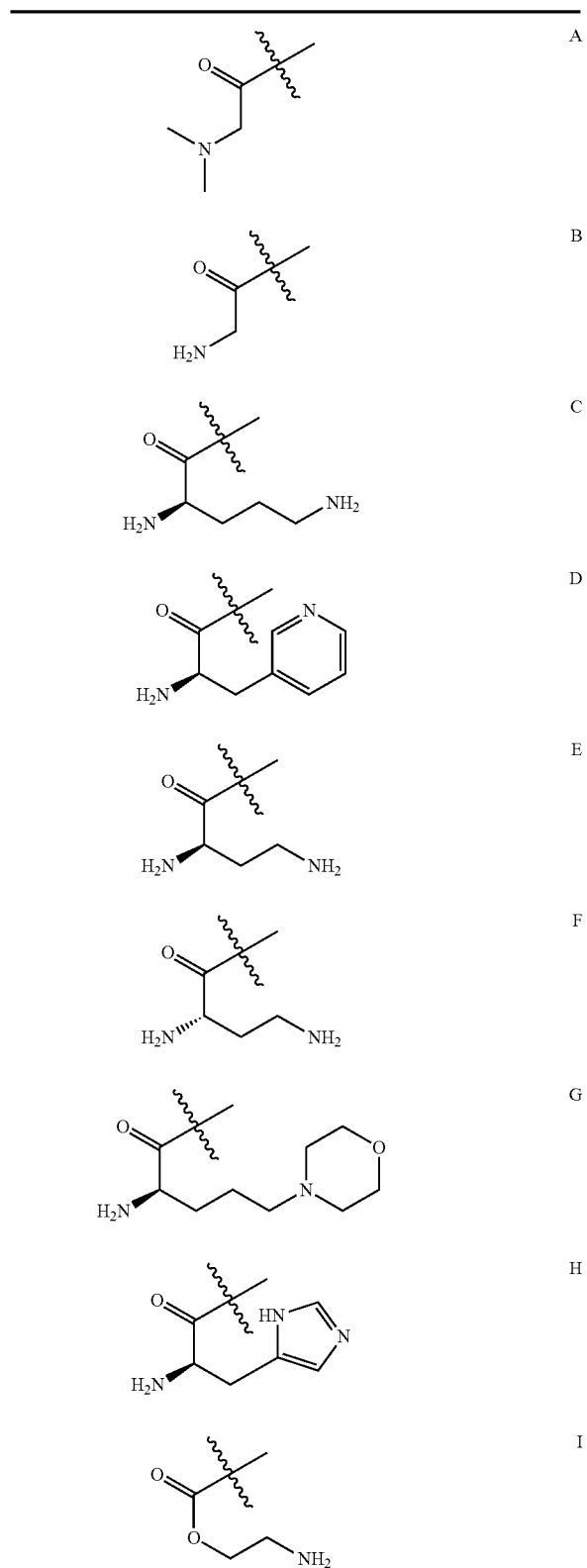

TABLE 5-continued

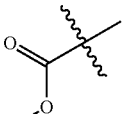  J

TABLE 6

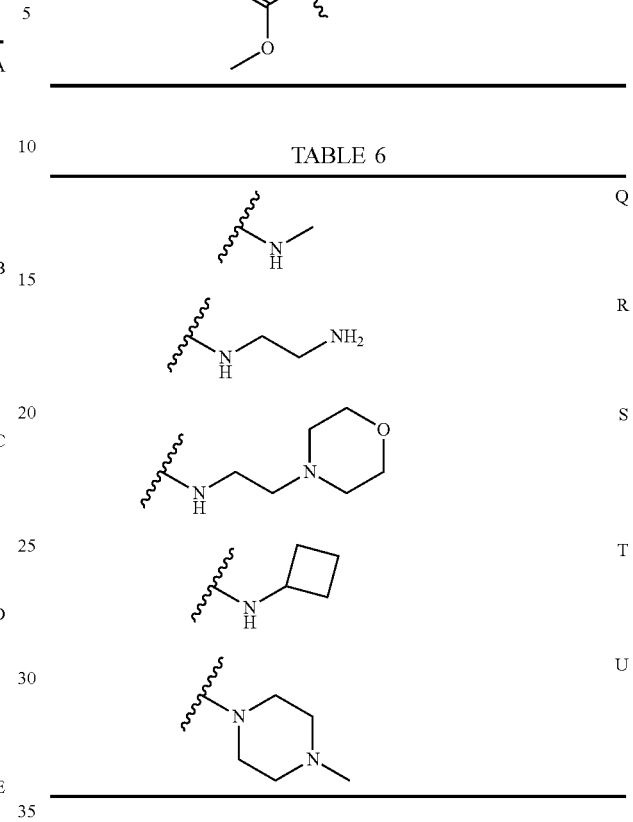

Example 66. Synthesis of Compound 5-DT

Step. 1: The mixture of compound (R)-2-((((9H-fluoren-9-yl)methoxy)carbonyl)amino)-3-(pyridin-3-yl)propanoic acid (301.00 mg, 774.94 umol, 1.65 equiv.) and HOBt (126.92 mg, 939.32 umol, 2.00 equiv.) in DMF (0.6 mL) was prepared and cooled to 0° C., DCC (145.36 mg, 704.49 umol, 142.51 uL, 1.50 equiv.) was added. The reaction mixture was stirred at 0° C. for 1 hr, the residue of DCU was filtered, the obtained eluate was added to the solution of 2-AG (Example 25) (466.00 mg, 469.66 umol, 1.00 equiv.) in DMF (5.00 mL), then DIPEA (242.80 mg, 1.88 mmol, 328.11 uL, 4.00 equiv.) was added to the reaction mixture dropwise. The reaction was stirred at r.t. for 28 hrs. The mixture was poured into MTBE (150 mL), and then filtered to give 426 mg of intermediate 5-1 as yellow solid which was used to next step.

Step 2: The mixture of intermediate 5-1 (247.00 mg, 181.27 μmol, 1.00 equiv.) in DMSO (3.00 mL) was added piperidine (154.35 mg, 1.81 μmol, 0.01 equiv.) at r.t. The mixture was stirred at r.t. for 0.2 hr. The mixture was filtered and purified by prep-HPLC (FA) to give 31.40 mg of Compound 5-DT as yellow solid. ¹H NMR (400 MHz, Methanol-d4+Pyr-d5): δ ppm 8.58-8.68 (m, 2H), 8.24-8.34 (m, 2H), 7.67-7.72 (m, 1H), 7.24-7.27 (m, 1H), 6.13-6.45 (m, 13H), 5.09-5.24 (m, 2H), 4.71 (s, 1H), 4.27-4.70 (m, 2H), 4.00-4.27 (m, 3H), 3.79-4.00 (m, 3H), 3.76-3.79 (m, 2H), 3.29-3.76 (m, 3H), 3.19-3.29 (m, 5H), 2.18-2.12 (m, 9H), 1.81-1.83 (m, 5H), 1.52-1.55 (m, 9H), 1.3 (d, J=8 Hz, 3H), 1.20 (d, J=8 Hz, 3H), 1.10 (d, J=8 Hz, 3H), 1.02 (d, J=8 Hz, 3H). LCMS (ESI): m/z: [M+H] calcd for $C_{59}H_{90}N_5O_{17}$: 1140.63; found 1140.60.

Example 67. Synthesis of Compound 5-DR

Compound 5-DR was synthesized in the manner similar to Compound 5-DT (Example 66), except 2-AG (Example 25) was substituted with 2-BG. $^1$H NMR (400 MHz, Methanol-d4+Pyr-d5): δ ppm 8.53 (s, 1H), 8.34 (d, J=3.53 Hz, 1H), 7.76 (d, J=7.50 Hz, 1H), 7.16-7.19 (m, 1H), 6.04-6.58 (m, 13H), 5.30-5.54 (m, 3H), 4.79 (s, 1H), 4.46-4.67 (m, 1H), 4.24-4.39 (m, 2H), 4.04-4.22 (m, 3H), 3.41-3.87 (m, 6H), 3.06-3.28 (m, 5H), 2.55 (d, J=11.03 Hz, 1H), 2.30-2.50 (m, 2H), 2.15-2.29 (m, 2H), 1.36-2.11 (m, 11H), 1.33 (d, J=6.17 Hz, 3H), 1.23 (d, J=6.17 Hz, 3H), 1.12 (d, J=6.62 Hz, 3H), 1.04 (d, J=7.50 Hz, 3H). LCMS (ESI): m/z: [M+H] calcd for $C_{57}H_{89}N_6O_{17}$: 1129.62; found: 1129.60.

Example 68. Synthesis of Compound 5-DS

Compound 5-DS was synthesized in the manner similar to Compound 5-DT (Example 66), except 2-AG (Example 25) was substituted with 2-AF (Example 15). $^1$H NMR (400 MHz, Methanol-d4+Py-d5): δ ppm 8.34 (d, J=4.85 Hz, 1H), 7.74 (s, 4H), 7.72 (s, 4H), 7.69 (br. s., 1H), 7.46 (s, 1H), 7.20-7.23 (m, 2H), 6.37-6.55 (m, 2H), 6.24-6.37 (m, 7H), 6.01-6.24 (m, 4H), 5.48 (d, J=6.17 Hz, 1H), 5.35 (dd, J=14.33, 9.92 Hz, 1H), 4.75 (s, 1H), 4.61 (br. s., 1H), 4.48 (t, J=9.92 Hz, 1H), 4.14-4.35 (m, 1H), 3.97-4.10 (m, 2H), 3.92 (s, 4H), 3.74-3.88 (m, 1H), 3.48-3.72 (m, 8H), 3.32-3.47 (m, 2H), 3.05-3.27 (m, 4H), 2.80-3.00 (m, 1H), 2.37-2.47 (m, 31H), 2.13-2.26 (m, 2H), 1.84 (d, J=4.85 Hz, 2H), 1.65-1.80 (m, 2H), 1.54-1.65 (m, 4H), 1.46-1.53 (m, 17H), 1.29-1.38 (m, 12H), 1.21 (d, J=6.17 Hz, 3H), 1.07-1.12 (m, 4H), 1.02 (d, J=7.06 Hz, 3H). LCMS (ESI): m/z: [M+H] calcd for $C_{61}H_{95}N_6O_{18}$: 1200.66; found: 1200.60.

Example 69. Synthesis of Compound 5-QA

Compound 5-QA was synthesized in the manner similar to Compound 5-DT (Example 66), except 2-AG (Example 25) was substituted with 2-BF (Example 4); and (R)-2-((((9H-fluoren-9-yl)methoxy)carbonyl)amino)-3-(pyridin-3-yl)propanoic acid with NN-dimethylglycine. $^1$H NMR (400 MHz, Methanol-d4+Pyr-d5): δ ppm 6.21-6.79 (m, 13H), 5.73 (d, J=5.73 Hz, 1H), 5.03 (s, 1H), 4.86 (br. s., 1H), 4.73 (t, J=10.14 Hz, 1H), 4.48-4.62 (m, 2H), 4.24-4.43 (m, 3H), 4.04 (t, J=9.70 Hz, 1H,) 3.82-3.99 (m, 3H), 3.69 (dd, J=8.82, 6.17 Hz, 1H), 3.53 (d, J=10.14 Hz, 1H), 3.44-3.49 (m, 4H) 3.41 (d, J=9.26 Hz, 1H), 2.98-3.15 (m, 2H), 2.76-2.97 (m, 4H), 2.50-2.70 (m, 2H), 2.36-2.48 (m, 2H), 2.24 (s, 7H), 2.02-2.15 (m, 2H), 1.82-2.00 (m, 4H), 1.63-1.80 (m, 5H) 1.44-1.62 (m, 5H), 1.41 (d, J=6.62 Hz, 3H), 1.28 (d, J=6.62 Hz, 3H), 1.22 (d, J=7.06 Hz, 3H). LCMS (ESI): m/z: [M+Na] calcd for $C_{52}H_{84}N_4O_{17}Na$: 1059.58; found 1059.5.

Example 70. Synthesis of Compound 5-QB

Compound 5-QB was synthesized in the manner similar to Compound 5-DT (Example 66), except 2-AG (Example 25) was substituted with 2-BF (Example 4) and (R)-2-((((9H-fluoren-9-yl)methoxy)carbonyl)amino)-3-(pyridin-3-yl)propanoic acid with fmoc-glycine. $^1$H NMR (400 MHz, Methanol-d4+Pyr-d5): δ ppm 6.19-6.78 (m, 13H), 5.72 (d, J=5.73 Hz, 1H), 5.01 (s, 1H), 4.83 (br. s., 1H), 4.71 (t, J=9.92 Hz, 1H), 4.47-4.62 (m, 2H), 4.24-4.44 (m, 3H), 4.03 (t, J=9.48 Hz, 1H), 3.81-3.97 (m, 3H), 3.75 (s, 1H), 3.68 (dd, J=8.60, 6.39 Hz, 1H), 3.53 (br. s., 1H), 3.40 (d, J=9.26 Hz, 1H), 2.76-3.02 (m, 4H), 2.50-2.69 (m, 2H), 2.33-2.47 (m, 2H), 2.25 (d, J=10.58 Hz, 1H), 2.05 (d, J=6.62 Hz, 2H), 1.80-1.99 (m, 4H), 1.62-1.79 (m, 5H), 1.51 (d, J=5.73 Hz, 5H), 1.40 (d, J=6.17 Hz, 3H), 1.28 (d, J=6.17 Hz, 3H), 1.21 (d, J=7.06 Hz, 3H). LCMS (ESI): m/z: [M+Na] calcd for $C_{50}H_{80}N_4O_{17}Na$: 1031.55; found 1031.6.

Example 71. Synthesis of Compound 5-QC

Compound 5-QC was synthesized in the manner similar to Compound 5-DT (Example 66), except 2-AG (Example 25) was substituted with 2-BF (Example 4) and (R)-2-((((9H-fluoren-9-yl)methoxy)carbonyl)amino)-3-(pyridin-3-yl)propanoic acid with (R)-2,5-bis((((9H-fluoren-9-yl)methoxy)carbonyl)amino)pentanoic acid. $^1$H NMR (400 MHz, Methanol-d4+Pyr-d5): δ ppm 6.12-6.69 (m, 13H), 5.61 (br. s., 1H), 5.44-5.52 (m, 2H), 4.87 (s, 1H), 4.71 (br. s., 1H), 4.60 (t, J=10.36 Hz, 1H), 4.30-4.48 (m, 2H), 4.09-4.25 (m, 2H), 3.93 (t, J=9.48 Hz, 1H), 3.64-3.85 (m, 3H), 3.50-3.61 (m, 1H), 3.46 (br. s., 1H), 3.31-3.37 (m, 1H), 3.13 (br. s., 2H), 2.84 (s, 3H), 2.42-2.68 (m, 2H), 2.26-2.38 (m, 2H), 1.72-2.15 (m, 10H), 1.50-1.70 (m, 5H), 1.44 (d, J=5.73 Hz, 4H), 1.34 (d, J=6.17 Hz, 3H), 1.23 (d, J=6.17 Hz, 3H), 1.15 (d, J=7.06 Hz, 3H). LCMS (ESI): m/z: [M+H] calcd for $C_{53}H_{88}N_5O_{17}$: 1066.61; found 1066.6.

Example 72. Synthesis of Compound 5-QD

Compound 5-QD was synthesized in the manner similar to Compound 5-DT (Example 66), except 2-AG (Example 25) was substituted with 2-BF (Example 4). $^1$H NMR (400 MHz, Methanol-d4+Py-d5): δ ppm 8.63-8.65 (m, 1H), 8.43-8.53 (m, 1H), 7.80 (d, J=7.94 Hz, 1H), 7.21-7.28 (m, 1H), 6.21-6.73 (m, 13H), 5.69 (d, J=5.29 Hz, 1H), 4.96 (s, 1H), 4.80 (br. s., 1H), 4.68 (t, J=10.36 Hz, 1H), 4.39-4.57 (m, 2H), 4.19-4.36 (m, 3H), 3.95-4.07 (m, 2H), 3.86-3.92 (m, 2H), 3.75-3.85 (m, 1H), 3.64 (dd, J=8.82, 6.17 Hz, 1H), 3.50 (br. s., 1H), 3.38 (d, J=9.70 Hz, 1H), 3.30 (dd, J=14.11, 4.85 Hz, 1H), 3.06 (dd, J=13.67, 7.50 Hz, 1H), 2.91 (s, 3H), 2.81 (d, J=11.47 Hz, 1H), 2.47-2.67 (m, 2H), 2.33-2.45 (m, 2H), 2.14-2.28 (m, 1H), 1.98-2.11 (m, 2H), 1.78-1.97 (m, 3H), 1.59-1.77 (m, 5H), 1.43-1.58 (m, 5H), 1.38 (d, J=6.17 Hz, 3H), 1.26 (d, J=6.62 Hz, 3H), 1.19 (d, J=7.06 Hz, 3H). LCMS (ESI): m/z: [M+Na] calcd for $C_{56}H_{85}N_5O_{17}Na$: 1122.59; found 1122.5.

Example 73. Synthesis of Compound 5-UA

Compound 5-UA was synthesized in the manner similar to Compound 5-DT (Example 66), except 2-AG (Example 25) was substituted with 2-J (Example 8), and (R)-2-((((9H-fluoren-9-yl)methoxy)carbonyl)amino)-3-(pyridin-3-yl)propanoic acid with NN-dimethylglycine. $^1$H NMR (400 MHz, Methanol-d4+Py-d5): δ ppm 6.28-6.62 (m, 14H), 5.47-5.45 (m, 1H), 5.36-5.41 (m, 1H), 4.87 (s, 1H), 4.70-4.75 (m, 1H), 4.58-4.64 (t, 1H), 4.41-4.50 (m, 2H), 4.25-4.35 (m, 1H), 4.20-4.25 (m, 1H), 4.14 (d, J=2.8 Hz, 1H), 3.80-3.95 (m, 3H), 3.66-3.86 (m, 4H), 3.30-3.46 (m, 1H), 3.36-3.41 (m, 1H), 3.20 (s, 2H), 2.36-2.64 (m, 17H), 1.52-2.12 (m, 13H), 1.33-1.35 (m, 4H), 1.34 (d, J=6.4 Hz, 3H), 1.23 (d, J=6.4 Hz, 3H), 1.25 (d, 3H) 1.15 (d, 3H). LCMS (ESI): m/z: [M+Na] calcd for $C_{56}H_{91}N_5O_{17}Na$: 1128.6; found 1128.5.

Example 74. Synthesis of Compound 5-UB

Compound 5-UB was synthesized in the manner similar to Compound 5-DT (Example 66), except 2-AG (Example 25) was substituted with 2-J (Example 8), and (R)-2-((((9H-fluoren-9-yl)methoxy)carbonyl)amino)-3-(pyridin-3-yl)propanoic acid with fmoc-glycine. ¹H NMR (400 MHz, Methanol-d4+Py-d5): δ 6.26-6.59 (m, 14H), 5.36-5.44 (m, 2H), 4.85 (s, 1H), 4.68-4.72 (m, 1H), 4.55-4.63 (t, 1H), 4.38-4.43 (m, 2H), 4.20-4.30 (m, 2H), 4.13-4.15 (m, 1H), 3.80-3.93 (m, 4H), 3.52-3.68 (m, 4H), 3.36-3.46 (m, 4H), 2.45-2.49 (m, 5H), 2.27-2.34 (m, 6H), 1.52-2.12 (m, 13H), 1.42-1.45 (m, 4H), 1.33 (d, J=6.0 Hz, 3H), 1.22 (d, J=6.0 Hz, 3H), 1.42 (d, J=7.2 Hz, 3H). LCMS (ESI): m/z: [M+Na] calcd for C₅₄H₈₇N₅O₁₇Na: 1100.61; found 1100.5.
Example 75. C3' Derivatives 6
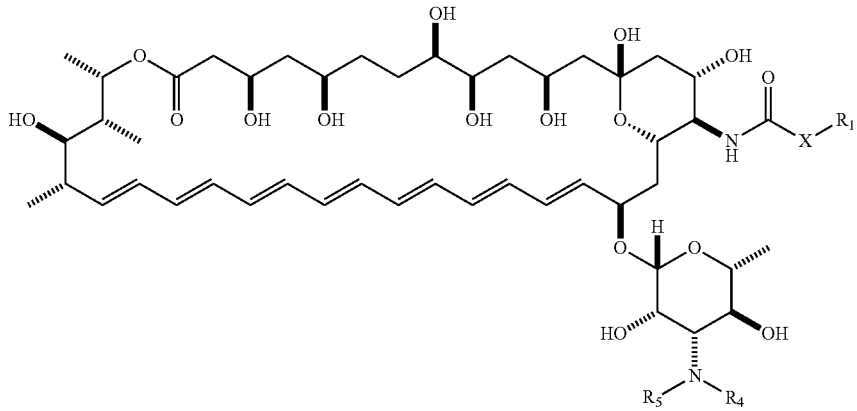
X = O or C or NR₂
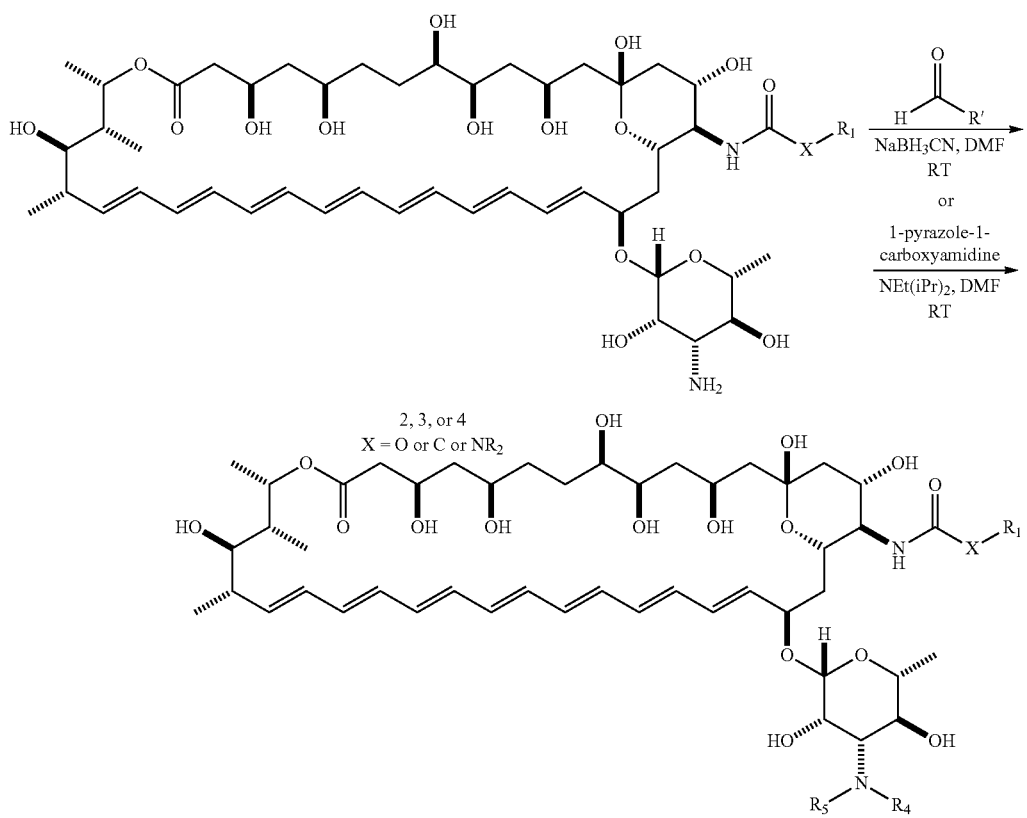
Scheme 6: Preparation of C3' Derivatives 6

C3' alkyl derivatives 6 are prepared according to the procedure defined by Paquet et al., *Chem Eur J* 14: 2465-81 (2008). Specifically, treatment of 2-BF (Example 4) with 1H-pyrazole-1-carboxamidine monohydrochloride (1 equiv.) and diisopropylethylamine (3 equiv.) in DMF at room temperature provides the guanidine compound 6-E. Analog 6-B is synthesized by treatment of 2-BF with N-(9-fluorenylmethoxycarbonyl)-3-aminopropanal (4 equiv.) and NaBH$_3$CN (4 equiv.) in DMF with catalytic HCl. Filtration and precipitation by addition to diethyl ether provides a yellow precipitate that can be purified by normal or reverse phase chromatography. Dissolution of this intermediate in DMF and treatment with piperidine (8 equiv.) at room temperature, followed by precipitation by addition to diethyl ether, provides 6-B.

Specific Compounds 6

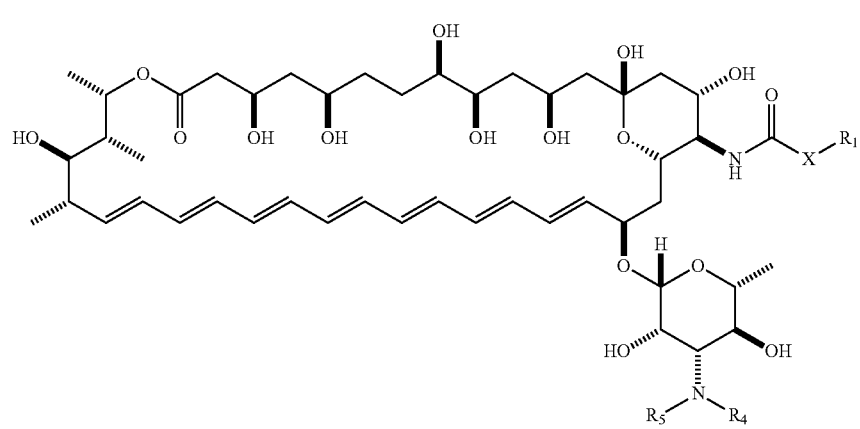

partial structures of which, defined according to the structure above, are depicted in Table 7 and Table 8:

TABLE 7

6 N R4, R5

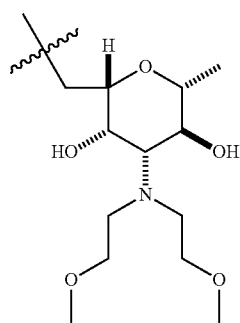 [SMILES: *C[C@@H]1O[C@H](C)[C@@H](O)[C@H](N(CCOC)CCOC)[C@@H]1O]
A

TABLE 7-continued

6 N R4, R5

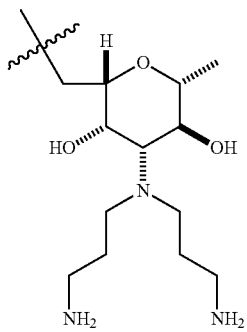 [SMILES: *C[C@@H]1O[C@H](C)[C@@H](O)[C@H](N(CCCN)CCCN)[C@@H]1O]
B

TABLE 7-continued

6 N R4, R5

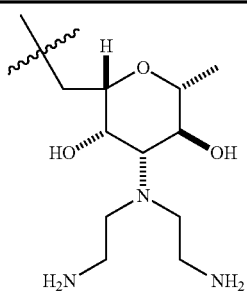
C

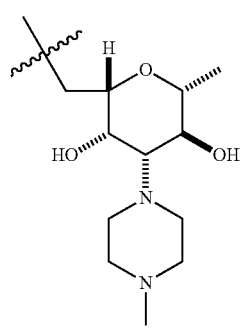 [SMILES: *C[C@@H]1O[C@H](C)[C@@H](O)[C@H](N2CCN(C)CC2)[C@@H]1O]
D

TABLE 7-continued

6 N R4, R5

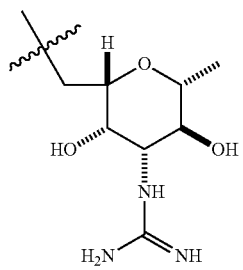 [SMILES: *C[C@@H]1O[C@H](C)[C@@H](O)[C@H](NC(=N)N)[C@@H]1O]   E

TABLE 8

6 XR 1

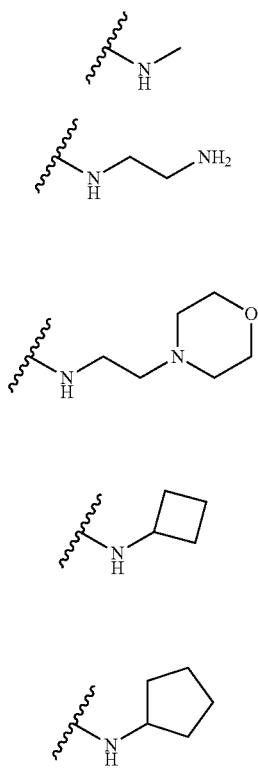

Q

R

S

T

U

Example 76. Synthesis of Compound 6-QB

Step 1: To a solution of (9H-fluoren-9-yl)methyl (3-oxo-propyl)carbamate (775.45 mg, 2.63 mmol, 5.00 equiv.) and 2-BF (Example 4) (500.00 mg, 525.14 umol, 1.00 equiv.) in DMF (15.00 mL) was added NaBH(OAc)$_3$ (1.11 g, 5.25 mmol, 10.00 equiv.) at r.t. for 1.5 hours. The mixture was poured into MTBE (200 mL) and filtered to give the solution of 3 g of crude (Fmoc)$_2$-6-QB which was used to next step directly.

Step 2: To the solution of compound (Fmoc)$_2$-6-QB (3 g, 1.99 mmol, 1.00 equiv.) in DMSO (about 20 mL) was added Et$_3$N (2.01 g, 19.90 mmol, 10.00 equiv.) and stirred at r.t. for 14 hrs. The reaction was poured into MTBE (200 mL) and precipitate was filtered to give yellow solid that was purified by prep-HPLC (FA) chromatography to yield 24.0 mg of 6-QB as yellow solid. $^1$H NMR (400 MHz, Methanol-d4+Pyr-d5): δ ppm 6.03-6.57 (m, 12H), 4.68 (s, 1H), 4.59 (br. s., 1H), 4.49 (t, J=9.70 Hz, 1H), 4.22-4.39 (m, 3H), 4.12 (d, J=9.70 Hz, 1H), 3.78-3.93 (m, 2H), 3.71 (d, J=10.58 Hz, 1H), 3.52 (t, J=6.39 Hz, 2H), 3.03-3.19 (m, 6H), 2.88-3.00 (m, 2H), 2.83 (d, J=11.47 Hz, 2H), 2.68 (s, 3H), 2.29-2.54 (m, 4H), 2.21 (d, J=16.32 Hz, 2H), 2.02 (d, J=5.73 Hz, 1H), 1.61-1.95 (m, 10H), 1.38-1.62 (m, 7H), 1.32 (d, J=5.73 Hz, 4H), 1.22 (d, J=6.17 Hz, 3H), 1.10 (d, J=6.17 Hz, 3H), 1.03 (d, J=7.06 Hz, 3H). LCMS (ESI): m/z: [M+H] calcd for C$_{55}$H$_{92}$N$_5$O$_{16}$: 1066.5; found 1066.5.

Example 77. Synthesis of Compound 6-TB

Compound 6-TB was synthesized in the manner similar to Compound 6-QB (Example 76), except 2-BF (Example 4) was substituted with 2-AG (Example 25). $^1$H NMR (400 MHz, Methanol-d4+Py-d5): δ ppm 6.09-6.57 (m, 13H), 5.52 (d, J=5.29 Hz, 1H), 4.45-4.74 (m, 4H), 4.20-4.42 (m, 4H), 4.13 (d, J=3.53 Hz, 2H), 3.79-3.96 (m, 3H), 3.74 (d, J=10.58 Hz, 1H), 3.56 (br. s., 1H), 3.39 (dd, J=8.38, 6.17 Hz, 1H), 3.24 (d, J=9.26 Hz, 2H), 3.03-3.20 (m, 6H), 2.90-3.02 (m, 2H), 2.86 (d, J=8.82 Hz, 1H), 2.28-2.54 (m, 4H), 1.62-2.28 (m, 20H), 1.26-1.62 (m, 14H), 1.23 (d, J=6.17 Hz, 3H), 1.12 (d, J=6.62 Hz, 3H), 1.04 (d, J=7.06 Hz, 3H). LCMS (ESI): m/z: [M+H] calcd for C$_{57}$H$_{96}$N$_5$O$_{16}$: 1106.3; found 1106.7.

Example 78. Synthesis of Compound 6-UB

Compound 6-UB was synthesized in the manner similar to Compound 6-QB (Example 76), except 2-BF (Example 4) was substituted with 2-CR (Example 51). $^1$H NMR (400 MHz, Methanol-d4+Pyr-d5): δ ppm 6.08-6.58 (m, 14H), 5.52 (d, J=5.27 Hz, 1H), 4.72 (s, 1H), 4.63 (br. s., 1H), 4.52 (t, J=10.48 Hz, 1H), 4.24-4.43 (m, 4H), 4.01-4.16 (m, 3H), 3.80-3.97 (m, 3H), 3.75 (d, J=10.54 Hz, 1H), 3.38-3.47 (m, 2H), 3.27 (d, J=8.16 Hz, 1H), 3.08-3.21 (m, 5H), 2.99 (dd, J=13.18, 6.27 Hz, 3H), 2.87 (d, J=10.79 Hz, 1H), 2.34-2.52 (m, 4H), 2.20-2.29 (m, 2H), 1.29-2.10 (m, 35H), 1.25 (d, J=6.40 Hz, 3H), 1.14 (d, J=6.27 Hz, 3H), 1.07 (d, J=7.15 Hz, 3H). LCMS (ESI): m/z: [M+H] calcd for C$_{58}$H$_{98}$N$_5$O$_{16}$: 1020.4; found 1020.7.

Example 79. Synthesis of Compound 6-SB

Compound 6-SB was synthesized in the manner similar to Compound 6-QB (Example 76), except 2-BF (Example 4) was substituted with 2-AF (Example 15). $^1$H NMR (400 MHz, Methanol-d4+Py-d5): δ ppm 8.69 (s, 2H), 6.01-6.61 (m, 10H), 5.44-5.57 (m, 1H), 5.39 (br. s., 3H), 4.71 (s, 1H), 4.51 (br. s., 2H), 4.18-4.41 (m, 3H), 3.84 (dd, J=14.77, 9.48 Hz, 3H), 3.58 (br. s., 5H), 3.35 (dd, J=14.77, 7.72 Hz, 3H), 3.24 (d, J=9.26 Hz, 2H), 3.06-3.20 (m, 5H), 2.82-3.03 (m, 3H), 2.28-2.52 (m, 10H), 1.80-2.07 (m, 8H), 1.39-1.76 (m, 9H), 1.33 (d, J=6.17 Hz, 3H), 1.22 (d, J=6.17 Hz, 3H), 1.11 (d, J=6.17 Hz, 3H), 1.04 (d, J=7.06 Hz, 3H). LCMS (ESI): m/z: [M+H] calcd for C$_{59}$H$_{101}$N$_6$O$_{16}$: 1165.71; found 1165.70.

Example 80. Synthesis of Compound 6-QE

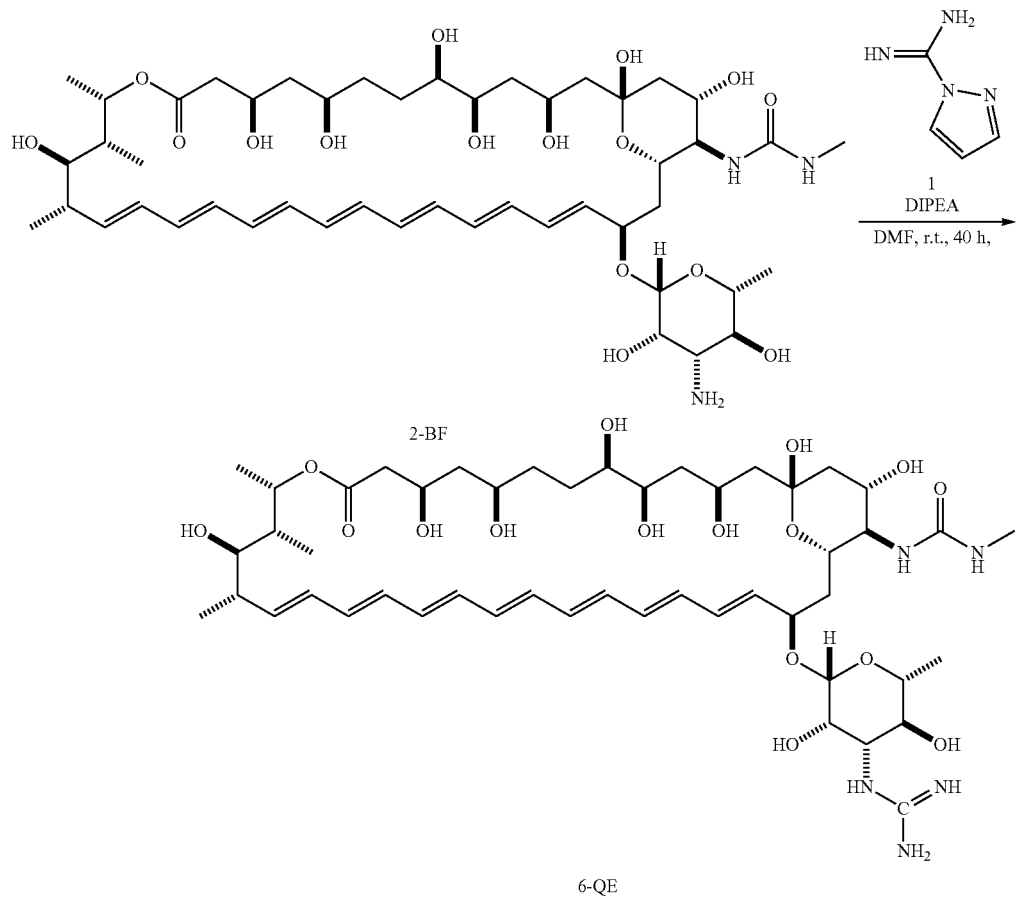

To a solution of compound 2-BF (Example 4) (380.00 mg, 399.11 umol, 1.00 equiv.) in DMF (4.00 mL) was added 1H-pyrazole-1-carboximidamide (109.87 mg, 997.78 umol, 2.50 equiv.) followed by DIPEA (412.65 mg, 3.19 mmol, 8.00 equiv.). The resulting mixture was stirred at RT for 40 hr., filtered to give the filtrate which was purified by prep-HPLC (FA) chromatography to yield 36.00 mg of AmBMU-A3 as yellow solid. $^1$H NMR (400 MHz, Methanol-d4+Py-d5): δ ppm 9.06 (s, 1H), 6.20-6.69 (m, 12H), 5.66 (d, J=5.73 Hz, 1H), 4.93 (s, 1H), 4.78 (br. s., 1H), 4.67 (t, J=9.92 Hz, 1H), 4.42-4.55 (m, 2H), 4.22-4.37 (m, 2H), 3.93-4.05 (m, 2H), 3.89 (d, J=11.03 Hz, 1H), 3.71-3.82 (m, 1H), 3.54-3.65 (m, 1H), 3.49 (br. s., 1H), 3.36-3.42 (m, 1H), 3.16 (s, 1H), 2.76-2.90 (m, 3H), 2.47-2.69 (m, 3H), 2.33-2.44 (m, 2H), 2.14-2.23 (m, 1H), 1.97-2.12 (m, 2H), 1.81-1.93 (m, 2H), 1.48-1.77 (m, 6H), 1.45 (d, J=5.73 Hz, 3H), 1.38 (d, J=6.62 Hz, 3H), 1.26 (d, J=6.17 Hz, 3H), 1.19 (d, J=7.06 Hz, 3H). LCMS (ESI): m/z: [M+H] calcd for $C_{49}H_{79}N_5O_{16}$: 994.15; found 994.5.

Example 81. C3'-azide 7

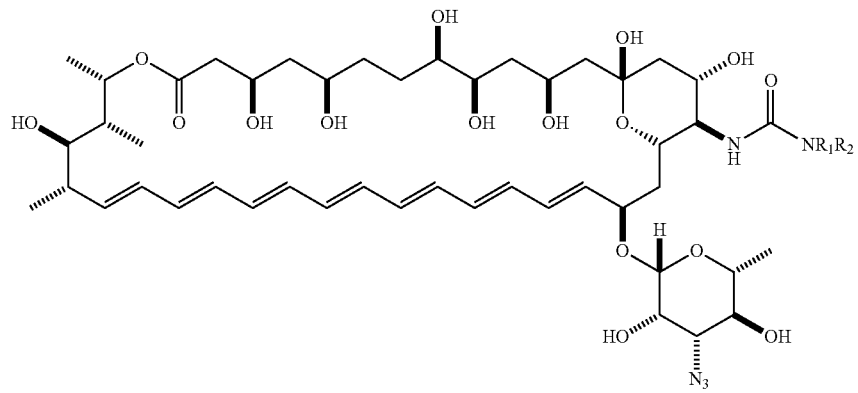

Scheme 7: Synthesis of 7

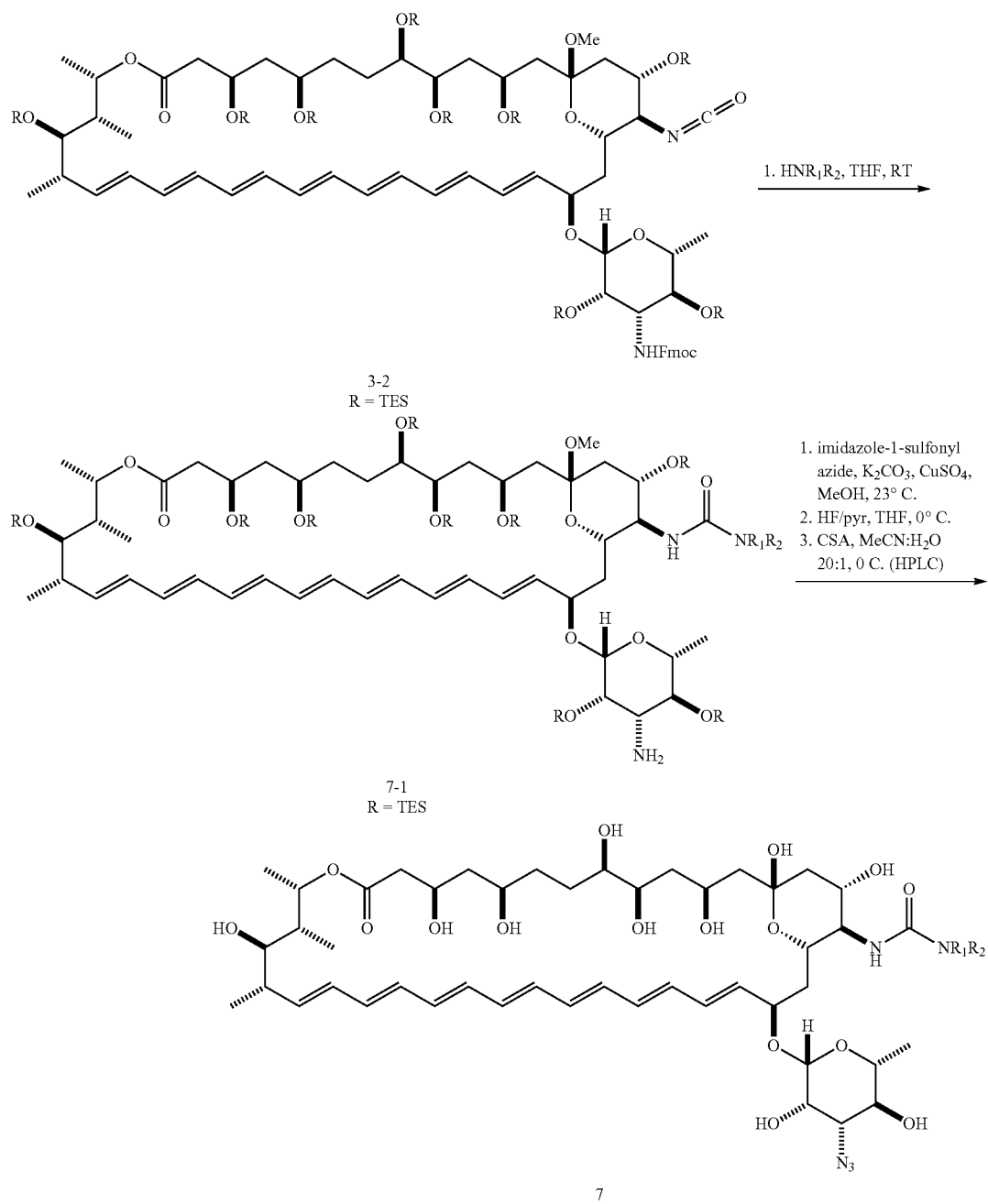

Compound 7 is prepared starting from intermediate 3-2. Treatment of this material with dimethylamine in THF (5 equiv.) at room temperature results in the addition of the amine to the isocyanate to form the urea at C16 and simultaneous removal of the Fmoc protecting group to provide intermediate 7-1 ($R_1$=$R_2$=$CH_3$). Treatment of this material with imidazole-1-sulfonylazide in the presence of potassium carbonate and copper sulfate in methanol generates the corresponding 3'-azide. Desilylation of this material with HF/pyridine, followed by purification by HPLC under aqueous acidic conditions produces the desired compound 7.

Specific Compounds 7
7 NR1; $R^2$=H

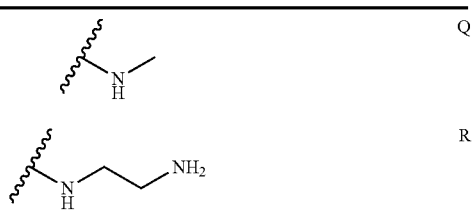

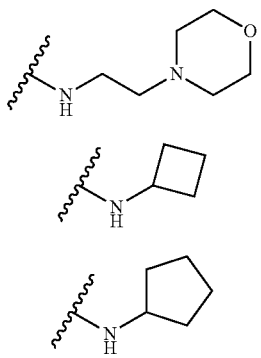

Alternatively, compounds 7 can be prepared in the following manner.

Example 82. Synthesis of Compound 7-Q ture was filtered, and the filtrate was concentrated under reduced pressure. Purification by prep-HPLC(FA) chromatography afforded 14 mg of 7-Q as a yellow solid. $^1$H NMR (400 MHz, Methanol-d4+Py-d5): δ ppm 6.09-6.57 (m, 14H), 5.49 (d, J=6.62 Hz, 2H), 4.71 (s, 1H), 4.44-4.64 (m, 3H), 4.22-4.39 (m, 2H), 4.01-4.18 (m, 3H), 3.51-3.91 (m, 6H), 3.34-3.45 (m, 3H), 2.67 (s, 3H), 2.30-2.58 (m, 4H), 2.14-2.28 (m, 2H), 1.94-2.09 (m, 2H), 1.25-1.93 (m, 18H), 1.21 (d, J=6.17 Hz, 3H), 1.10 (d, J=6.17 Hz, 4H), 0.99-1.05 (m, 3H). LCMS (ESI): m/z: [M+Na] calcd for $C_{48}H_{75}N_5O_{16}Na$: 1000.5; found 1000.5.

Example 83. Synthesis of Compound 7-S

Compound 7-S was synthesized in the manner similar to Compound 7-Q (Example 82), except 2-BF (Example 4) was substituted with 2-AF (Example 15). $^1$H NMR (400 MHz, Methanol-d4+Py-d5): δ ppm 6.37-6.54 (m, 4H), 6.24-6.37 (m, 5H), 6.10-6.24 (m, 4H), 5.49 (s, 1H), 5.31-5.40 (m,

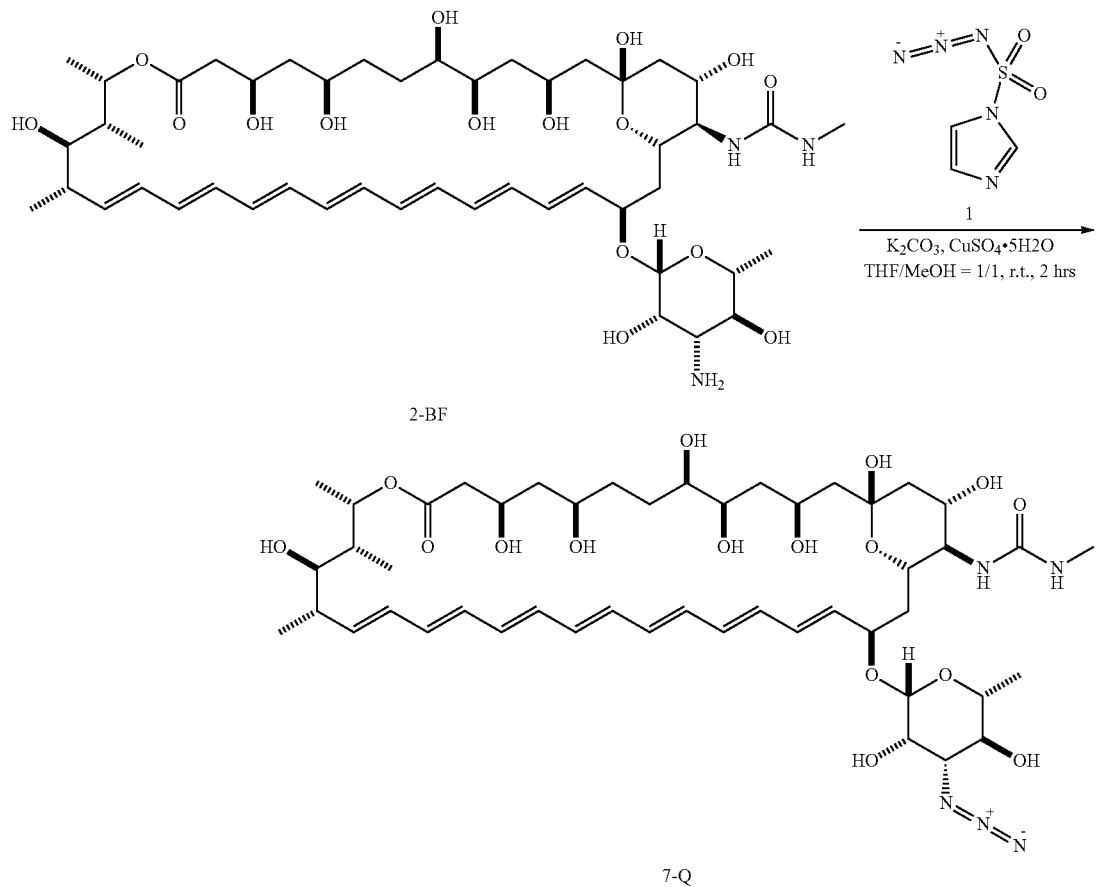

A round bottom flask was charged with 2-BF (Example 4) (500 mg, 525.14 mmol) which was dissolved in THF (3 mL) and MeOH (3 mL) at 20° C. K$_2$CO$_3$ (290.32 mg, 2.10 mmol, 4 equiv.), CuSO$_4$.5H$_2$O (5.24 mg, 21.01 umol, 0.04 equiv.) and 1H-imidazole-1-sulfonyl azide (264.18 mg, 1.26 mmol, 2.4 eq, HCl) were subsequently added and the reaction was stirred for 2 hours at RT. The reaction mixture was pour into 2-methoxy-2-methylpropane (200 mL). The resulting mix- 2H), 4.71 (s, 1H), 4.60 (m, 1H), 4.50 (m, 2H), 4.20-4.35 (m, 3H) 4.13 (d, J=3.09 Hz, 2H), 4.04 (m, 2H), 3.77-3.85 (m, 2H), 3.70 (d, J=11.03 Hz, 1H), 3.55 (m, 5H), 3.41 (m, 3H), 3.22 (m, 1H), 2.51 (m, 1H), 2.32 (m, 3H), 1.98 (s, 1H), 1.62-1.88 (m, 7H), 1.54 (m, 4H), 1.42 (m, 3H), 1.32 (d, J=6.17 Hz, 3H), 1.21 (d, J=6.17 Hz, 3H), 1.10 (d, J=6.62 Hz, 3H), 1.02 (d, J=7.06 Hz, 3H). LCMS (ESI): m/z: [M+H] calcd for $C_{53}H_{84}N_6O_{17}$: 1077.59; found 1077.6.

Example 84. Synthesis of Compound 7-T

Compound 7-T was synthesized in the manner similar to Compound 7-Q (Example 82), except 2-BF (Example 4) was substituted with 2-AG (Example 25). $^1$H NMR (400 MHz, Methanol-d4+Pyr-d5): δ ppm 6.16-6.49 (m, 13H), 5.53 (s, 1H), 4.74 (s., 1H), 4.26-4.60 (m., 5H), 4.17 (s., 1H), 3.87-3.90 (m, 4H), 3.21-3.44 (m, 6H), 2.20-2.33 (m, 9H), 1.32-1.86 (m, 15H), 1.33 (d, J=8 Hz, 3H), 1.22 (d, J=8 Hz, 3H), 1.10 (d, J=8 Hz, 3H), 1.30 (d, J=8 Hz, 3H). LCMS (ESI): m/z: [M+Na] calcd for $C_{51}H_{79}N_5O_{16}Na$: 1040.19; found 1040.4.

Example 85. C2'-epi-Urea 8

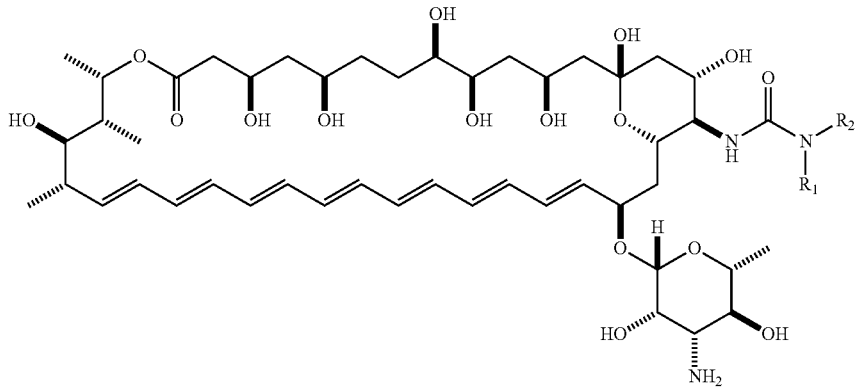

8

Synthesis of 8:

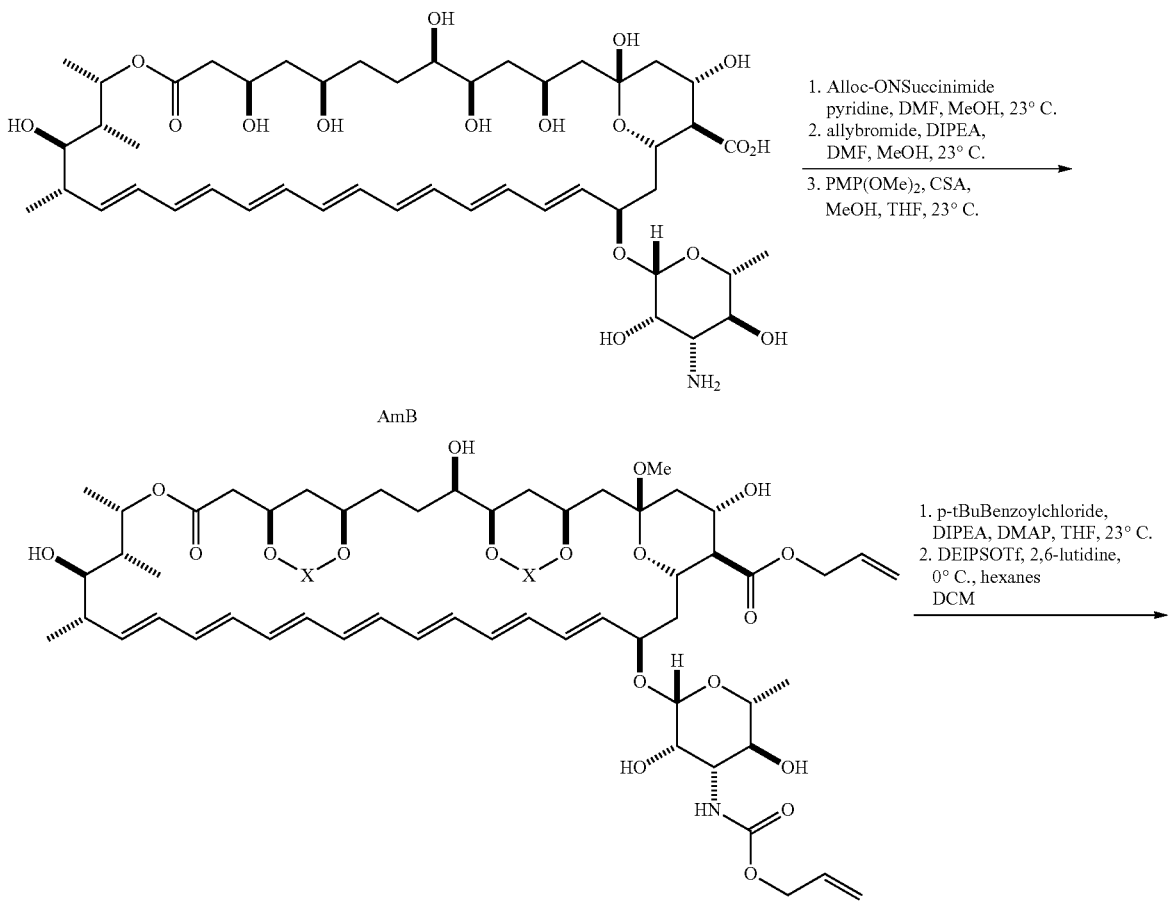

AmB

1. Alloc-ONSuccinimide pyridine, DMF, MeOH, 23° C.
2. allylbromide, DIPEA, DMF, MeOH, 23° C.
3. PMP(OMe)$_2$, CSA, MeOH, THF, 23° C.

1. p-tBuBenzoylchloride, DIPEA, DMAP, THF, 23° C.
2. DEIPSOTf, 2,6-lutidine, 0° C., hexanes DCM

X = CH$_2$PMP
8-1

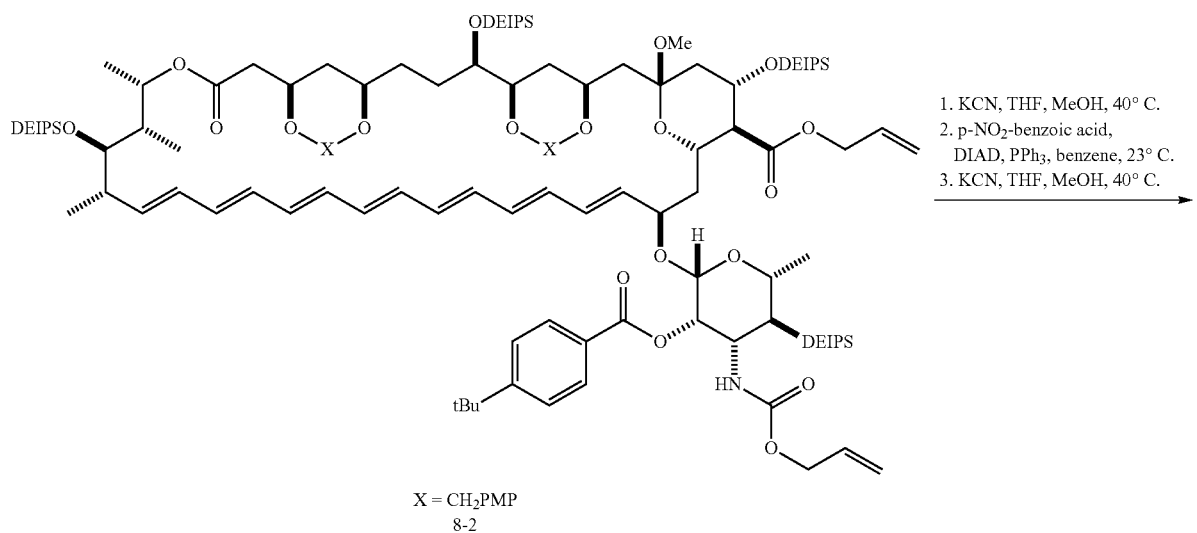
8-2, X = CH₂PMP
1. KCN, THF, MeOH, 40° C.
2. p-NO₂-benzoic acid, DIAD, PPh₃, benzene, 23° C.
3. KCN, THF, MeOH, 40° C.
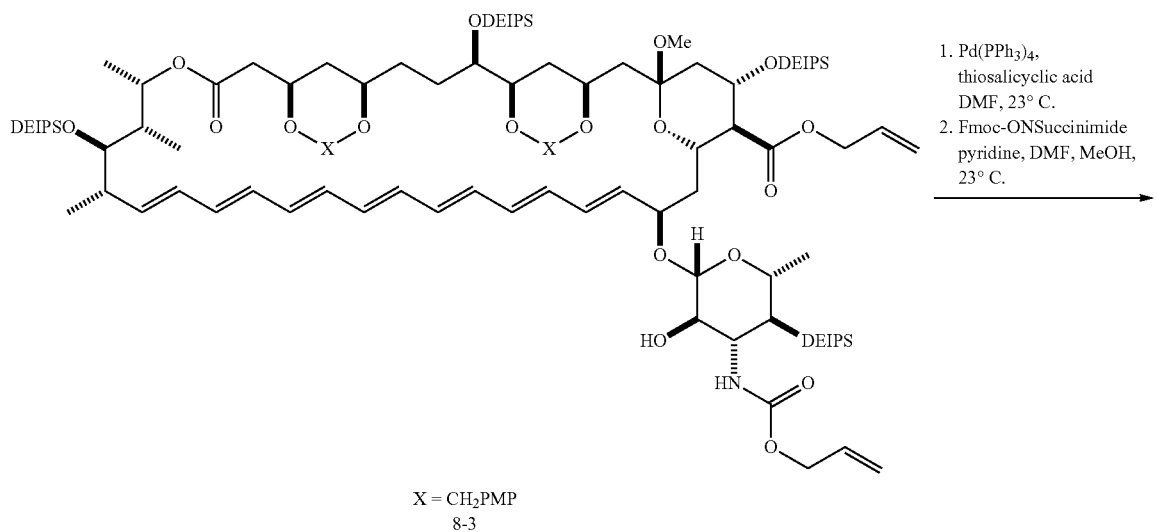
8-3, X = CH₂PMP
1. Pd(PPh₃)₄, thiosalicyclic acid DMF, 23° C.
2. Fmoc-ONSuccinimide pyridine, DMF, MeOH, 23° C.
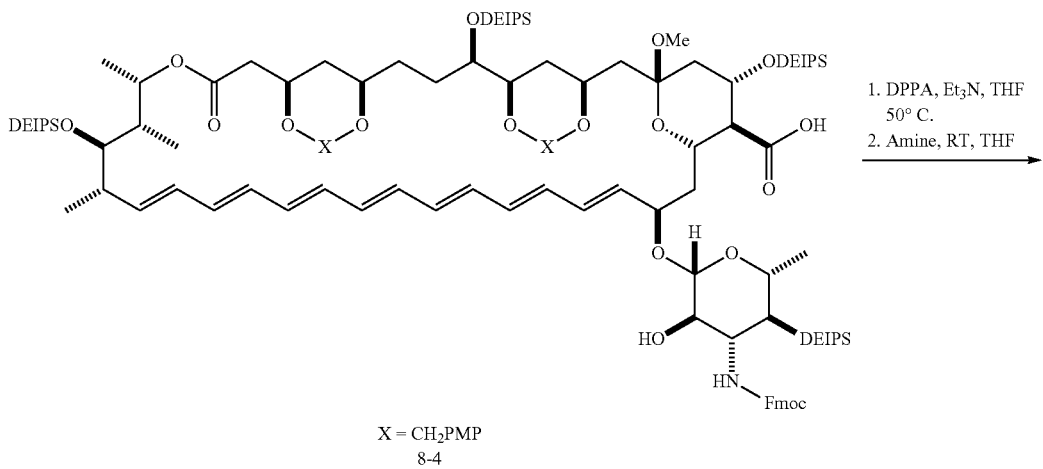
8-4, X = CH₂PMP
1. DPPA, Et₃N, THF 50° C.
2. Amine, RT, THF -continued
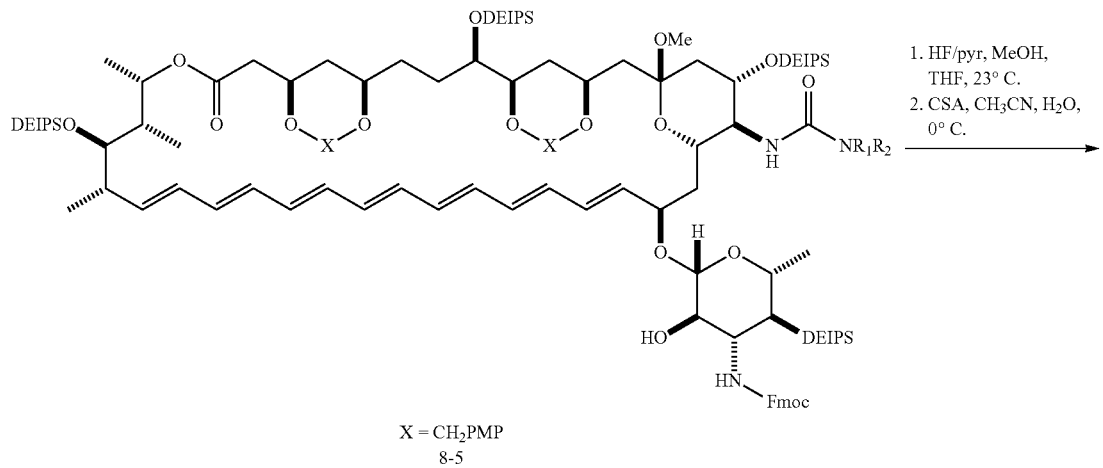
X = CH₂PMP
8-5
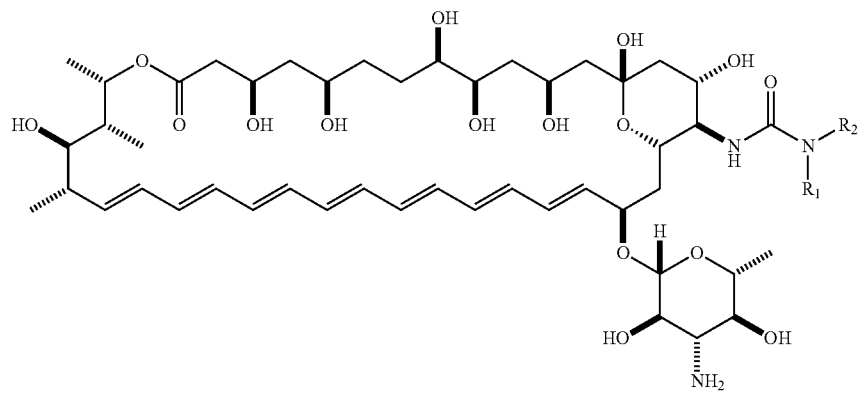
8
Synthesis of 8-1:
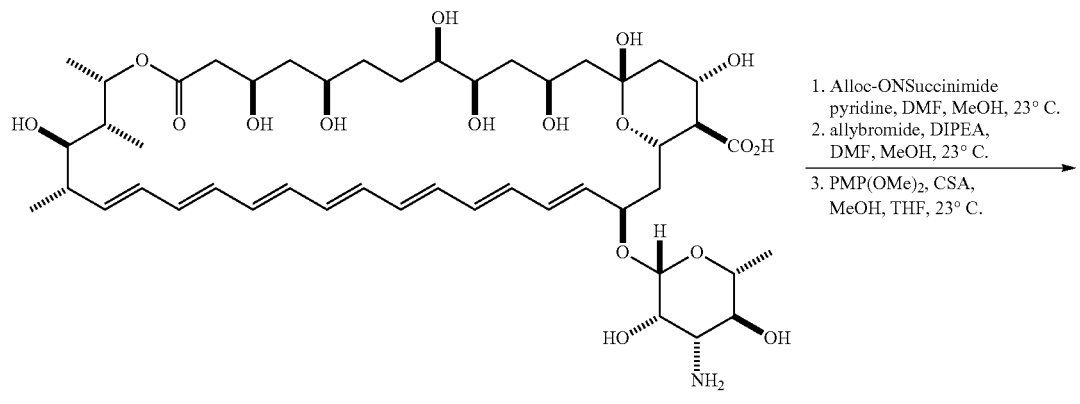
AmB -continued

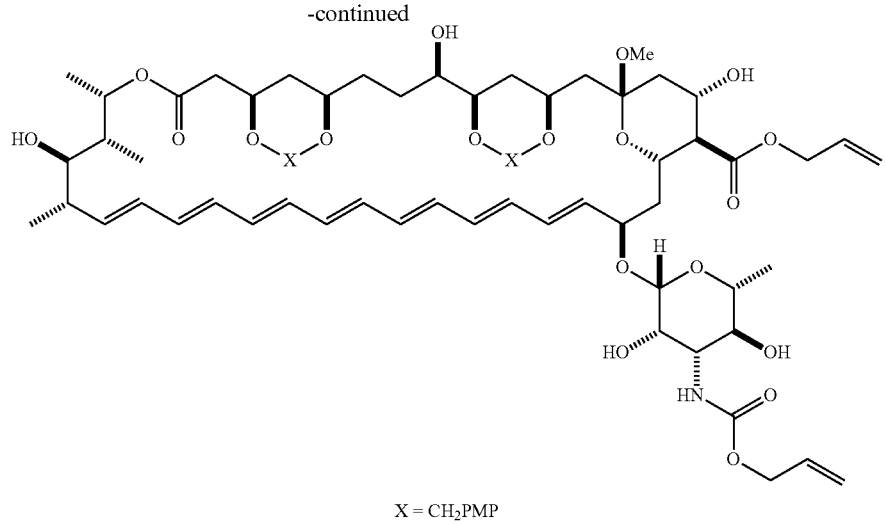

X = CH₂PMP
8-1

To a stirred suspension of AmB (4.0 g, 4.3 mmol, 1.0 equiv.) in DMF:MeOH (75 mL: 75 mL) in a 300 mL round bottom flask at 23° C. was added pyridine (5.0 mL, 50.0 mmol, 11.5 equiv.) and alloc-succinimide (2.4 g, 12.05 mmol, 2.8 equiv.). After stirring for 16 h at 23° C., the dark orange, homogeneous solution was slowly poured into rapidly stirring Et₂O (3.5 L). The yellow suspension was filtered through Whatman 42 filter paper (110 mm diameter) and washed with Et₂O (3×100 mL) before the cake was allowed to fully dry. The fully dried alloc-AmB yellow powder (4.3 mmol, quantitative) was taken on to the subsequent reaction without further purification.

To a stirred suspension of alloc-AmB (4.0 g, 4.3 mmol, 1.0 equiv.) in DMF:MeOH (10:1) in a 300 mL round bottom flask at 23° C. was added sequentially Hunig's base (3.75 mL, 21.5 mmol, 5.0 equiv.) and allyl bromide (11.2 mL, 129.0 mmol, 30 equiv.). After stirring for 8 h at 23° C., the dark orange, homogeneous solution was slowly poured into rapidly stirring Et₂O:Hex (1:1, 3.5 L). The subsequent yellow suspension was filtered through Whatman 42 filter paper (110 mm diameter) and washed with Et₂O (3×100 mL) before the cake was allowed to fully dry. The fully dried alloc-allylester-AmB (4.3 mmol, quantitative) was taken on to the subsequent reaction as a yellow powder without further purification.

To a stirred suspension of alloc-allylester-AmB (4.3 mmol, 1.0 equiv.) in MeOH (35 mL, 0.1 M) in a 300 mL round bottom flask at 23° C. was added anisaldehyde dimethylacetal (4.0 mL, 23.5 mmol, 5.5 equiv.) and stirred for 10 min until a very fine, uniform suspension formed. CSA (250 mg, 1.08 mmol, 0.25 equiv.) as a white crystalline solid was then added in one portion. After stirring at 23° C. for 30 min, Et₃N was added (~160 µL) followed by THF (81 mL to dilute down to 0.03M). The reaction was slowly poured into rapidly stirring hexane (3.5 L). The subsequent yellow suspension was filtered through Whatman 42 filter paper (110 mm diameter) and washed with Et₂O (3×100 mL) before the cake was allowed to fully dry. The product was purified via flash chromatography (SiO₂, gradient elution 50:49:1 EtOAc:Hex:MeOH to 75:24:1 EtOAc:Hex:MeOH) to afford 8-1 (1.56 g, 1.204 mmol, 28%) as an orange solid. Rf=0.21 (50:49:1) EtOAc:Hex:MeOH) Calculated for $C_{71}H_{95}NO_{21}$ (M+Na)+: 1320.6294, Found: 1320.6285.

Synthesis of 8-2:

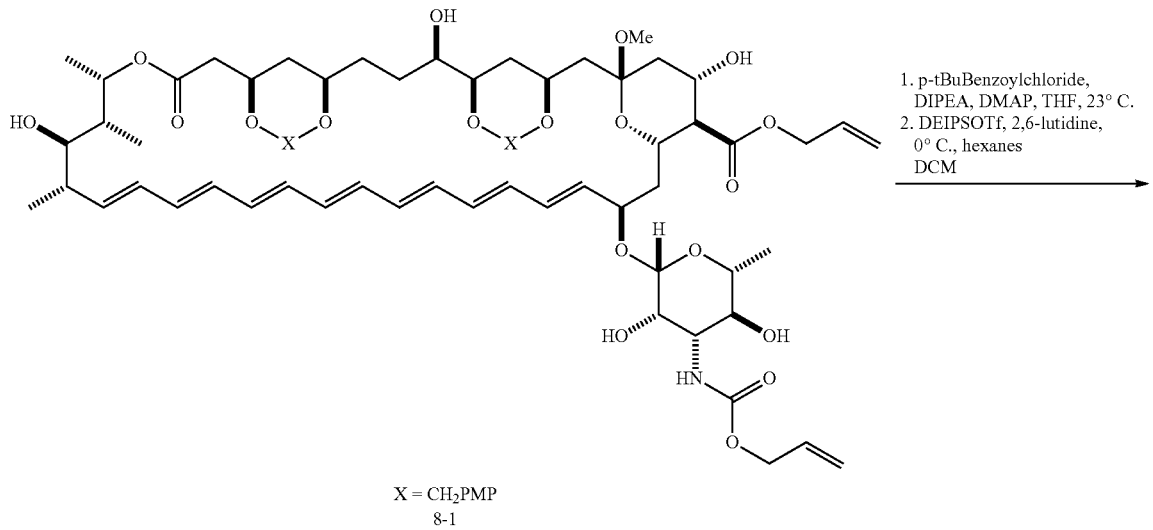

X = CH₂PMP
8-1

-continued

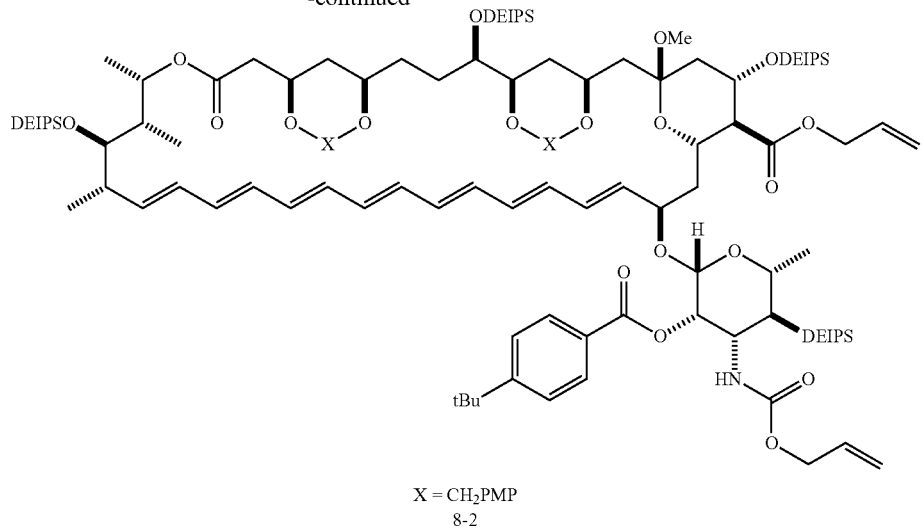

X = CH$_2$PMP
8-2

Intermediate 8-1 (4.06 g, 3.127 mmol, 1.0 equiv.) was azeotropically dried with benzene (3×10 mL) and placed on high vacuum overnight in a 500 mL round bottom flask. To intermediate 8-1 was added THF (105 mL) followed by DIPEA (0.87 mL, 5.0 mmol, 1.6 equiv.). In a separate 200 mL round bottom flask was added sequentially THF (64 mL), DMAP (611.2 mg, 5.0 mmol, 1.6 equiv.), and dropwise p-tertbutylbenzoylchloride (855 µL, 4.38 mmol, 1.4 equiv.) forming a fine, white suspension. Most of this suspension was slowly added dropwise via cannula to the THF, DIPEA and 8-1 solution over ~50 min until a majority of the starting material was converted as judged by TLC. The reaction was diluted with EtOAc and transferred to a separatory funnel containing aqueous saturated sodium bicarbonate and extracted with EtOAc. The combined organic phases were dried over sodium sulfate, filtered and concentrated under reduced pressure. Purification by flash chromatography (SiO$_2$, gradient eluent 65:33:2 EtOAc:Hex:MeOH isocratic) afforded the desired acylated intermediate (2.28 g, 1.56 mmol, 50% yield) as an orange solid. Rf=0.24 (65:33:2 EtOAc:Hex:MeOH, HRMS (ESI) Calculated for C$_{82}$H$_{107}$NO$_{22}$ (M+Na)+: 1480.7182, Found: 1480.7172. This acylated intermediate (4.15 g, 2.846 mmol, 1.0 equiv.) was azeotropically dried with benzene (3×10 mL) and placed on high vacuum overnight in a 300 mL round bottom flask. DCM (48 mL) and hexanes (48 mL) were added followed by freshly distilled 2,6-lutidine (2.98 mL, 25.58 mmol, 9.1 equiv.) and cooled to 0° C. Diethylisopropylsilyl triflate (DEIPSOTf; 3.39 mL, 17.05 mmol, 6.0 equiv.) was added dropwise over 10 min and stirred for another hour at 0° C. The reaction was diluted with Et$_2$O (200 mL), transferred to a separatory funnel containing Et$_2$O and aqueous saturated bicarbonate, and extracted with Et$_2$O. The combined organic phases were dried over sodium sulfate, filtered, and concentrated under reduced pressure. Purification by flash chromatography (SiO$_2$, gradient eluent 1:9 EtOAc:Hex to 1:4 EtOAx:Hex) afforded 8-2 (4.46 g, 2.28 mmol, 80% yield) as an orange solid. Rf=0.21 (1:4 EtOAc:Hex) HRMS (ESI) Calculated for C$_{110}$H$_{171}$NO$_{22}$ (M+Na)+: 1993.1268, Found: 1993.1189.

Synthesis of 8-3:

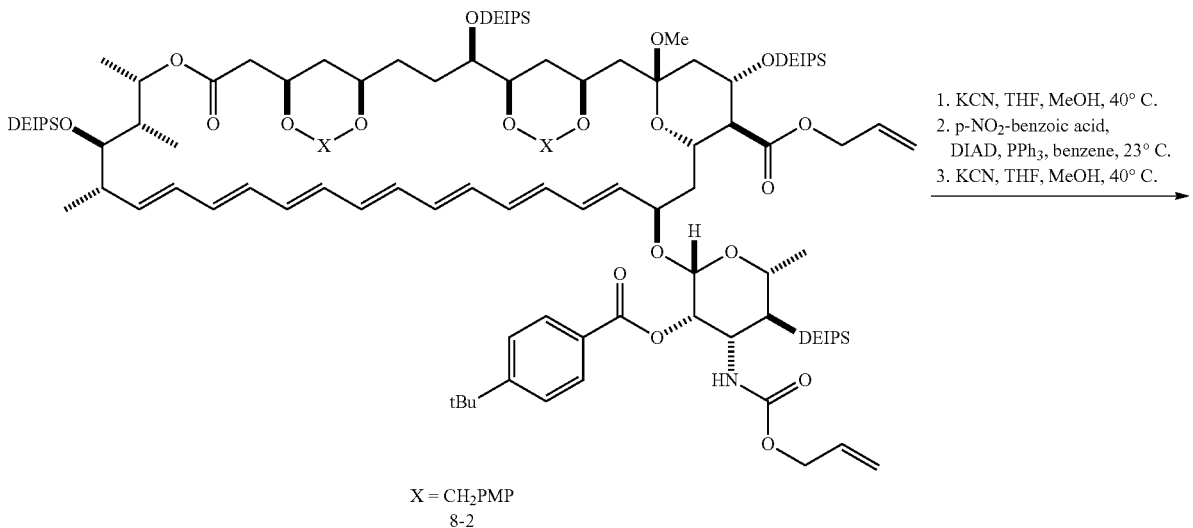

1. KCN, THF, MeOH, 40° C.
2. p-NO$_2$-benzoic acid, DIAD, PPh$_3$, benzene, 23° C.
3. KCN, THF, MeOH, 40° C.

X = CH$_2$PMP
8-2

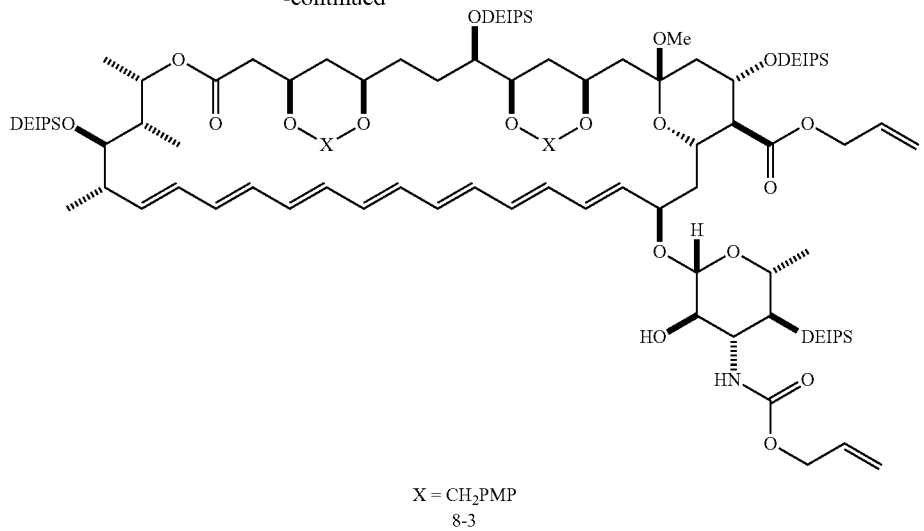

X = CH₂PMP
8-3

Intermediate 8-2 (6.39 g, 3.24 mmol, 1.0 equiv.) was azeotropically dried with benzene (3×10 mL) and placed on high vacuum overnight in a 300 mL round bottom flask. Intermediate 8-2 was added to a mixture of THF (71 mL) and MeOH (140 mL). KCN (314.8 mg, 4.83 mmol, 1.5 equiv.) was added, and the material was placed under Ar atmosphere, sealed and warmed to 40° C. and stirred for 48 h behind a blast shield. The reaction transferred to a separatory funnel containing Et₂O and aqueous saturated bicarbonate. The organic phase was washed with water followed by brine. The combined aqueous phases were extracted with Et₂O. The combined organic phases were dried over sodium sulfate, filtered and concentrated under reduced pressure. Purification by flash chromatography (SiO₂, gradient eluent 1:9 EtOAc:Hex to 1:4 EtOAx:Hex) afforded the deprotected alcohol (2.93 g, 1.62 mmol, 50% yield) as an orange solid. Rf=0.22 (3:7 EtOAc:Hex). HRMS (ESI) Calculated for $C_{99}H_{159}NO_{21}$ (M+Na)+: 1833.0379, Found: 1833.0355. The deprotected alcohol (2.93 g, 1.62 mmol, 1.0 equiv.) was azeotropically dried with benzene (3×10 mL) and placed on high vacuum overnight in a 250 mL round bottom flask. p-Nitrobenzoic acid (1.62 g, 9.7 mmol, 6.0 equiv.), PPh₃ (2.54 mg, 9.7 mmol, 6.0 equiv.) and benzene (54 mL) were added. The solution was cooled to 0° C. and DIAD (1.91 mL, 9.7 mmol, 6.0 equiv.) was added drop-wise and the reaction was stirred at 0° C. for 1 h. The reaction was then stirred at 23° C. for 3 h. The reaction was transferred to a separatory funnel containing Et₂O and aqueous saturated sodium bicarbonate. The organic phase was washed with water followed by brine. The combined aqueous phases were extracted with Et₂O. The combined organic phases were dried over sodium sulfate, filtered and concentrated under reduced pressure. Purification by flash chromatography (SiO₂, gradient eluent 1:9 EtOAc:Hex to 1:4 EtOAx:Hex) afforded the C2'epi nitrobenzoate (2.66 g, 1.36 mmol, 84% yield) as an orange solid. Rf=0.2 (1:4 EtOAc:Hex) HRMS (ESI) Calculated for $C_{106}H_{162}N_2O_{24}Si_4$ (M+Na)+: 1982.0492, Found: 1982.0464.

The C2'epi nitrobenzoate (2.46 g, 1.25 mmol, 1.0 equiv.) was azeotropically dried with benzene (3×10 mL) and placed on high vacuum overnight in a 250 mL iChem. Flask THF (27.3 mL) and MeOH (54.6 mL) were added followed by KCN (121.8 mg, 1.87 μmol, 1.5 equiv.). The reaction was placed under Ar atmosphere, sealed and warmed to 40° C. and stirred for 48 h behind a blast shield. The reaction transferred to a separatory funnel containing Et₂O and aqueous saturated bicarbonate. The organic phase was washed with water followed by brine. The combined aqueous phases were extracted with Et₂O. The combined organic phases were dried over sodium sulfate, filtered and concentrated under reduced pressure. Purification by flash chromatography (SiO₂, gradient eluent 1:9 EtOAc:Hex to 1:4 EtOAx:Hex) afforded 8-3 (1.72 g, 0.948 mmol, 76% yield) as an orange solid. Rf=0.2 (3:7 EtOAc:Hex. HRMS (ESI): Calculated for $C_{99}H_{159}NO_{21}Si_4$ (M+Na)+: 1833.0379, Found: 1833.03.

Synthesis of 8:

Intermediate 8-3 is converted to the desired target 8 using standard modifications described in Scheme 8. Specifically, simultaneous cleavage of the allyl ester and alloc groups proceeds smoothly using palladium catalysis and thiosalicylic acid. Reprotection of the mycosamine nitrogen and conversion of the carboxylate group to a urea provides intermediate 8-5, which is desilylated and ketalized using standard conditions to produce 8.

Example 86. In Vitro Assessment of Biological Activity

A high therapeutic index is preferable for a drug to have a favorable safety profile. Classically, in an established clinical indication setting of an approved drug, therapeutic index refers to the ratio of the dose of drug that causes adverse effects at an incidence/severity not compatible with the targeted indication (e.g. toxic dose in 50% of subjects, $TD_{50}$) divided by the dose that leads to the desired pharmacological effect (e.g. efficacious dose in 50% of subjects, $ED_{50}$). In a drug development setting, therapeutic index is, more generally, the quantitative relationship between efficacy (pharmacology) and safety (toxicology).

Each derivative described herein is tested in vitro for biological activity against both yeast and human cells to determine its therapeutic index. A broth microdilution experiment determines the MIC (minimum inhibitory concentration) of each derivative against *S. cerevisiae* and the clinically relevant *C. albicans*, thereby establishing the antifungal activity of each novel derivative. To test for toxicity against human cells, each compound is tested in a hemolysis assay against red blood cells which determines the concentration of compound required to cause 90% lysis of human red blood cells ($EH_{90}$). Additionally, each compound is exposed to human primary renal tubule cells to determine the toxicity of each compound against kidney cells. These assays, when compared against the known or measured values of AmB against the same cells, demonstrate the improvement in therapeutic index of each compound as compared to AmB.

Example 87. In Vivo Assessment of Biological Activity

The antifungal efficacies of compounds are tested in vivo in a mouse model of disseminated candidiasis. In this experiment neutropenic mice are infected with *C. albicans* via the tail vein, and then 2 hours post infection the mice are treated with a single intraperitoneal injection of AmB or test agent. Then 2, 6, 12, and 24 hours post infection the mice are sacrificed, and the fungal burden present in their kidneys is quantified.

INCORPORATION BY REFERENCE

All patents and published patent applications mentioned in the description above are incorporated by reference herein in their entirety.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

We claim:

1. A compound represented by Formula (IVa) or a pharmaceutically acceptable salt thereof:

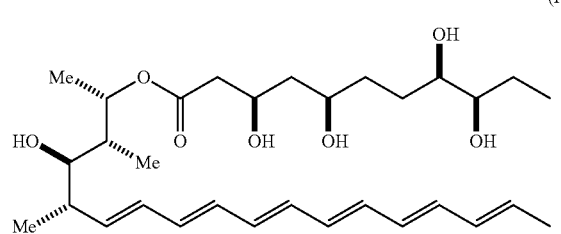

(IVa)

-continued

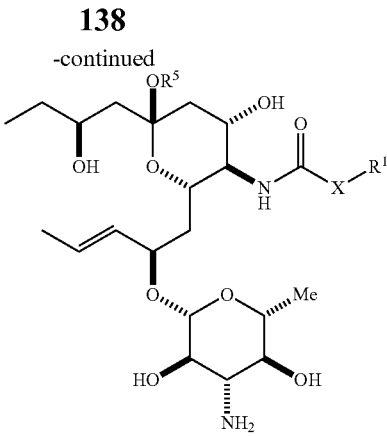

wherein, independently for each occurrence:
  $R^5$ is selected from the group consisting of hydrogen, alkyl, and haloalkyl; and
  (a) —$XR^1$ is selected from the group consisting of

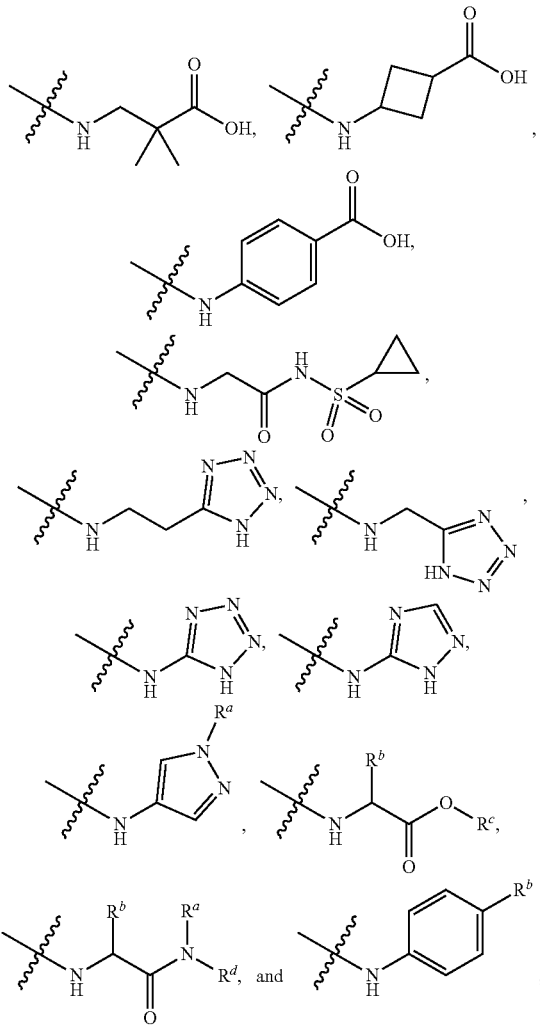

wherein, independently for each occurrence:
  $R^a$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;

$R^b$ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl;

$R^c$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, and aminoalkyl; and $R^d$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or, when —XR¹ is

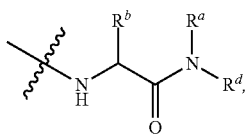

$R^a$ and $R^d$, together with the nitrogen to which they are attached, may form a substituted or unsubstituted 3- to 10-membered heterocyclic ring, wherein said ring is monocyclic, bicyclic, tricyclic, or spirocyclic;

(b) —XR¹ is selected from the group consisting of

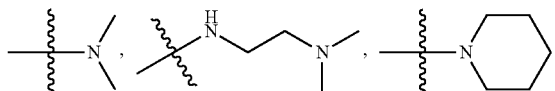

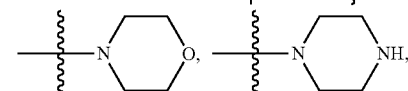

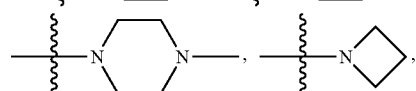

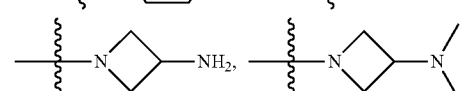

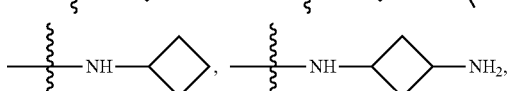

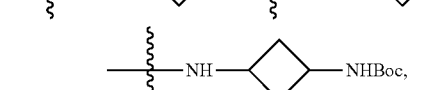

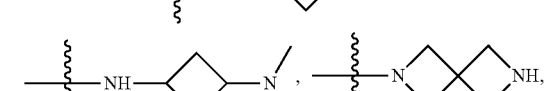

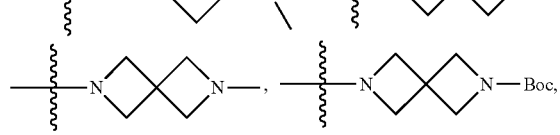

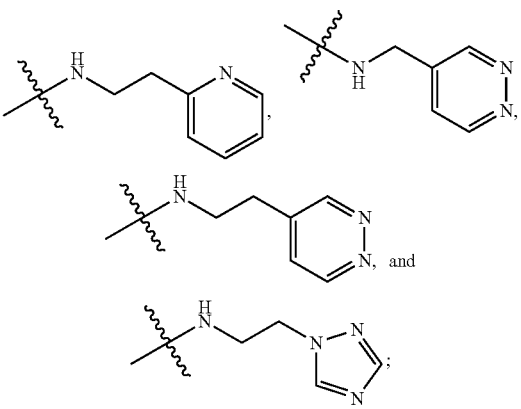

(c) —XR¹ is selected from the group consisting of

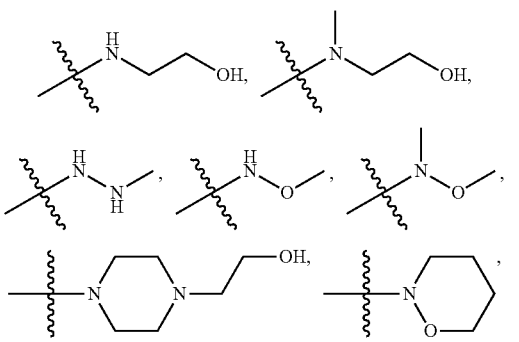

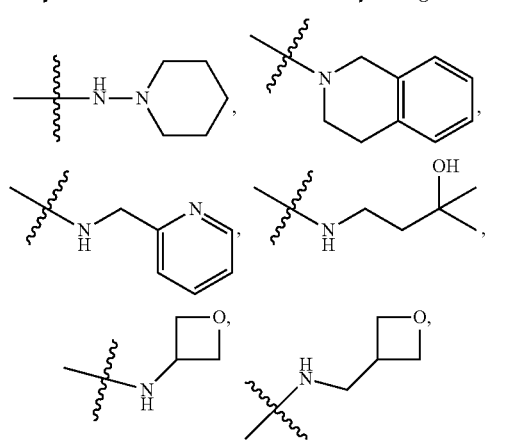

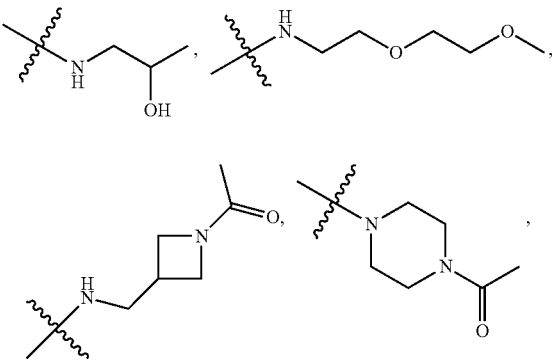

141
-continued
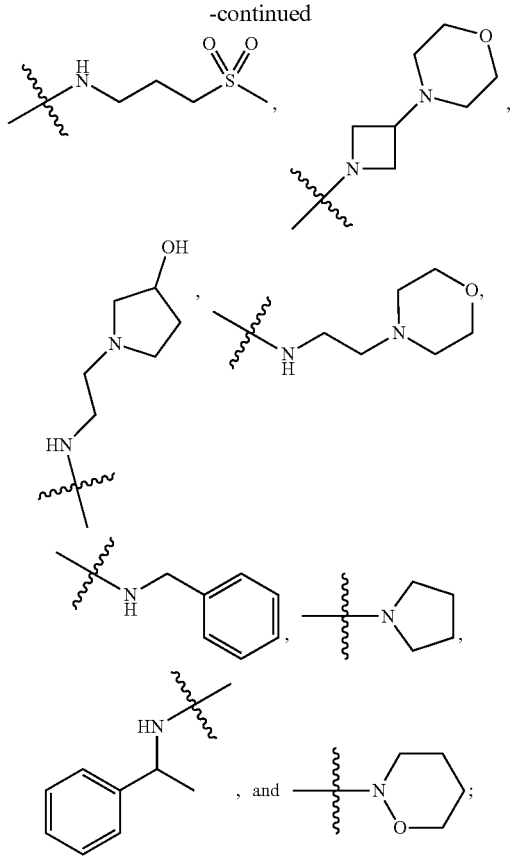
or
(d) —XR$^1$ is selected from the group consisting of
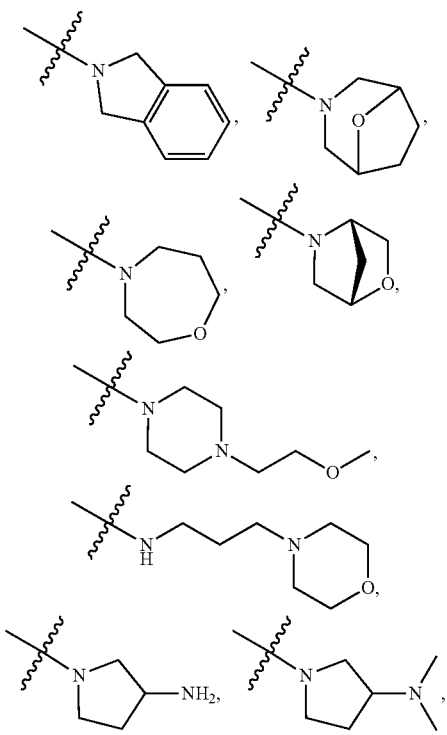
142
-continued
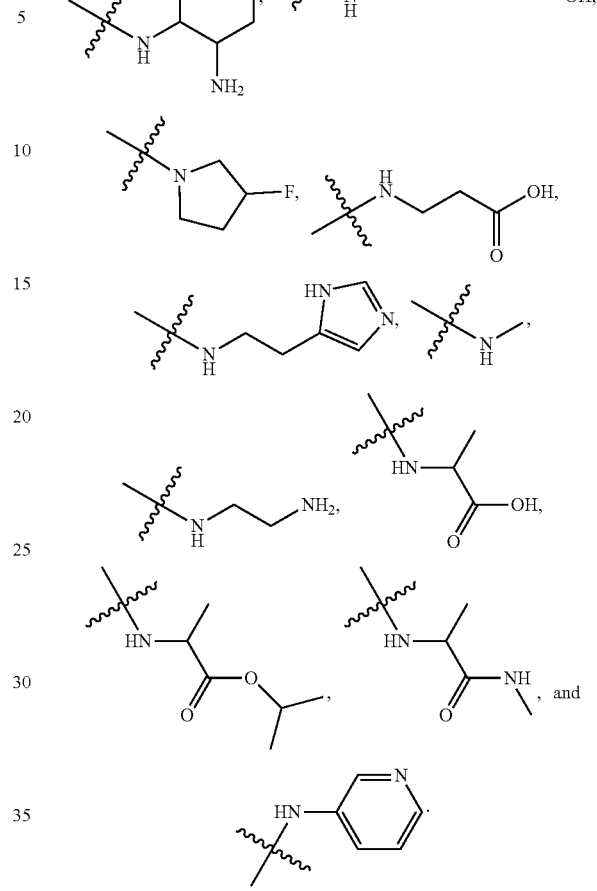
2. The compound of claim 1, wherein —XR$^1$ is selected from the group consisting of
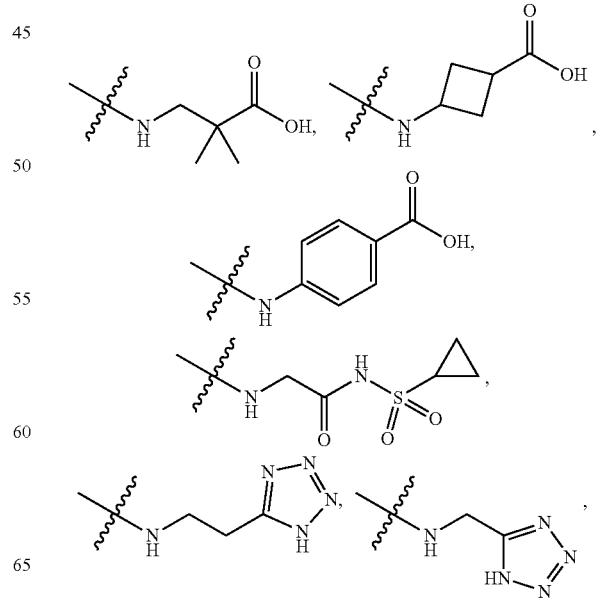

-continued

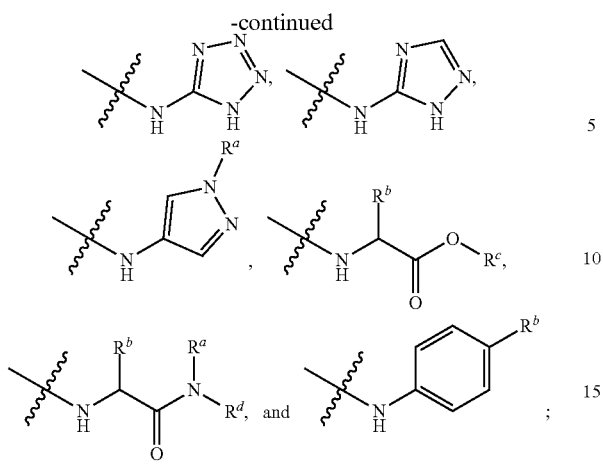

wherein, independently for each occurrence:
  $R^a$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl;
  $R^b$ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl;
  $R^c$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, and aminoalkyl; and
  $R^d$ is hydrogen or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, acyl, amino, amido, aminoalkyl, and alkoxyl; or, when —$XR^1$ is

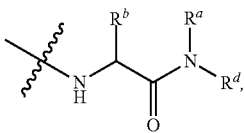

$R^a$ and $R^d$, together with the nitrogen to which they are attached, may form a substituted or unsubstituted 3- to 10-membered heterocyclic ring, wherein said ring is monocyclic, bicyclic, tricyclic, or spirocyclic.

3. The compound of claim 1, wherein —$XR^1$ is selected from the group consisting of

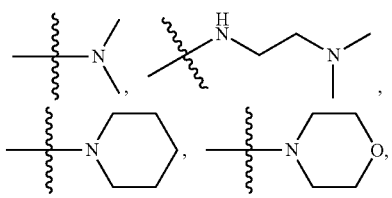

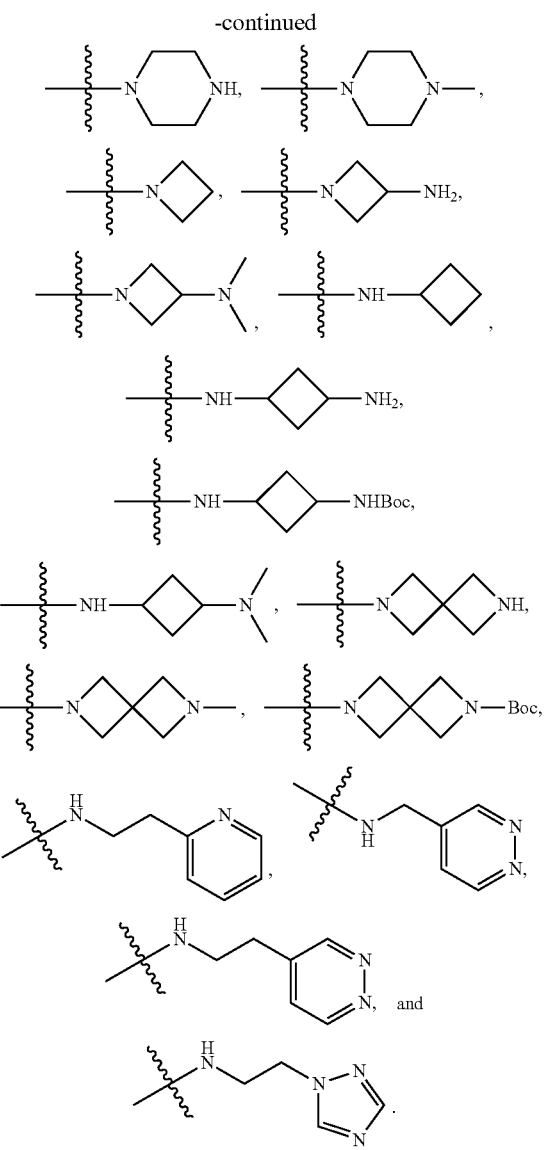

4. The compound of claim 1, wherein —$XR^1$ is selected from the group consisting of

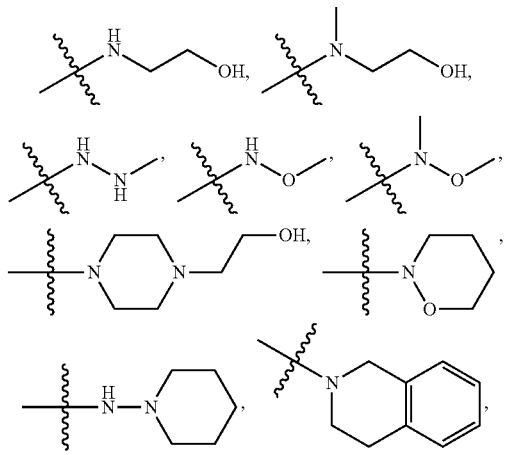

5. The compound of claim 1, wherein —XR[1] is selected from the group consisting of

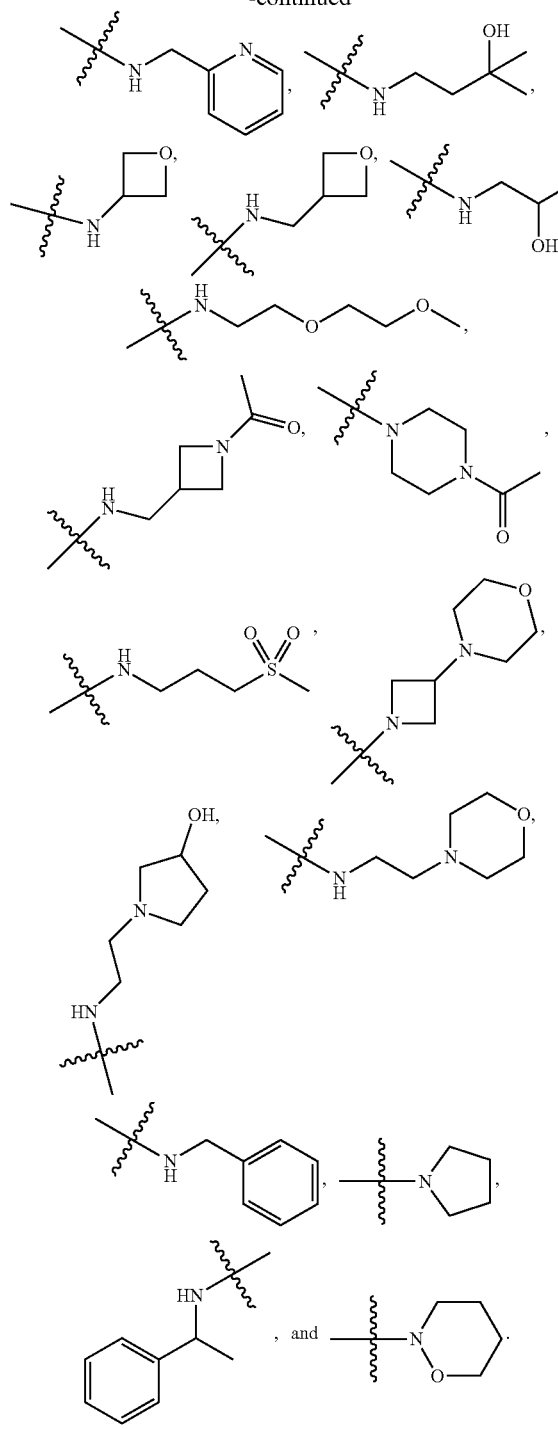

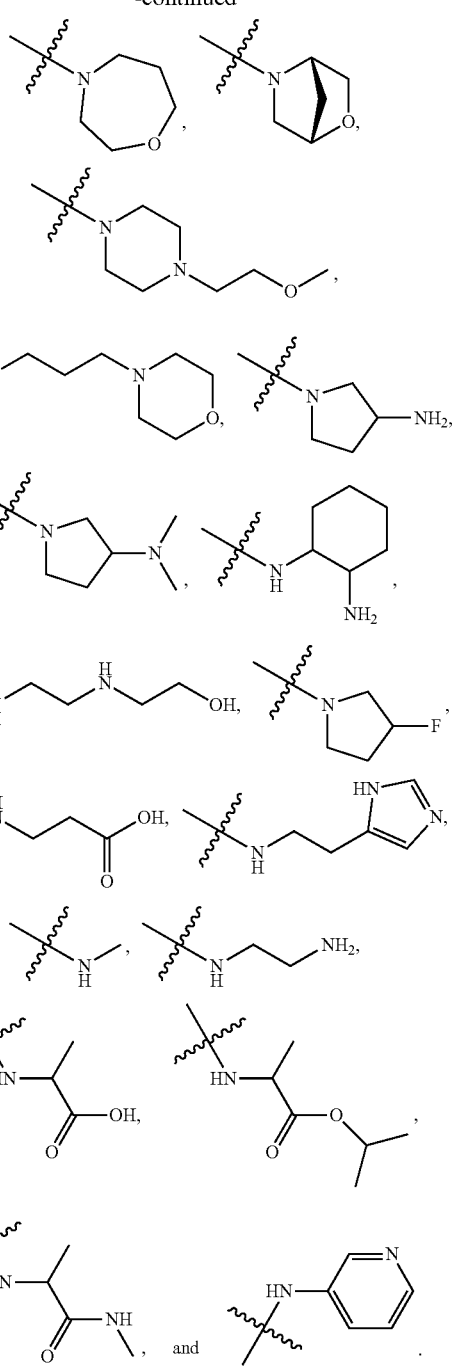

6. The compound of claim 1, wherein R[5] is hydrogen.

7. The compound of claim 1, wherein R[5] is alkyl.

8. The compound of claim 1, wherein R[5] is haloalkyl.

9. A pharmaceutical composition, comprising a compound of claim 1; and a pharmaceutically acceptable carrier.

10. A method of treating a fungal infection, comprising administering to a subject in need thereof a therapeutically effective amount of a compound of claim 1, thereby treating the fungal infection.

11. A compound represented by Formula (IVb) or a pharmaceutically acceptable salt thereof:

(IVb)

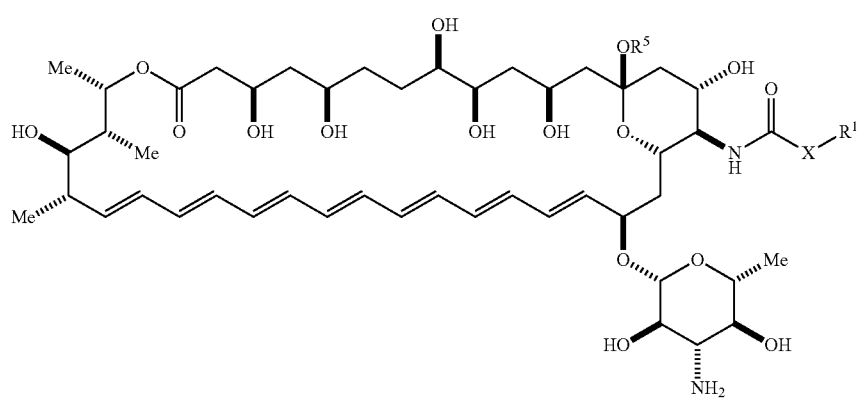

wherein, independently for each occurrence:

X is —C(R³)(R³)— or —O—;

R³ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl;

R⁵ is selected from the group consisting of hydrogen, alkyl, and haloalkyl;

when X is —C(R³)(R³)—, R¹ is hydrogen, halogen, hydroxyl, sulfhydryl, nitro, cyano, or a substituted or unsubstituted group selected from the group consisting of alkyl, cycloalkyl, (cycloalkyl)alkyl, heterocyclyl, (heterocyclyl)alkyl, aryl, heteroaryl, aralkyl, heteroaralkyl, carboxyl, acyl, acyloxy, amino, amido, azido, aminoalkyl, and alkoxyl; or the two instances of R³, together with the carbon to which they are attached, may form a substituted or unsubstituted 3- to 10-membered aliphatic or heterocyclic ring, wherein said ring is monocyclic, bicyclic, tricyclic, or spirocyclic; and when X is —O—, R¹ is a substituted or unsubstituted group selected from the group consisting of alkyl, alkenyl, cycloalkyl, (cycloalkyl)alkyl, heterocyclyl, (heterocyclyl)alkyl, aryl, heteroaryl, aralkyl, heteroaralkyl, acyl, amino, amido, and aminoalkyl.

12. The compound of claim 1, wherein X is —C(R³)(R³)—.

13. The compound of claim 1, wherein X is —O—.

14. The compound of claim 11, wherein —XR¹ is selected from the group consisting of methyl, ethyl, propyl, isopropyl, propenyl,

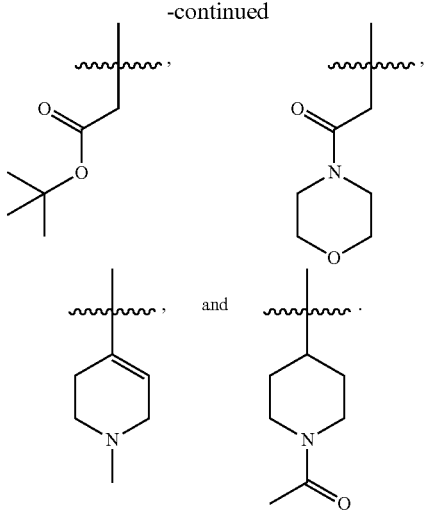

-continued

15. The compound of claim 11, wherein X is —O—; and R¹ is selected from the group consisting of methyl, ethyl, propyl, isopropyl, propenyl,

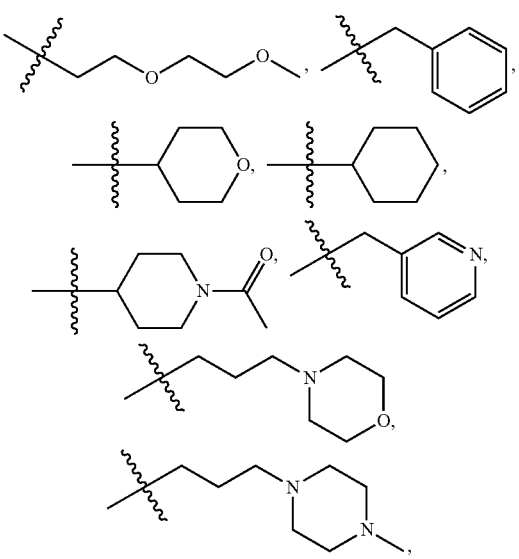

-continued

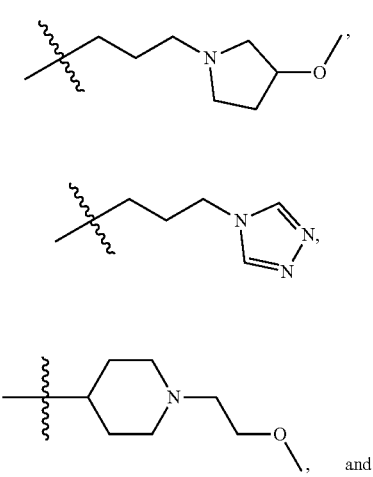

-continued

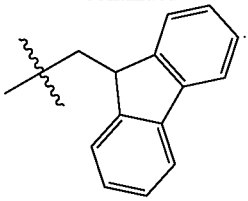

16. The compound of claim 11, wherein $R^5$ is hydrogen.
17. The compound of claim 11, wherein $R^5$ is alkyl.
18. The compound of claim 11, wherein $R^5$ is haloalkyl.
19. A pharmaceutical composition, comprising a compound of claim 11; and a pharmaceutically acceptable carrier.
20. A method of treating a fungal infection, comprising administering to a subject in need thereof a therapeutically effective amount of a compound of claim 11, thereby treating the fungal infection.

* * * * *